United States Patent
Jiang et al.

(10) Patent No.: US 11,072,662 B2
(45) Date of Patent: *Jul. 27, 2021

(54) HUMANIZED ANTI-CLL-1 ANTIBODIES

(71) Applicant: Cellerant Therapeutics, Inc., San Carlos, CA (US)

(72) Inventors: Ying-Ping Jiang, Lafayette, CA (US); Jagath R. Junutula, Fremont, CA (US); Leonard G. Presta, San Francisco, CA (US); Naoya Tsurushita, Palo Alto, CA (US)

(73) Assignee: Cellerant Therapeutics, Inc., Newark, CA (US)

( * ) Notice: Subject to any disclaimer, the term of this patent is extended or adjusted under 35 U.S.C. 154(b) by 169 days.

This patent is subject to a terminal disclaimer.

(21) Appl. No.: 15/779,025

(22) PCT Filed: Nov. 22, 2016

(86) PCT No.: PCT/US2016/063407
§ 371 (c)(1),
(2) Date: May 24, 2018

(87) PCT Pub. No.: WO2017/091615
PCT Pub. Date: Jun. 1, 2017

(65) Prior Publication Data
US 2018/0355044 A1   Dec. 13, 2018

Related U.S. Application Data

(60) Provisional application No. 62/259,100, filed on Nov. 24, 2015.

(51) Int. Cl.
| | |
|---|---|
| *C07K 16/28* | (2006.01) |
| *A61K 47/68* | (2017.01) |
| *C07K 16/24* | (2006.01) |
| *A61P 35/00* | (2006.01) |
| *A61K 31/5513* | (2006.01) |
| *A61K 35/15* | (2015.01) |
| *A61K 35/17* | (2015.01) |
| *C07K 16/46* | (2006.01) |
| *G01N 33/574* | (2006.01) |
| *G01N 33/68* | (2006.01) |

(52) U.S. Cl.
CPC ...... *C07K 16/2851* (2013.01); *A61K 31/5513* (2013.01); *A61K 35/15* (2013.01); *A61K 35/17* (2013.01); *A61K 47/6803* (2017.08); *A61K 47/6845* (2017.08); *A61K 47/6849* (2017.08); *A61P 35/00* (2018.01); *C07K 16/24* (2013.01); *C07K 16/2809* (2013.01); *C07K 16/468* (2013.01); *G01N 33/57492* (2013.01); *G01N 33/68* (2013.01); *C07K 2317/24* (2013.01); *C07K 2317/31* (2013.01); *C07K 2317/732* (2013.01); *G01N 2333/705* (2013.01)

(58) Field of Classification Search
CPC ............. C07K 16/2851; C07K 16/468; C07K 2317/732; A61K 47/6845; A61K 31/5513; G01N 33/68
See application file for complete search history.

(56) References Cited

U.S. PATENT DOCUMENTS

| | | | |
|---|---|---|---|
| 10,487,155 B2 * | 11/2019 | Moore | C07K 16/2809 |
| 2011/0256154 A1 | 10/2011 | Vincent et al. | |
| 2013/0295118 A1 * | 11/2013 | Jiang | A61P 19/00 |
| | | | 424/174.1 |
| 2017/0157265 A1 * | 6/2017 | Junutula | A61P 35/02 |

FOREIGN PATENT DOCUMENTS

| | | |
|---|---|---|
| EP | 2847222 A1 | 3/2015 |
| WO | 2016/149546 A1 | 6/2016 |
| WO | 2016/120218 A1 | 8/2016 |
| WO | 2016/179319 A1 | 11/2016 |
| WO | 2016179319 | 11/2016 |
| WO | 2017/011803 A1 | 1/2017 |
| WO | 2017091615 | 6/2017 |

OTHER PUBLICATIONS

PCT/US2016/063407, "International Search Report and Written Opinion", dated May 1, 2017, 11 pages.
PCT/US2016/063407, "Invitation to Pay Additional Fees and Partial Search Report", dated Feb. 3, 2017, 2 pages.
Noordhuis et al., "Targeting of CLEC12A in Acute Myeloid Leukemia by Antibody-Drug-Conjugates and Bispecific CLL-1 x CD3 biTE Antibody"; Biosis, Nov. 19, 2010.
Zhao et al., "Targeting C-type lectin-like molecule-1 for antibody-mediated immunotherapy in acute myeloid leukemia"; Haematologica, 95(1):71-78; Jul. 31, 2009.
Supplementary European Search Report from EP Application No. 16869193.9, dated Jun. 24, 2019.

* cited by examiner

Primary Examiner — Lei Yao

(57) ABSTRACT

Provided herein are humanized antibodies specific for CLL-1.

12 Claims, 22 Drawing Sheets
Specification includes a Sequence Listing.

Light Chain Variable

| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 |
|---|---|---|---|---|---|---|---|---|---|---|---|---|---|---|---|---|---|---|---|---|---|---|---|---|---|---|---|---|---|---|---|---|---|---|---|---|
| Sequential | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 |
| AbM | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 |
| Kabat | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 |
| | | | | | | | | | | | | | | | | | | | | | | | | | | | | | | | | | | | | |
| M26 | SEQ ID NO:1 | D | I | Q | M | T | Q | S | P | S | S | L | S | A | S | L | G | E | R | V | S | L | T | C | R | A | T | Q | E | L | S | G | Y | L | S | W |
| HuM26_L1 | SEQ ID NO:2 | D | I | Q | M | T | Q | S | P | S | S | L | S | A | S | V | G | D | R | V | T | I | T | C | R | A | T | Q | E | L | S | G | Y | L | S | W |
| HuM26_L4 | SEQ ID NO:3 | D | I | Q | M | T | Q | S | P | S | S | L | S | A | S | V | G | D | R | V | T | I | T | C | R | A | T | Q | E | L | S | G | Y | L | S | W |
| HuM26_L4D | SEQ ID NO:4 | D | I | Q | M | T | Q | S | P | S | S | L | S | A | S | V | G | D | R | V | T | L | T | C | R | A | T | Q | E | L | S | G | Y | L | S | W |
| HuM26_L4DR | SEQ ID NO:5 | D | I | Q | M | T | Q | S | P | S | S | L | S | A | S | V | G | D | R | V | T | I | T | C | R | A | T | Q | E | L | S | G | Y | L | S | W |
| IGKv1-16 | SEQ ID NO:6 | D | I | Q | M | T | Q | S | P | S | S | L | S | A | S | V | G | D | R | V | T | I | T | C | - | - | - | - | - | - | - | - | - | - | - | W |

CDR-L1 spans positions 24–34 (Kabat).

| | | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 |
|---|---|---|---|---|---|---|---|---|---|---|---|---|---|---|---|---|---|---|---|---|---|---|---|---|---|---|---|---|---|---|---|---|---|---|---|---|
| Sequential | | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 |
| AbM | | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 |
| Kabat | | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 |
| | | | | | | | | | | | | | | | | | | | | | | | | | | | | | | | | | | | | |
| M26 | | L | Q | Q | K | P | D | G | T | I | K | R | L | I | Y | A | A | S | T | L | D | S | G | V | P | K | R | F | S | G | S | R | S | G | T | D |
| HuM26_L1 | | F | Q | Q | K | P | G | K | A | P | K | S | L | I | Y | A | A | S | T | L | D | S | G | V | P | S | R | F | S | G | S | G | S | G | T | D |
| HuM26_L4 | | L | Q | Q | K | P | G | K | A | P | K | R | L | I | Y | A | A | S | I | L | D | S | G | V | P | S | R | F | S | G | N | G | S | G | T | D |
| HuM26_L4D | | L | Q | Q | K | P | G | K | A | P | K | R | L | I | Y | A | A | S | I | L | D | S | G | V | P | S | R | F | S | G | N | R | A | G | T | D |
| HuM26_L4DR | | L | Q | Q | K | P | G | K | A | P | K | R | L | I | Y | A | A | S | I | L | D | S | G | V | P | S | R | F | S | G | S | G | A | G | T | D |
| IGKv1-16 | | F | Q | Q | K | P | G | K | A | P | K | S | L | I | Y | - | - | - | - | - | - | - | G | V | P | S | R | F | S | G | S | G | S | G | T | D |

CDR-L2 spans positions 50–56 (Kabat).

| | | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|---|---|---|---|---|---|---|---|---|---|---|
| Sequential | | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
| AbM | | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
| Kabat | | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
| | | | | | | | | | | | | | | | | | | | | | | | | | | | | | | | | | | | | | | |
| M26 | | Y | S | L | T | I | S | S | L | E | S | E | D | F | A | D | Y | Y | C | L | Q | Y | A | I | Y | P | Y | T | F | G | G | G | T | K | L | E | I | K |
| HuM26_L1 | | F | T | L | T | I | S | S | L | Q | P | E | D | F | A | T | Y | Y | C | L | Q | Y | A | I | Y | P | Y | T | F | G | Q | G | T | K | L | E | I | K |
| HuM26_L4 | | Y | T | L | T | I | S | S | L | Q | P | E | D | F | A | T | Y | Y | C | L | Q | Y | A | I | Y | P | Y | T | F | G | Q | G | T | K | L | E | I | K |
| HuM26_L4D | | Y | T | L | T | I | S | S | L | Q | P | E | D | F | A | T | Y | Y | C | L | Q | Y | A | I | Y | P | Y | T | F | G | Q | G | T | K | L | E | I | K |
| HuM26_L4DR | | Y | T | L | T | I | S | S | L | Q | P | E | D | F | A | T | Y | Y | C | L | Q | Y | A | I | Y | P | Y | T | F | G | Q | G | T | K | L | E | I | K |
| IGKv1-16 | | F | T | L | T | I | S | S | L | Q | P | E | D | F | A | T | Y | Y | C | - | - | - | - | - | - | - | - | - | F | G | Q | G | T | K | L | E | I | K |

CDR-L3 spans positions 89–97 (Kabat).

*FIG. 1A*

Heavy Chain Variable

| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 |
|---|---|---|---|---|---|---|---|---|---|---|---|---|---|---|---|---|---|---|---|---|---|---|---|---|---|---|---|---|---|---|---|---|---|---|---|---|
| Sequential | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 |
| AbM | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 |
| Kabat | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 |
| M26 | SEQ ID NO:7 | E | V | Q | L | Q | Q | S | G | P | E | L | V | K | P | G | A | S | V | K | M | S | C | K | A | S | G | Y | T | F | T | S | Y | F | I | H |
| HuM26_H4a | SEQ ID NO:8 | E | V | Q | L | V | Q | S | G | A | E | V | K | K | P | G | A | S | V | K | V | S | C | K | A | S | G | Y | T | F | T | S | Y | F | I | H |
| IGHV1-46 | SEQ ID NO:9 | Q | V | Q | L | V | Q | S | G | A | E | V | K | K | P | G | A | S | V | K | V | S | C | K | A | S | G | Y | T | F | T | S | Y | F | I | H |

CDR-H1: positions 26-35

| | 36 | 37 | 38 | 39 | 40 | 41 | 42 | 43 | 44 | 45 | 46 | 47 | 48 | 49 | 50 | 51 | 52 | 52A | 53 | 54 | 55 | 56 | 57 | 58 | 59 | 60 | 61 | 62 | 63 | 64 | 65 | 66 | 67 | 68 | 69 | 70 |
|---|---|---|---|---|---|---|---|---|---|---|---|---|---|---|---|---|---|---|---|---|---|---|---|---|---|---|---|---|---|---|---|---|---|---|---|---|
| Sequential | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | |
| AbM | 36 | 37 | 38 | 39 | 40 | 41 | 42 | 43 | 44 | 45 | 46 | 47 | 48 | 49 | 50 | 51 | 52 | 52A | 53 | 54 | 55 | 56 | 57 | 58 | 59 | 60 | 61 | 62 | 63 | 64 | 65 | 66 | 67 | 68 | 69 | |
| Kabat | 36 | 37 | 38 | 39 | 40 | 41 | 42 | 43 | 44 | 45 | 46 | 47 | 48 | 49 | 50 | 51 | 52 | 52A | 53 | 54 | 55 | 56 | 57 | 58 | 59 | 60 | 61 | 62 | 63 | 64 | 65 | 66 | 67 | 68 | 69 | |
| M26 | W | V | K | Q | K | P | G | Q | G | L | E | W | I | G | F | I | N | P | Y | N | D | G | S | K | Y | N | E | K | F | K | G | K | A | T | L | |
| HuM26_H4a | W | V | R | Q | A | P | G | Q | G | L | E | W | I | G | L | I | N | P | Y | N | D | G | S | K | Y | A | Q | K | F | Q | G | R | A | T | L | |
| IGHV1-46 | W | V | R | Q | A | P | G | Q | G | L | E | W | M | G | L | I | N | P | Y | N | D | G | S | Y | A | Q | K | F | Q | G | R | V | T | M | | |

CDR-H2: positions 50-58

| | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 | 95 | 96 |
|---|---|---|---|---|---|---|---|---|---|---|---|---|---|---|---|---|---|---|---|---|---|---|---|---|---|---|---|---|---|
| Sequential | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | | | |
| AbM | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | | | |
| Kabat | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | | | |
| M26 | T | S | D | K | S | S | S | T | A | Y | M | E | L | S | S | L | T | S | E | D | S | A | V | Y | Y | C | | | |
| HuM26_H4a | T | S | D | K | S | T | S | T | V | Y | M | E | L | R | S | L | R | S | E | D | T | A | V | Y | Y | C | | | |
| IGHV1-46 | T | R | D | T | S | T | S | T | V | Y | M | E | L | R | S | L | R | S | E | D | T | A | V | Y | Y | C | | | |

| | 97 | 98 | 99 | 100 | 101 | 102 | 103 | 104 | 105 | 106 | 107 | 108 | 109 | 110 | 111 | 112 | 113 | 114 | 115 | 116 | 117 | 118 | 119 | 120 |
|---|---|---|---|---|---|---|---|---|---|---|---|---|---|---|---|---|---|---|---|---|---|---|---|---|
| Sequential | 97 | 98 | 99 | 100 | 101 | 102 | 103 | 104 | 105 | 106 | 107 | 108 | 109 | 110 | 111 | 112 | 113 | 114 | 115 | 116 | 117 | 118 | 119 | 120 |
| AbM | 93 | 94 | 95 | 96 | 97 | 98 | 99 | 100 | 100A | 100B | 100C | 101 | 102 | 103 | 104 | 105 | 106 | 107 | 108 | 109 | 110 | 111 | 112 | 113 |
| Kabat | 93 | 94 | 95 | 96 | 97 | 98 | 99 | 100 | 100A | 100B | 100C | 101 | 102 | 103 | 104 | 105 | 106 | 107 | 108 | 109 | 110 | 111 | 112 | 113 |
| M26 | T | R | D | D | G | Y | Y | G | Y | A | M | D | Y | W | G | Q | G | T | L | V | T | V | S | S |
| HuM26_H4a | T | R | D | D | G | Y | Y | G | Y | A | M | D | Y | W | G | Q | G | T | L | V | T | V | S | S |
| IGHV1-46 | A | R | – | – | – | – | – | – | – | – | – | – | – | – | – | – | – | – | – | – | – | – | – | – |

CDR-H3: positions 99-109

FIG. 1B

Light Chain Variable

FIG. 2A

Heavy Chain Variable

FIG. 2B

| Sequential | 97 | 98 | 99 | 100 | 102 | 103 | 104 | 105 | 106 | 107 | 108 | 109 | 110 | 111 | 112 | 113 | 114 | 115 | 116 | 117 | 118 | 119 | 120 | 121 |
|---|---|---|---|---|---|---|---|---|---|---|---|---|---|---|---|---|---|---|---|---|---|---|---|---|
| IMGT | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 126 | 128 |
| Kabat | 93 | 94 | 95 | 96 | 97 | 98 | 99 | 100 | 100A | 100B | 100C | 101 | 102 | 103 | 104 | 105 | 106 | 107 | 108 | 109 | 110 | 111 | 112 | 113 |
| | | | | | | | | | | | | | | | | | | CDR-H3 | | | | | | |
| M31 | A | R | P | I | Y | F | D | N | D | Y | F | D | Y | W | G | Q | G | T | T | L | K | V | S | S |
| HuM31VH v1 | A | R | P | I | Y | F | D | N | D | Y | F | D | Y | W | G | Q | G | T | T | V | T | V | S | S |
| HuM31VH v2 | A | R | P | I | Y | F | D | N | D | Y | F | D | Y | W | G | Q | G | T | T | V | T | V | S | S |
| HuM31VH v3 | A | R | P | I | Y | F | D | N | D | Y | F | D | Y | W | G | Q | G | T | L | V | T | V | S | S |
| HuM31VH v4 | A | R | P | I | Y | F | D | N | D | Y | F | D | Y | W | G | Q | G | T | T | V | T | V | S | S |
| AF174092_VH | A | R | - | - | - | - | - | - | - | - | - | - | - | W | G | Q | G | T | L | V | T | V | S | S |
| M17751_VH | A | R | - | - | - | - | - | - | - | - | - | - | - | W | G | Q | G | T | L | V | T | V | S | S |

Lefranc, M.-P. et al. "IMGT unique numbering for immunoglobulin and T cell receptor variable domains and Ig superfamily V-like domains. Dev. Comp. Immunol., 27, 55-77 (2003).
world wide web site: imgt.org/IMGTScientificChart/Numbering/IMGTnumberingCDR_VK.html

*FIG. 2C*

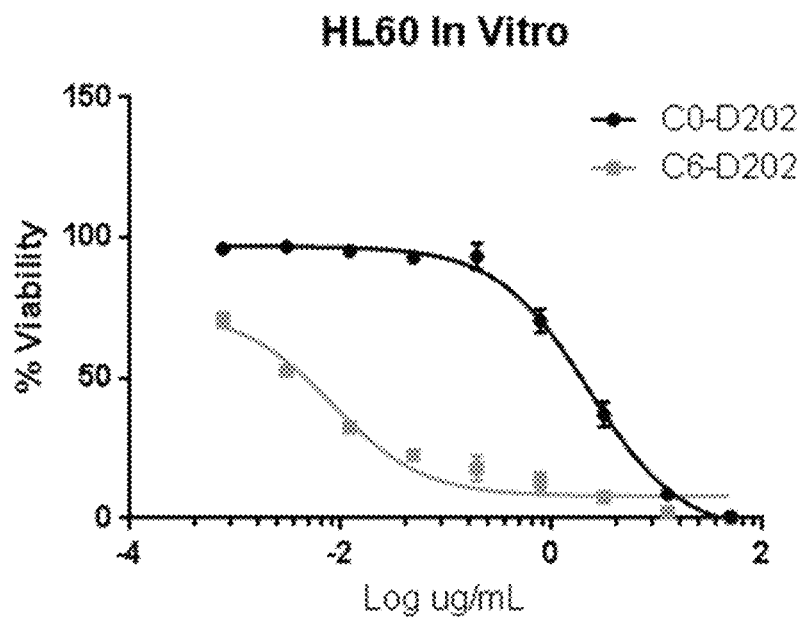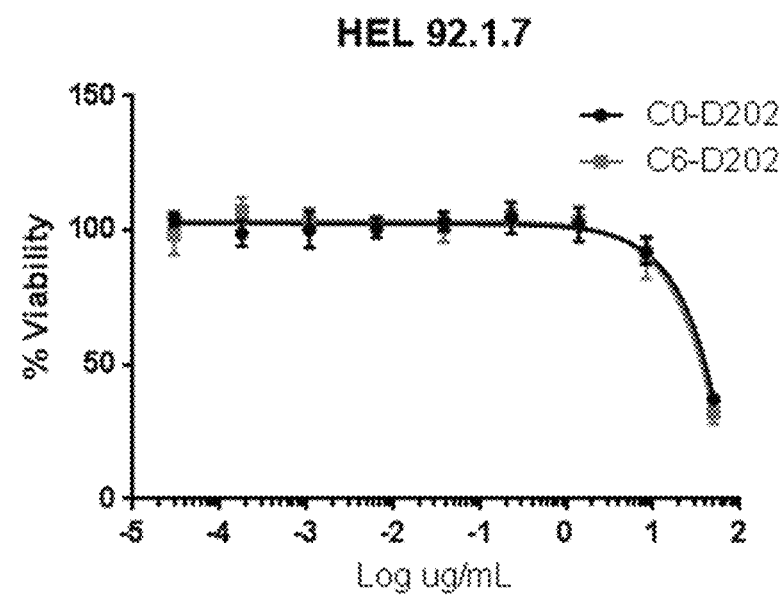
FIG. 13

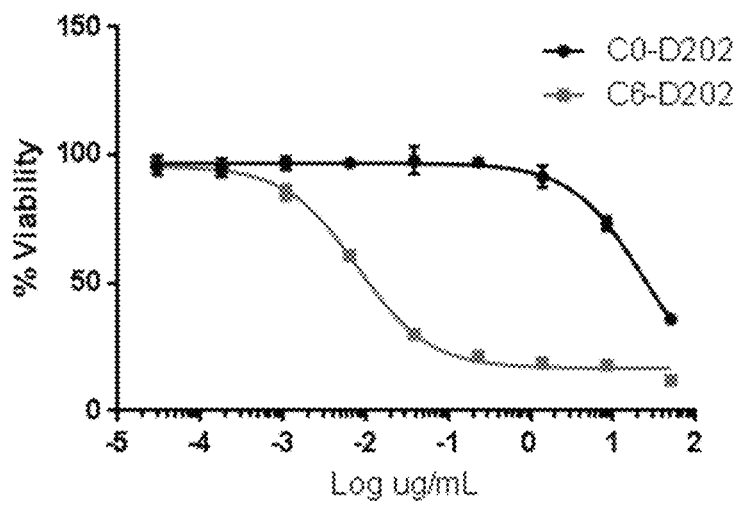
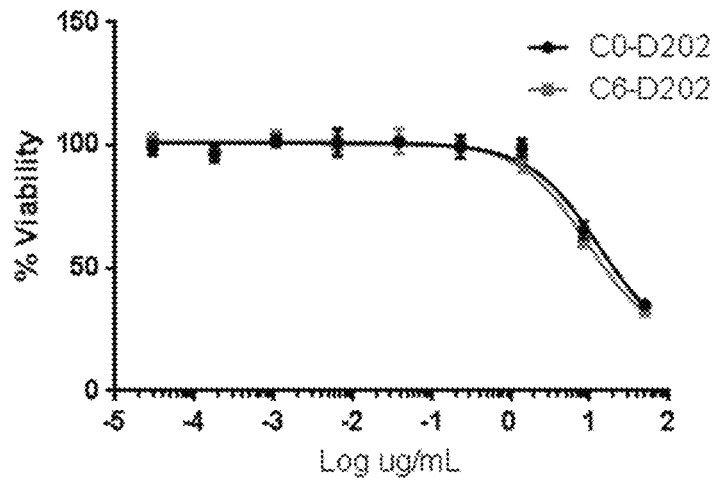
FIG. 14

HUMANIZED ANTI-CLL-1 ANTIBODIES

CROSS-REFERENCED TO RELATED PATENT APPLICATIONS

The present patent application claims benefit of priority to U.S. Provisional Patent Application No. 62/259,100, filed Nov. 24, 2015, which is incorporated by referenced for all purposes.

BACKGROUND OF THE INVENTION

C type Lectin Like molecule 1 (CLL-1) is expressed on AML cells, and on cancer stem cells (CSCs), which are cells that can give rise to additional cancer cells.

One of the major limitations of chemotherapy is the general inability of anticancer drugs to discriminate between normal and cancer cells. Almost all members of the major categories of antineoplastic agents have considerable toxicity for normal cells.

Compositions that specifically target cancer cells can avoid this problem. However, existing cancer targets do not target CSCs. For this reason, existing chemotherapeutic strategies, even when specifically delivered to cancer cells, do not effectively eliminate the cancer. Risk of recurrence remains because the surviving CSCs can give rise to new cancer cells.

CSCs express CD34, similar to hematopoietic stem cells (HSCs), but CLL-1 is not expressed on HSCs. This allows CSCs to be specifically selected by targeting CLL-1.

SUMMARY OF THE INVENTION

Provided herein are humanized anti-CLL-1 antibodies that recognize a high percentage of CLL-1 expressing cells, but are less immunogenic and better tolerated than murine or chimeric antibodies. The present humanized anti-CLL-1 antibodies are effective for both complement dependent and antibody dependent cytotoxicity of CLL-1 expressing cells, and inhibit tumor growth of CLL-1 expressing cancer cells. The presently described antibodies provide novel diagnostic and therapeutic strategies for targeting CLL-1-associated disorders.

In one aspect provided herein is a humanized antibody that binds CLL-1 and comprises a variable light chain and a variable heavy chain, wherein: a. the variable light chain further comprises a CDRL1, CDRL2 and CDRL3 of murine M26, and the human framework sequences of IgKv1-16, except wherein: i. Kabat residue 21 may be either murine or human; ii. Kabat residue 36 may be either murine or human, iii. Kabat residue 44 may be either murine or human, iv. Kabat residue 46 may be either murine or human, v. Kabat residue 65 may be either murine or human, vi. Kabat residue 66 may be either murine or human, vii. Kabat residue 67 may be human or Ala ("A"), viii. Kabat residue 71 may be either murine or human, and b. the variable heavy chain comprises CDRH1, CDRH2 and CDRH3 of murine M26, and the human framework sequences of IGHV1-46, except wherein: i. Kabat residue 1 may be either murine or human, ii. Kabat residue 20 may be either murine or human, iii. Kabat residue 48 may be either murine or human, iv. Kabat residue 67 may be either murine or human, v. Kabat residue 69 may be either murine or human, vi. Kabat residue 71 may be either murine or human, vii. Kabat residue 73 may be either murine or human, viii. Kabat residue 93 may be either murine or human. In one embodiment variable heavy chain Kabat residues 103-113 are murine. In another embodiment at least one, at least two, at least three, at least four, at least five, at least six, at least seven, or eight of variable heavy chain Kabat residues 1, 20, 48, 67 69, 71, 73 and 93 is murine. In another embodiment the anti-CLL-1 humanized antibody comprises a variable light chain and a variable heavy chain, wherein: a. the variable light chain comprises a sequence selected from HuM26L4, HuM26L4D and HuM26L4DR, and b. the variable heavy chain comprises the sequence HuM26VH4.

In one aspect provided herein is a humanized antibody that binds CLL-1 comprising a variable light chain and a variable heavy chain, wherein: a. the variable light chain comprises a CDRL1, CDRL2 and CDRL3 of murine M31, and the human framework sequences of X02990, except wherein: i. Kabat residue 60 may be human or D ("Asp"), and ii. Kabat residue 68 may be either the murine or human; and b. the variable heavy chain comprises a CDRH1, CDRH2 and CDRH3 of murine M31, and the human framework sequences of: i. AF174092, except wherein: 1. Kabat residue 43 may be either human or R ("Arg"), 2. Kabat residue 48 is murine, 3. Kabat residues 58-65 are murine, 4. Kabat residue 66 may be either murine or human, 5. Kabat residue 67 may be either murine or human, 6. Kabat residue 69 may be murine or I ("Ile"), 7. Kabat residue 71 is murine, 8. Kabat residue 75 may be human or T ("Thr"), 9. Kabat residue 82A may be human or R ("Arg"), 10. Kabat residue 85 may be either murine or human, or ii. M17751, except where: 1. Kabat residue 43 may be human or R ("Arg"), 2. Kabat residue 48 is murine, 3. Kabat residues 58-65 are murine, 4. Kabat residue 66 may be either murine or human, 5. Kabat residue 67 may be either murine or human, 6. Kabat residue 69 may be murine or human, 7. Kabat residue 71 is murine, 8. Kabat residue 75 may be human or T ("Thr"), 9. Kabat residue 82A may be human or R ("Arg"), 10. Kabat residue 85 may be human or D ("Asp").

For the purposes of this disclosure, "murine" framework amino acid residues are those framework amino acid residues in M26 or M31 as shown in FIG. 1A-B or 2A-C, respectively. "Human" framework amino acid residues for M26 are those shown for "IGKv1-16" in FIG. 1A for the light chain variable chain and "IGHV1-26" in FIG. 1B for the heavy chain variable chain, for M31 are those shown for "X02990VL" in FIG. 2A for the light chain variable chain and "AF174092_VH" or "M17751_VH" in FIGS. 2B-2C for the heavy chain variable chain.

In another aspect this disclosure provides an anti-CLL-1 humanized antibody comprising a variable light chain and a variable heavy chain, wherein: a. the variable light chain comprises a sequence selected from HuM31VL1 and HuM31VL2; and b. the variable heavy chain comprises a sequence selected from HuM31VH1, HuM31VH2, HuM31VH3 and HuM31VH4.

In another embodiment of an antibody of this disclosure, the variable light chain comprises HuM26L4. In another embodiment the variable light chain comprises HuM26L4D. In another embodiment the variable light chain comprises HuM26L4DR. In another embodiment the antibody comprises HuM31VH2 (SEQ ID NO:16) and HuM31VL2 (SEQ ID NO:12), or HuM31VH3 (SEQ ID NO:17) and HuM31VL2 (SEQ ID NO:12). In another embodiment the antibody further comprises a human constant region selected from IgG1, IgG2, IgG3 and IgG4. In one embodiment the antibody is a bi-specific antibody comprising a first arm that binds CLL-1 and a second arm that binds a second target antigen, e.g., CD33, CD123, IL1Rap, GPR114. In another embodiment the antibody is a bi-specific antibody comprising a first arm that binds CLL-1 and a second arm that binds CD3 antigen on T cells. In another embodiment the antibody is a cysteine-substituted antibody.

Also provided is an antibody that binds CLL-1, the antibody comprising: a variable light chain comprising SEQ ID NO: 21, wherein at least one variable position in SEQ ID NO:21 is an amino acid from SEQ ID NO:6 at the same position; and a variable heavy chain comprising SEQ ID NO: 23, wherein at least one variable position in SEQ ID NO:23 is an amino acid from SEQ ID NO:9 at the same position. In some embodiments,
i. the variable light chain comprises SEQ ID NO:22,
ii. the variable heavy chain comprises SEQ ID NO:24, or
iii. the variable light chain comprises SEQ ID NO:22 and the variable heavy chain further comprises SEQ ID NO:24.

In some embodiments, at least one, at least two, at least three, at least four, at least five, at least six, at least seven, or eight of variable heavy chain Kabat residues 1, 20, 48, 67 69, 71, 73 and 93 is murine. In some embodiments, at least one, at least two, at least three, at least four, at least five, at least six, at least seven, or eight of variable heavy chain Kabat residues 1, 20, 48, 67 69, 71, 73 and 93 is human. In some embodiments, at least one, at least two, at least three, at least four, at least five, at least six, at least seven, or eight of variable heavy chain Kabat residues 21, 36, 44, 46, 65, 66, 67, or 71 is murine. In some embodiments, at least one, at least two, at least three, at least four, at least five, at least six, at least seven, or eight of variable heavy chain Kabat residues 21, 36, 44, 46, 65, 66, 67, or 71 is human.

In some embodiments, light chain Kabat residues 65-67 are NRA or NGA.

In some embodiments, the variable light chain comprises SEQ ID NO:3; SEQ ID NO:4, or SEQ ID NO:5, and the variable heavy chain comprises SEQ ID NO:8. In some embodiments, the variable light chain comprises SEQ ID NO:3. In some embodiments, the variable light chain comprises SEQ ID NO:4. In some embodiments, the variable light chain comprises SEQ ID NO:5.

Also provided is an antibody that binds CLL-1, the antibody comprising: a variable light chain comprising SEQ ID NO: 25, wherein at least one variable position in SEQ ID NO:25 is an amino acid from SEQ ID NO:13 at the same position; and a variable heavy chain comprising: SEQ ID NO: 26, wherein at least one variable position in SEQ ID NO:26 is an amino acid from SEQ ID NO:19 at the same position, or SEQ ID NO:27, wherein at least one variable position in SEQ ID NO:27 is an amino acid from SEQ ID NO:20 at the same position. In some embodiments, the variable light chain comprises SEQ ID NO:11 or SEQ ID NO:12; and the variable heavy chain comprises SEQ ID NO:15, SEQ ID NO:16, SEQ ID NO:17, or SEQ ID NO:18. In some embodiments, the antibody comprises SEQ ID NO:16 and SEQ ID NO:12, or SEQ ID NO:17 and SEQ ID NO:12. In some embodiments, the antibody comprises a human constant region selected from IgG1, IgG2, IgG3 and IgG4.

In some embodiments, the antibody is a bi-specific antibody comprising a first arm that binds CLL-1 and a second arm that binds a second target antigen, e.g., CD33, CD123, IL1Rap, GPR114. In some embodiments, the antibody is a bi-specific antibody comprising a first arm that binds CLL-1 and a second arm that binds CD3 antigen on T cells.

In some embodiments, the antibody is a cysteine-substituted antibody, e.g., including but not limited to having a cysteine substitution in the constant (Fc) region.

In some embodiments, the antibody is linked to a cytotoxic agent. In some embodiments, the cytotoxic agent is a benzodiazepine. In some embodiments, the benzodiazepine is selected from a pyrrolo benzodiazepine, an indolino benzodiazepines and an isoquinolidinobenzodiazepine, or a hetero dimer or homo dimer thereof.

In another aspect provided herein is a chimeric antigen receptor comprising: a. a target binding domain that binds CLL-1 and that comprises a binding portion of a variable light and a variable heavy chain selected from claim 1 or claim 3 (e.g., an scFv domain); b. a hinge region; c. a transmembrane domain (TM); and d. an intracellular domain comprising at least one signal transduction domain (e.g., CD3ζ).

In another aspect provided herein is a nucleic acid comprising a nucleotide sequence encoding the antibody or a chimeric antigen receptor of any of this disclosure. In one embodiment the nucleotide sequence is operably linked to an expression control sequence. In another embodiment the nucleic acid is comprised in an expression vector.

In another aspect provided herein is a recombinant cell comprising the nucleic acid of this disclosure. In one embodiment the nucleotide sequence encodes a chimeric antigen receptor, and the cell is a cell of lymphoid or myeloid lineage.

In another aspect provided herein is a process for making an antibody or a chimeric antigen receptor comprising culturing the recombinant cell of this disclosure. In one embodiment the process further comprises isolating the antibody.

In another aspect provided herein is a composition comprising the antibody of this disclosure and an adjuvant. In one embodiment composition is pharmaceutically acceptable.

In another aspect provided herein is a method of detecting a cell expressing CLL-1 comprising: a. contacting a cell with an effective amount of an antibody of this disclosure, that is capable of binding the cell, and b. detecting binding of the antibody to the cell, wherein binding indicates the presence of the cell of interest.

In another aspect provided herein is a method of diagnosing a disease comprising: a. contacting a biological sample from an individual with an effective amount of an antibody of this disclosure capable of binding to diseased cells, and b. detecting binding of the antibody to a diseased cell, wherein binding indicated the presence of the disease. In one embodiment the antibody is conjugated to a detectable moiety. In another embodiment the disease is cancer. In another embodiment the cell is a tumor cell or a cancer stem cell. In another embodiment the disease is a myeloproliferative disorder. In another embodiment the myeloproliferative disorder is selected from the group consisting of AML, CML, CMML, multiple myeloma, plasmacytoma and myelofibrosis.

In another aspect provided herein is a method of inhibiting cell division comprising contacting a cell with at least an effective amount of an antibody of this disclosure 13 capable of binding the cell. In one embodiment the inhibition of cell division results in cell death. In another embodiment the cell is a tumor or cancer stem cell. In another embodiment the tumor or cancer stem cells are from a myeloproliferative disorder. In another embodiment the myeloproliferative disorder is selected from the group consisting of: AML, CML, CMML, multiple myeloma, plasmacytoma and myelofibrosis.

In another aspect provided herein is a method of treating cancer comprising administering to a patient a therapeutically effective amount of an antibody of this disclosure. In one embodiment the antibody is an antibody conjugate which is conjugated with a potent cytotoxic drug via a cleavable, non-cleavable or traceless linker. In another embodiment the drug is selected from the group consisting of: maytansinoid, auristatin, dolastatin, tubulysin, cryptophycin, pyrrolobenzodiazepine (PBD) dimer, indolinobenzodiazepine dimer, alpha-amanitin, trichothene, SN-38, duocarmycin, CC1065, calicheamincin, an enediyne antibioatic, taxane, doxorubicin derivatives, anthracycline and stereoisomers, azanofide, isosteres, analogs or derivatives thereof. In another embodiment the cancer is a myeloproliferative disorder. In another embodiment the myeloproliferative disorder is selected from the group consisting of: AML, CML, CMML, multiple myeloma, pasmocytoma and myelofibrosis. In another embodiment the tumor associated antigen or cancer stem cell antigen is CLL-1.

In another aspect provided herein is a method of treating a cancer characterized by cancer cells that express CLL-1, comprising administering to a subject a cell that expresses a chimeric antigen receptor of this disclosure. In one embodiment the cancer is as leukemia, e.g., selected from AML (acute myelogenous leukemia), MDS (myelodysplastic syndrome), and CML (chronic myelogenous leukemia). In another embodiment the cell is a cell of lymphoid or myeloid lineage.

BRIEF DESCRIPTION OF THE DRAWINGS

FIGS. 1A and 1B show a comparison of various humanized M26 antibodies, showing the CDR sequences shaded (light or dark gray) and bolded underline, along with numbering in sequential, AbM and Kabat formats. Positions in which a human amino acid is replaced with a corresponding mouse amino acid are boxed. FIG. 1A shows the variable light chain sequences of (i) murine M26 (SEQ ID NO:1), (ii) humanized HuM26_L1 (SEQ ID NO:2), HuM26_L4 (SEQ ID NO:3), HuM26_L4D (SEQ ID NO:4), HuM26_L4DR (SEQ ID NO:5) and (iii) the human donor sequence IGKv1-16 (SEQ ID NO:6). The variable light chain sequence of M26 can also be represented by the following:

Figure 3:
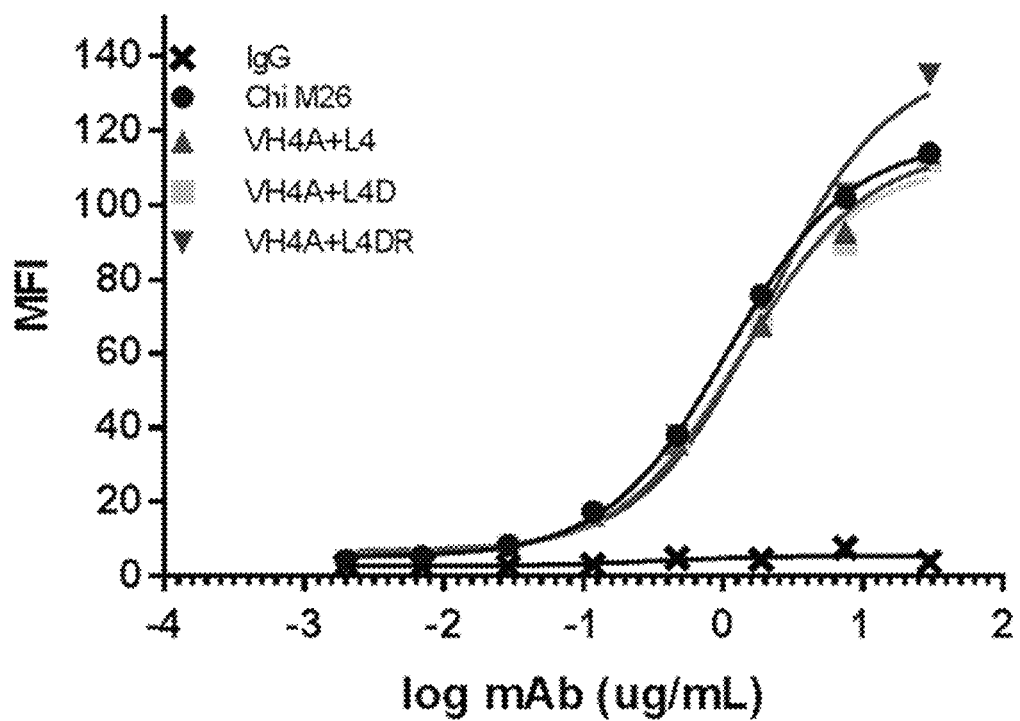

```
SEQ ID NO: 21
Light chain humanized M26
D I Q M T      Q       S       P       S       S       L       S       A
S V G D        R       V       T       (I/L)   T       C       R       A
T Q E L        S       G       Y       L       S       W       (F/L)   Q
Q K P G        K       A       (P/I)   K       (S/R)   L       I       Y
A A S T        L       D       S       G       V       P       S       R
F S G (S/N)    (G/R)   (S/A)   G       T       D       (F/Y)   T       L
T I S S        L       Q       P       E       D       F       A       T
Y Y C L        Q       Y       A       I       Y       P       Y       T.
```

SEQ ID NO:22
Further framework sequence for light chain humanized M26 directly after SEQ ID NO:21: FGQGTKLEIK.

FIG. 1B shows the variable heavy chain sequence of (i) murine M26 (SEQ ID NO:7), (ii) humanized HuM26_H4a (SEQ ID NO:8), and the human donor sequence IGHV1-46 (SEQ ID NO:9). The variable heavy chain sequence of M26 can also be represented by the following:

```
SEQ ID NO: 23
Heavy chain humanized M26
(CDRS bold and underlined, different options at a
position are shown in parentheses)
(Q/E) V        Q L V Q S G      A E       V K       K
       P       G A S V K (V/M)  S C       K A       S
       G       Y T F T S Y      F I       H W       V
       R       Q A P G Q G      L E       W (M/I)   G
       F       I N P Y N D      G S       K Y       A
       Q       K F Q G R (V/A)  T (M/L)   T (R/S)   D
       (T/K)   S T S T V Y      M E       L S       S
       L       R S E D T A      V Y       Y C       
       (A/T)   R D D G Y Y      G Y       A M       D
       Y.
```

SEQ ID NO:24
Further framework sequence for heavy chain humanized M26 directly after SEQ ID NO:23: WGQGTLVTVSS.

Figure 2A:
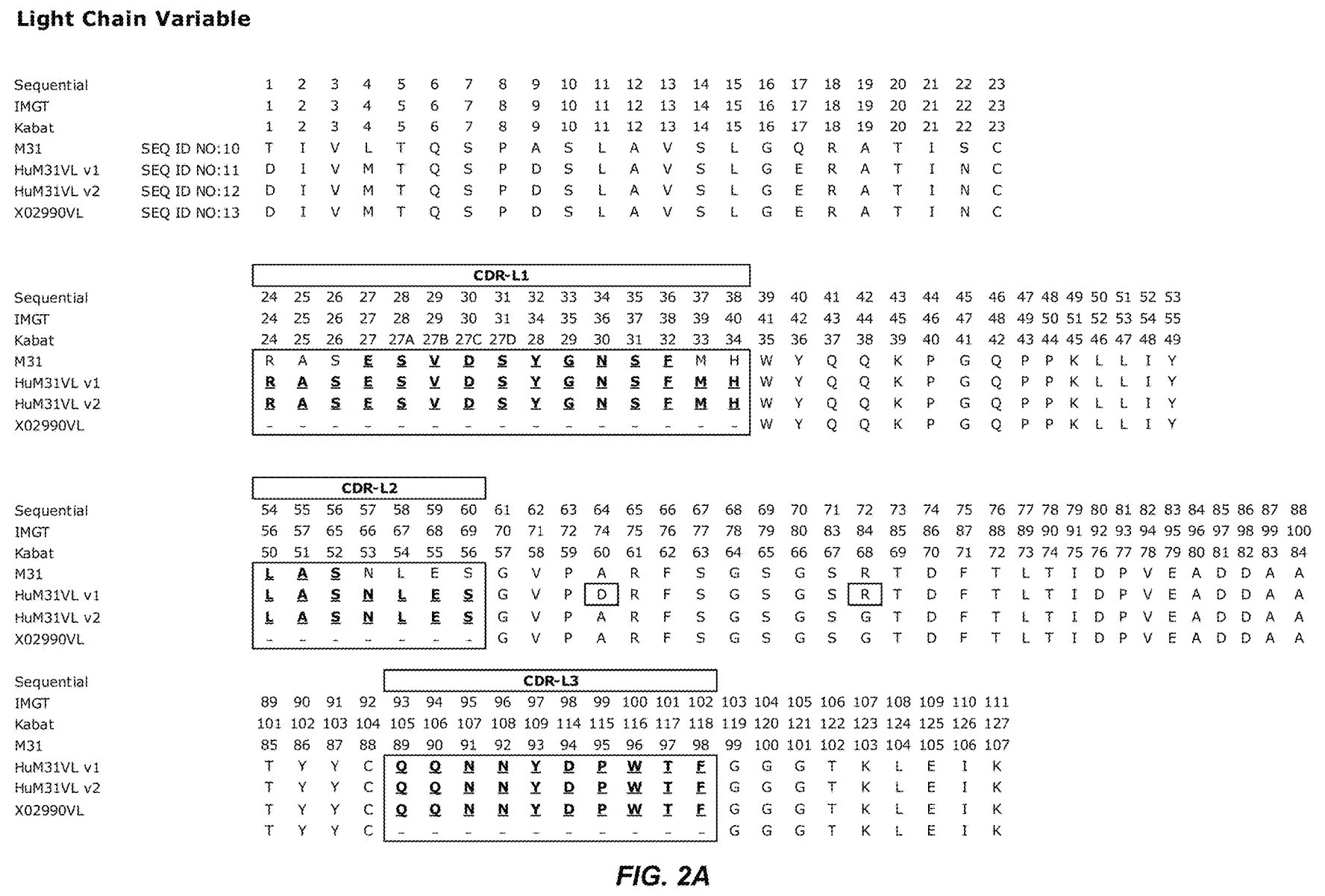
Figure 2B:
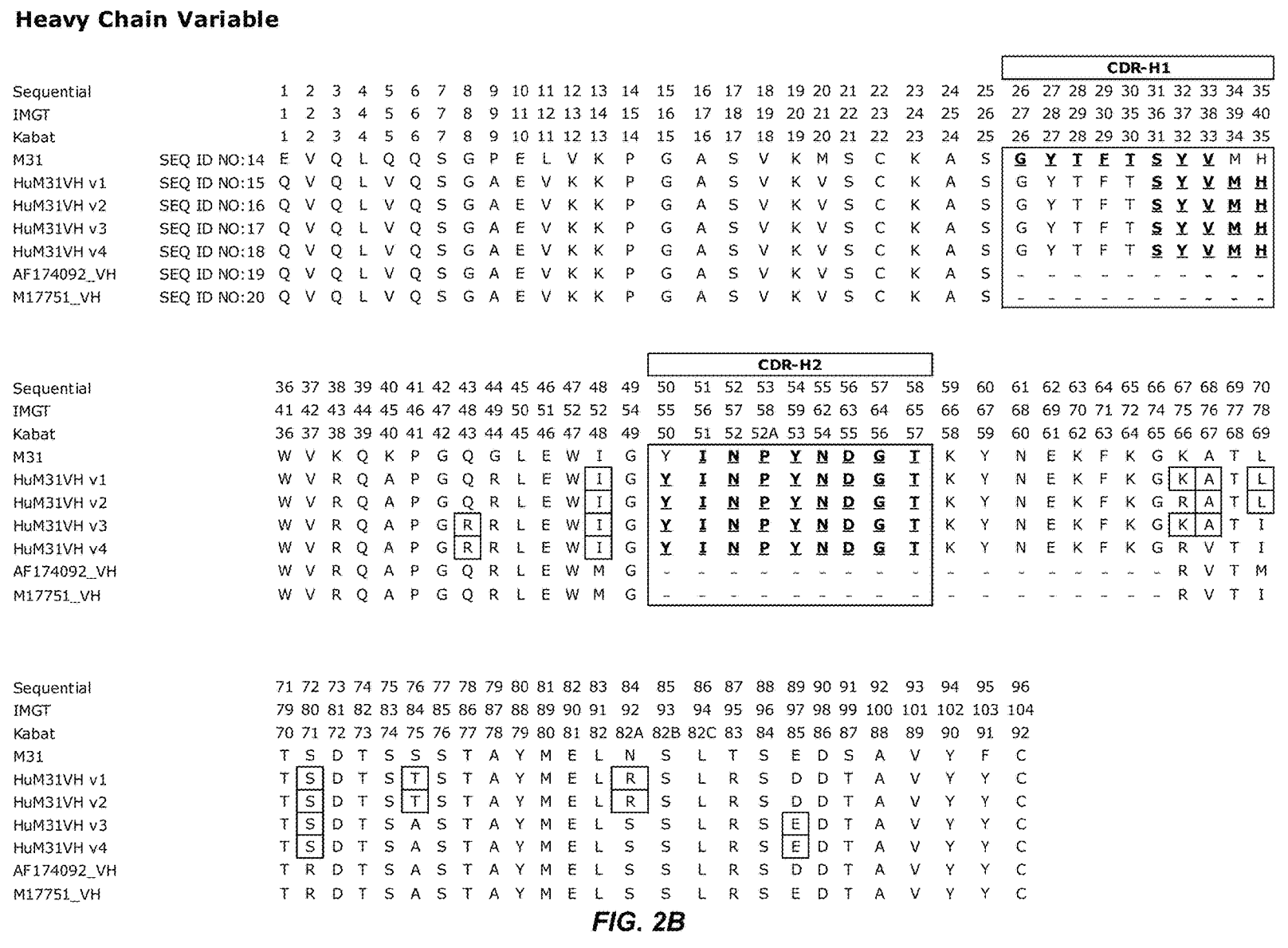

FIGS. 2A, 2B and 2C show a comparison of various humanized M31 antibodies, showing the HVR sequences shaded (light or dark gray) and bolded underline, along with numbering in sequential, IMGT and Kabat formats. Positions in which a human amino acid is replaced with a corresponding mouse amino acid are boxed. FIG. 2A shows the variable light chain sequences of (i) murine M31 (SEQ ID NO:10), (ii) humanized HuM31VL_v1 (SEQ ID NO:11), HuM31VL_v2 (SEQ ID NO:12) and (iii) X02990VL human donor sequence (SEQ ID NO:13). The variable light chain sequence of M31 can also be represented by the following:

```
SEQ ID NO: 25
Light chain M31 (CDRS
bold and underlined, different
options at a position are shown in
parentheses)
D I        V M T Q        S P D S L A V
  S        L G E R        A T I N C
- R        A S E S        V D S Y G N S
  F        M H W Y        Q Q K P G Q P
  P        K L L I        Y L A S N L E
  S        G V P (A/D)    R F S G S G S
  (G/R)    T D F T        L T I D P V E
  A        D D A A        T Y Y C Q Q N
  N        Y D P W        T F G G G T K
  L        E I K.
```

FIGS. 2B and 2C show the variable heavy chain sequences of (i) murine M31 (SEQ ID NO:14), (ii) humanized HuM31VH_v1 (SEQ ID NO:15), HuM31VH_v2 (SEQ ID NO:16), HuM31VH_v3 (SEQ ID NO:17), HuM31VH_v4 (SEQ ID NO:18), and (iii) the human donor sequence AF174092 VH (SEQ ID NO:19) and M17751 VH (SEQ ID NO:20). The variable heavy chain sequence of M31 can also be represented by the following:

```
SEQ ID NO: 26
Heavy chain humanized M31 based on modified human framework AF174092_VH
(CDRS bold and underlined, different options at a position are shown in
parentheses)
Q V Q L     V   Q   S       G       A       E       V       K       K
P G A       S   V   K       V       S       C       K       A       S
G Y T       F   T   S       Y       V       M       H       W       V
R Q A       P   G   (Q/R)   R       L       E       W       I       G
Y I N       P   Y   N       D       G       T       K       Y       N
E K F       K   G   (R/K)   (V/A)   T       (L/I)   T       S       D
T S (A/T)   S   T   A       Y       M       E       L       (S/R)   S
L R S       (D/E) D T       A       V       Y       Y       C       A
R P I       Y   F   D       N       D       Y       F       D       Y
W G Q       G   T   (L/T)   V       T       V       S       S.
```

```
SEQ ID NO: 27
Heavy chain humanized M31 based on modified human
framework M17751_VH (CDRS bold and underlined,
different options at a position are shown in
parentheses)
Q V Q L     V   Q S       G       A E     V K     K
P G A       S   V K       V       S C     K A     S
G Y T       F   T S       Y       V M     H W     V
R Q A       P   G (Q/R)   R       L E     W (M/I) G
Y I N       P   Y N       D       G T     K Y     N
E K F       K   G (R/K)   (V/A)   T (I/L) T S     D
T S (A/T)   S   T A       Y       M E     L (S/R) S
L R S       (E/D) D T     A       V Y     Y C     A
R P I       Y   F D       N       D Y     F D     Y
W G Q       G   T (L/T)   V       T V     S S.
```

FIG. 3 is a plot of binding intensity of various M26 antibodies in 293 cells transiently expressing CLL-1. Also shown are the $EC_{50}$ values and mean fluorescent intensity (MFI). Antibodies shown are chimeric M26 (human constant, mouse variable), HuM26 with VH4A heavy chain (SEQ ID NO:8) and L4 (SEQ ID NO:3), L4D (SEQ ID NO:4), L4DR (SEQ ID NO:5) relative to IgG control.

Figure 4:
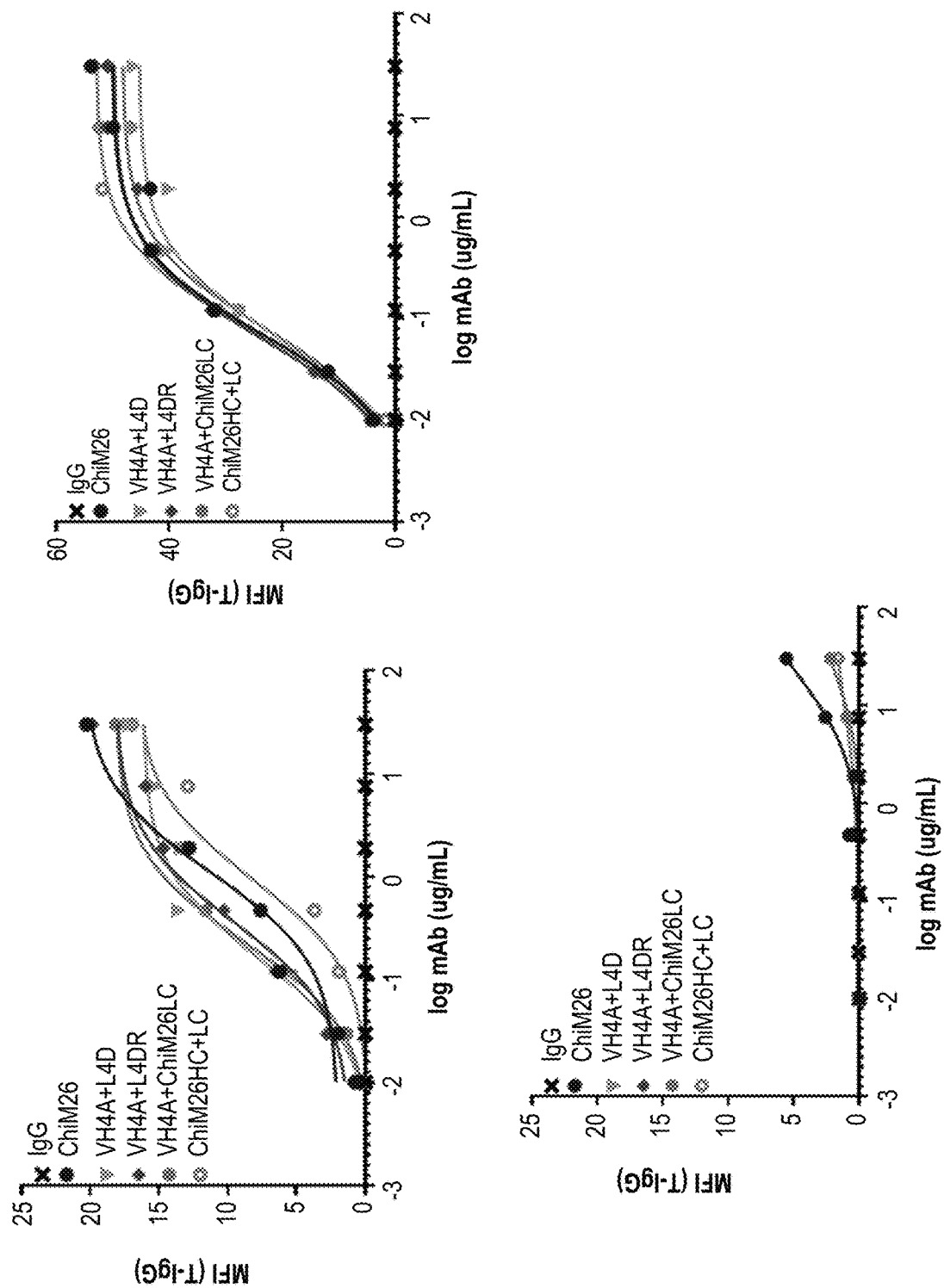

FIG. 4 is a plot of binding intensity of various M26 antibodies in various cell lines (i.e., HL-60, OCI-AML-5, OCI-AML-5 knock/out). Antibodies shown are chimeric M26 HuM26 with VH4A heavy chain (SEQ ID NO:8) and L4 (SEQ ID NO:3) and L4DR (SEQ ID NO:5) and chimeric M26 light chain and chimeric M26 heavy chain and light chain relative to IgG control.

Figure 5:
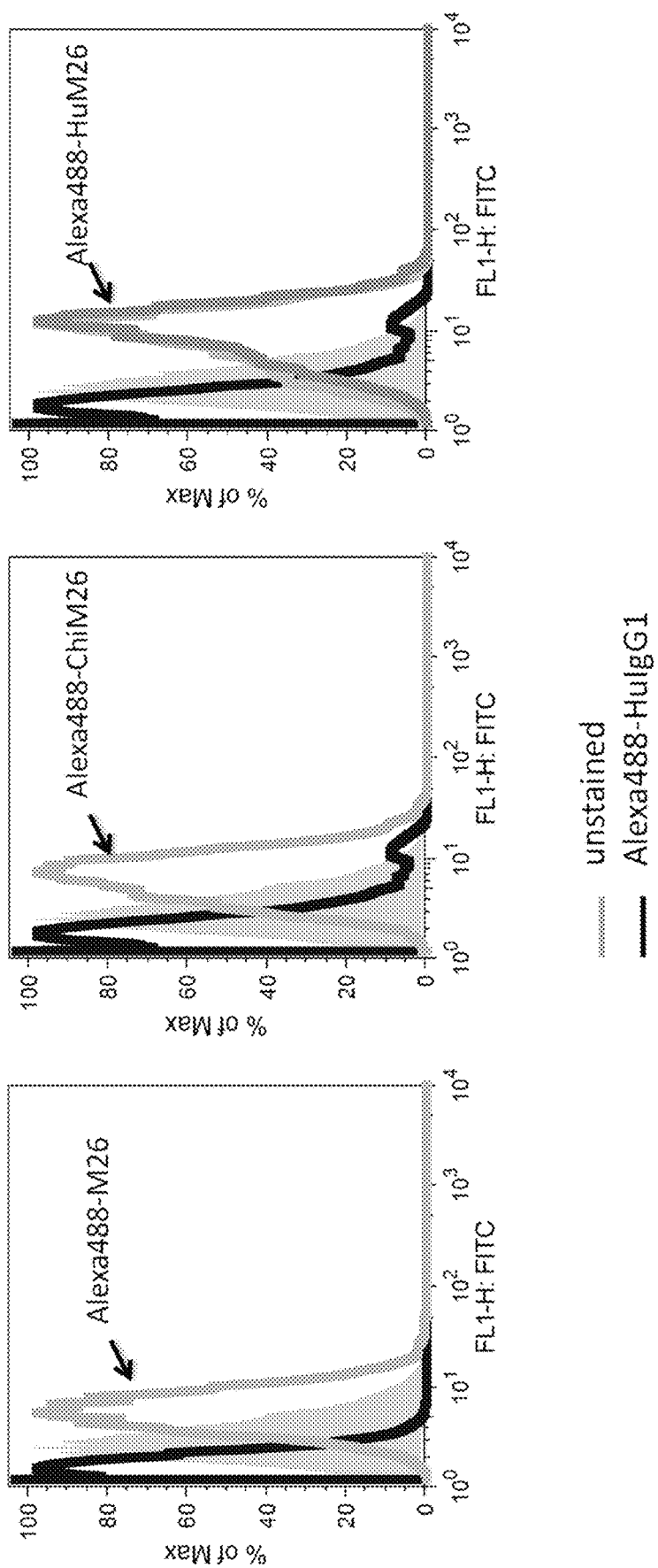

FIG. 5 are overlay histogram plots of binding on rhesus MPC cells of M26, chimeric M26 and humanized M26. (Black=IgG, Dark gray=HuM26, Light grayok=Chimeric M26.) This shows that chimeric M26 and humanized M26 has similar binding profiles.

Figure 6:
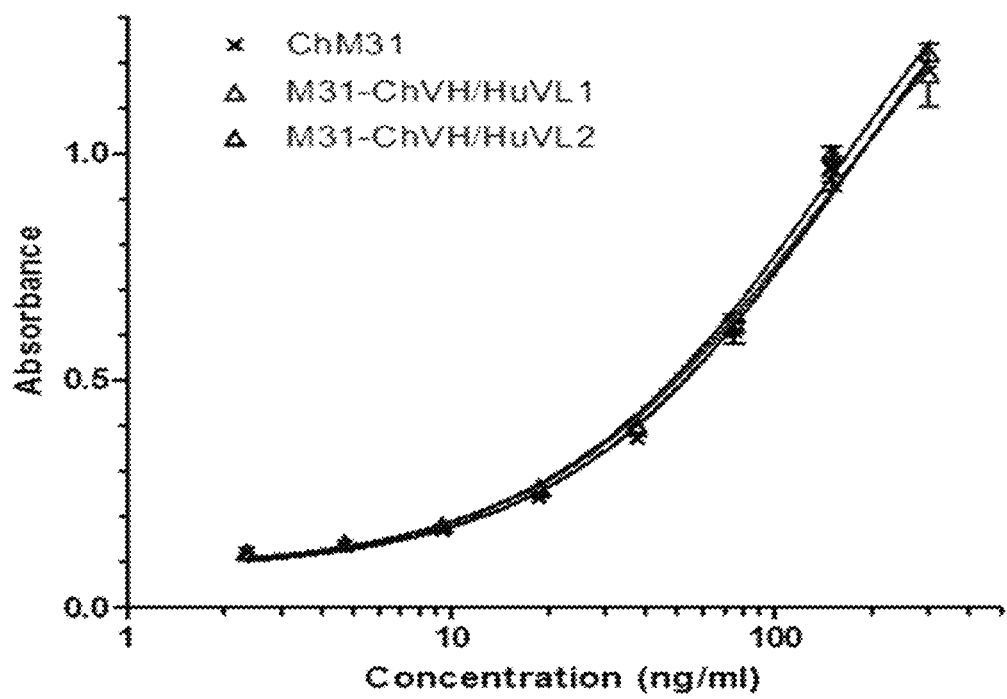

FIG. 6 is an ELISA analysis of the binding of transiently expressed ChM31 (chimeric—M31), M31-ChVH/HuVL1 (SEQ ID NO:14/SEQ ID NO:11) and M31-ChVH/HuVL2 (SEQ ID NO:14/SEQ ID NO:12) antibodies to CLL-bearing a His Tag antigen. Each antibody was tested at various concentrations, starting at 250 ng/ml and serial 2-fold dilutions. Absorbance values (Y-axis) are plotted at each antibody concentration tested (X-axis) in the figure.

Figure 7:
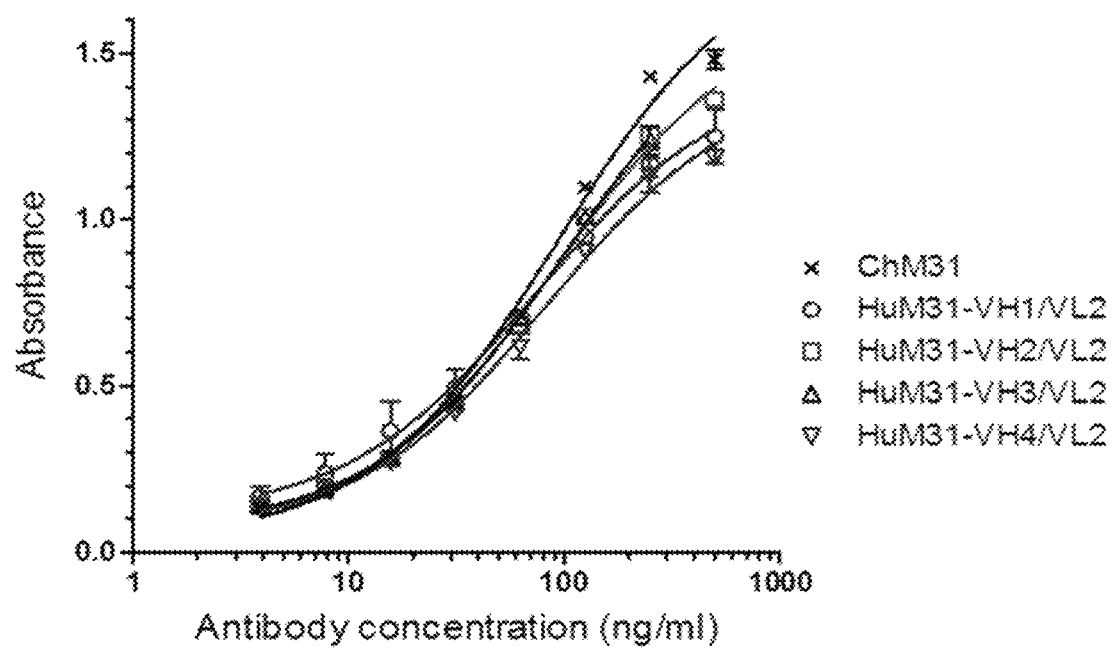

FIG. 7 is an ELISA analysis of the binding of transiently expressed ChM31 (SEQ ID NO:14/SEQ ID NO:10), HuM31-VH1/VL2 (SEQ ID NO:15/SEQ ID NO:12), HuM31-VH2/VL2 (SEQ ID NO:16/SEQ ID NO:12), HuM31-VH3/VL2 (SEQ ID NO:17/SEQ ID NO:12), and HuM31-VH4/VL2 (SEQ ID NO:18/SEQ ID NO:12), antibodies to CLL-1 bearing a His Tag. Each antibody was tested at various concentrations, starting at 500 ng/ml and serial 2-fold dilutions. Absorbance values (Y-axis) are plotted at each antibody concentration tested (X-axis) in the figure.

Figure 8:
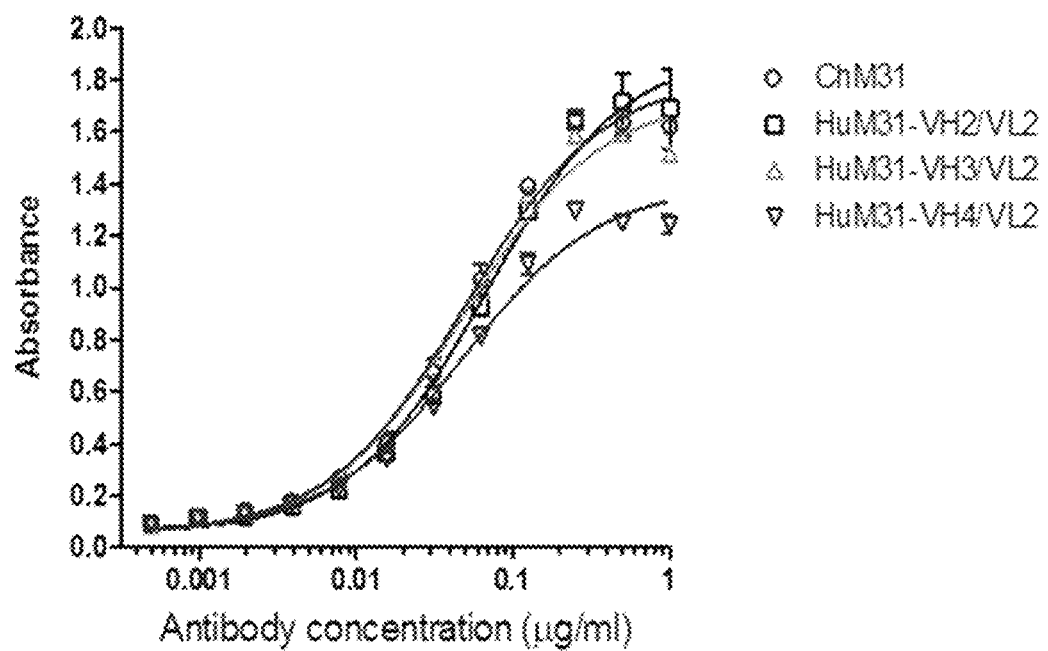

FIG. 8 is an ELISA analysis of the binding of purified ChM31 (SEQ ID NO:14/SEQ ID NO:10), HuM31-VH2/VL2 (SEQ ID NO:16/SEQ ID NO:12), HuM31-VH3/VL2 (SEQ ID NO:17/SEQ ID NO:12), and HuM31-VH4/VL2 (SEQ ID NO:18/SEQ ID NO:12), antibodies to CLL-1 bearing a His Tag. Each antibody was tested at various concentrations, starting at 1 μg/ml and serial 2-fold dilutions. Absorbance values (Y-axis) are plotted at each antibody concentration tested (X-axis) in the figure.

Figure 9:
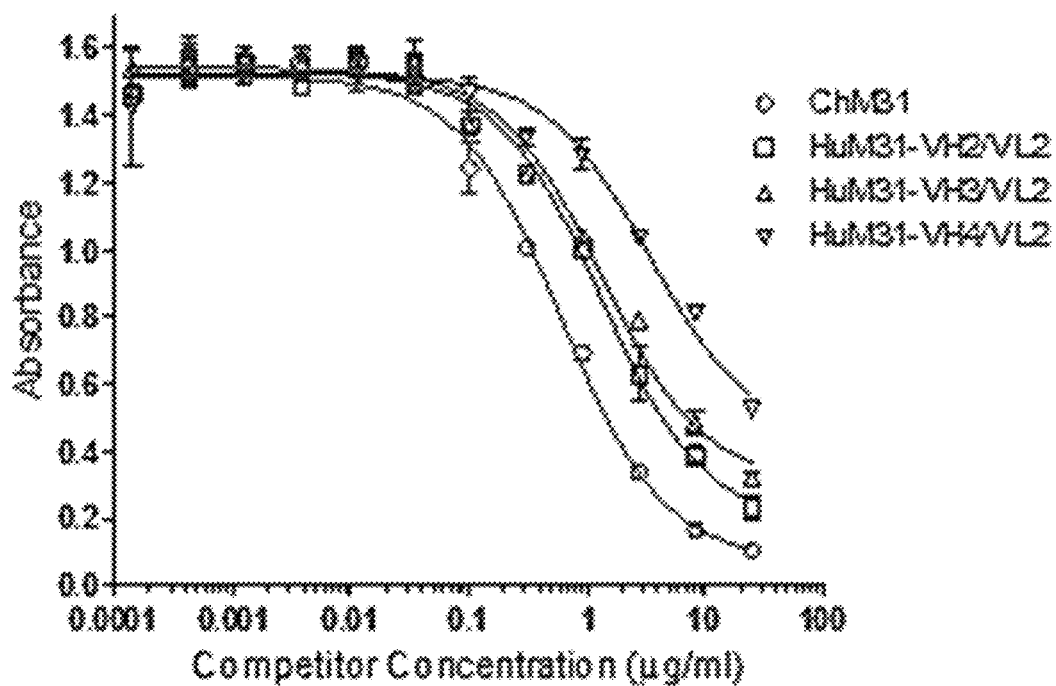

FIG. 9 is an ELISA analysis of competitive binding affinity of ChM31 (SEQ ID NO:14/SEQ ID NO:10), HuM31-VH1/VL2 (SEQ ID NO:15/SEQ ID NO:12), HuM31-VH2/VL2 (SEQ ID NO:16/SEQ ID NO:12), HuM31-VH3/VL2 (SEQ ID NO:17/SEQ ID NO:12), and HuM31-VH4/VL2 (SEQ ID NO:18/SEQ ID NO:12), antibodies to CLL-1 bearing a His Tag. Binding of mouse M31 antibody in the presence of ChM31, HuM31-VH2/VL2, HuM31-VH3/VL2 or HuM31-VH4/VL2 antibody, starting at 25 μg/ml and serial 3-fold dilutions, was analyzed. Absorbance values (Y-axis) are plotted at each antibody concentration tested (X-axis) in the figure. $IC_{50}$ values were calculated using GraphPad Prism.

Figure 10:
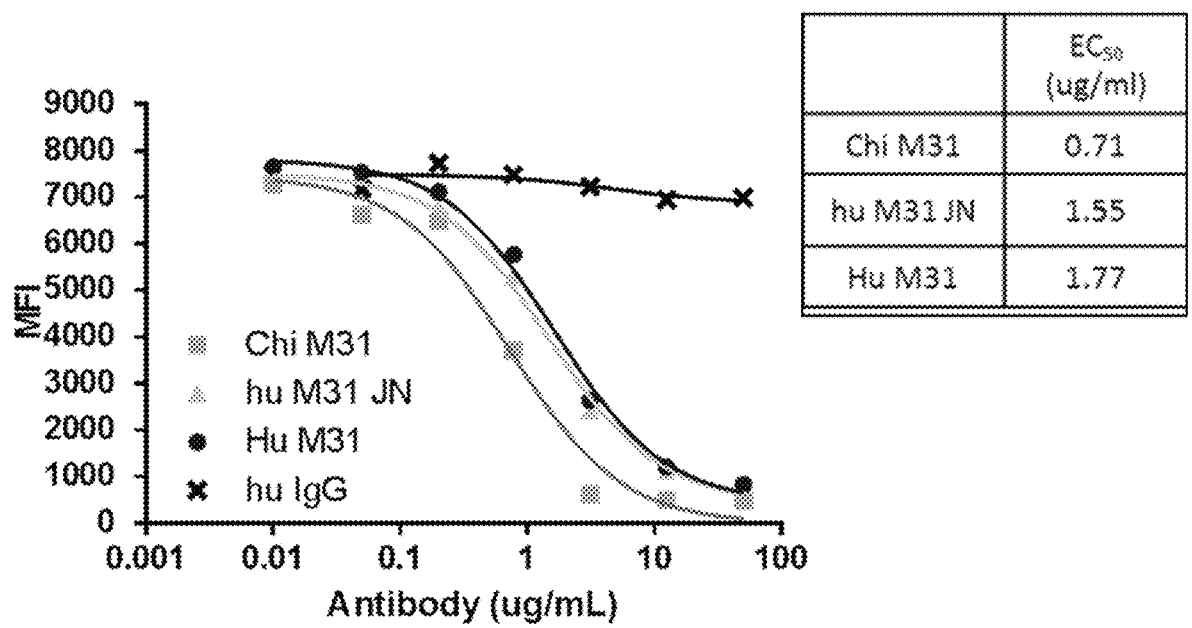

FIG. 10 is an ELISA analysis of competitive binding to 293CLL1 cells. ChiM31 was labelled with Alex488. Binding of ChiM31-Alex488 antibody in the presence of ChiM31, HuM31 and mouse M31 starting at 30 μg/ml and serial 3-fold dilutions, was analyzed. Absorbance values MFI (Y-axis) are plotted at each antibody concentration tested (X-axis) in the figure. $IC_{50}$ values were calculated using GraphPad Prism.

Figure 11:
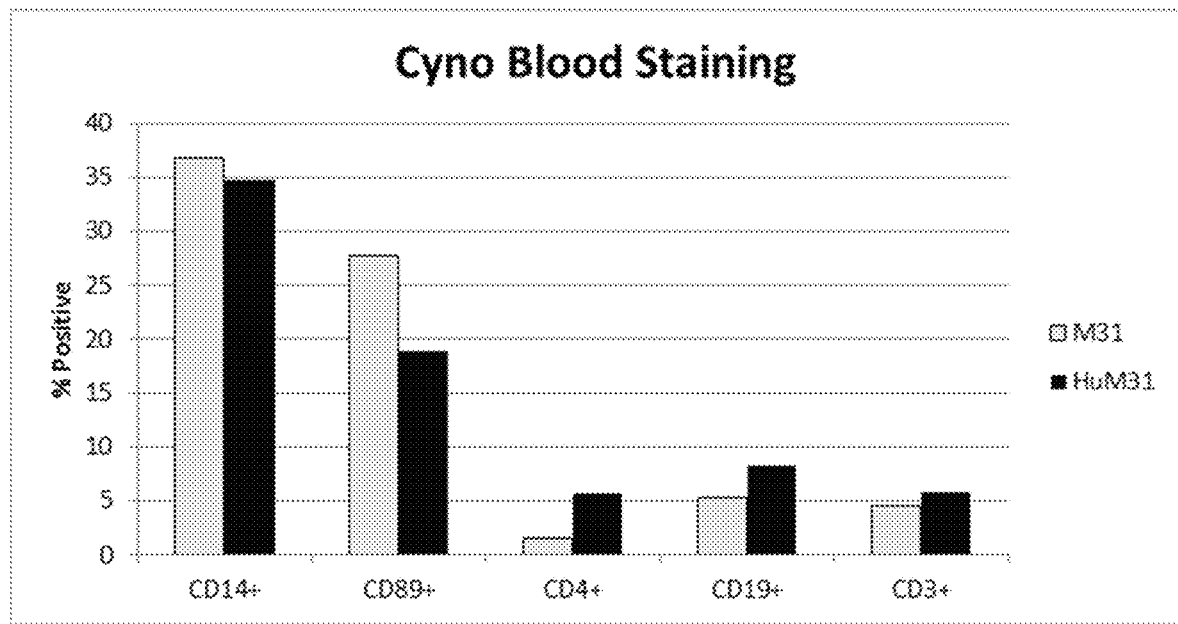
Figure 12A:
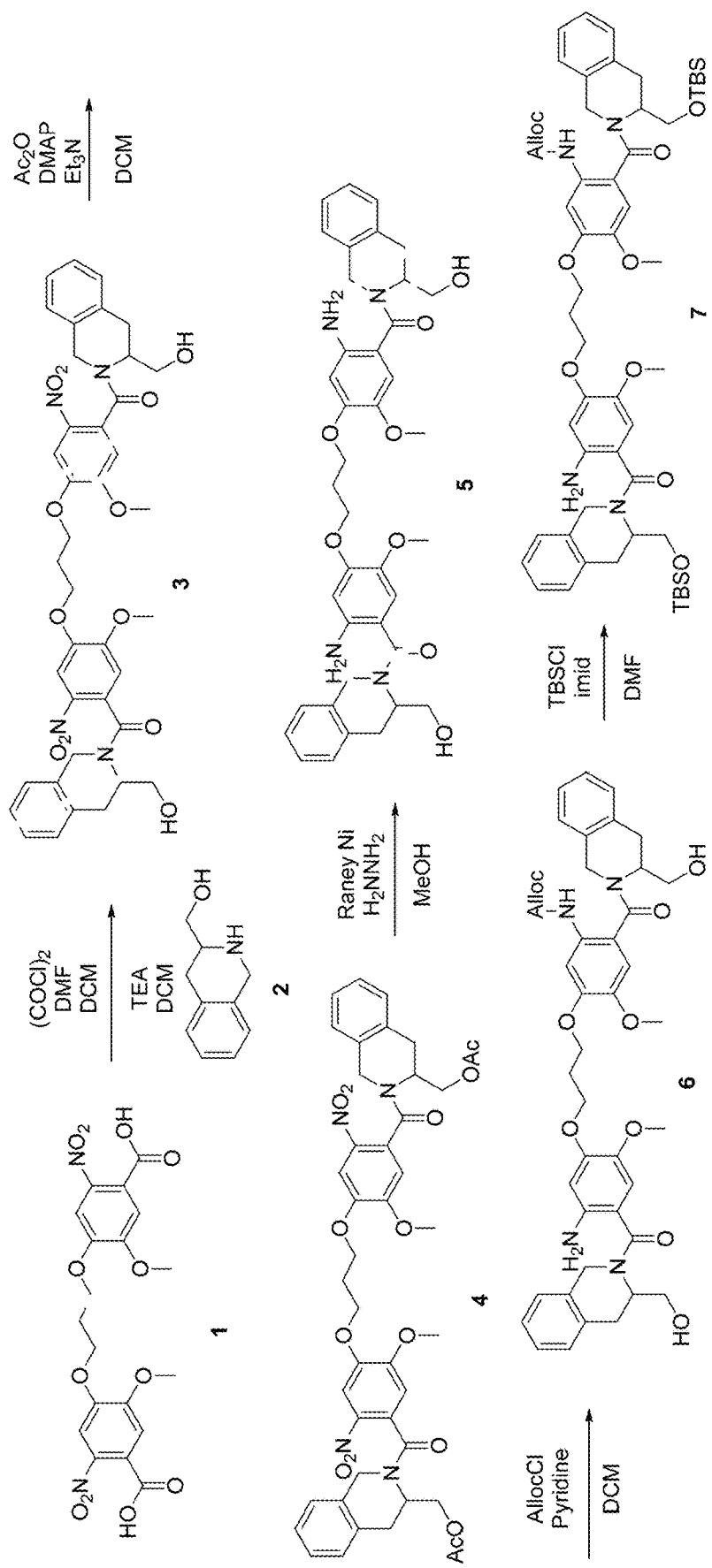
Figure 12B:
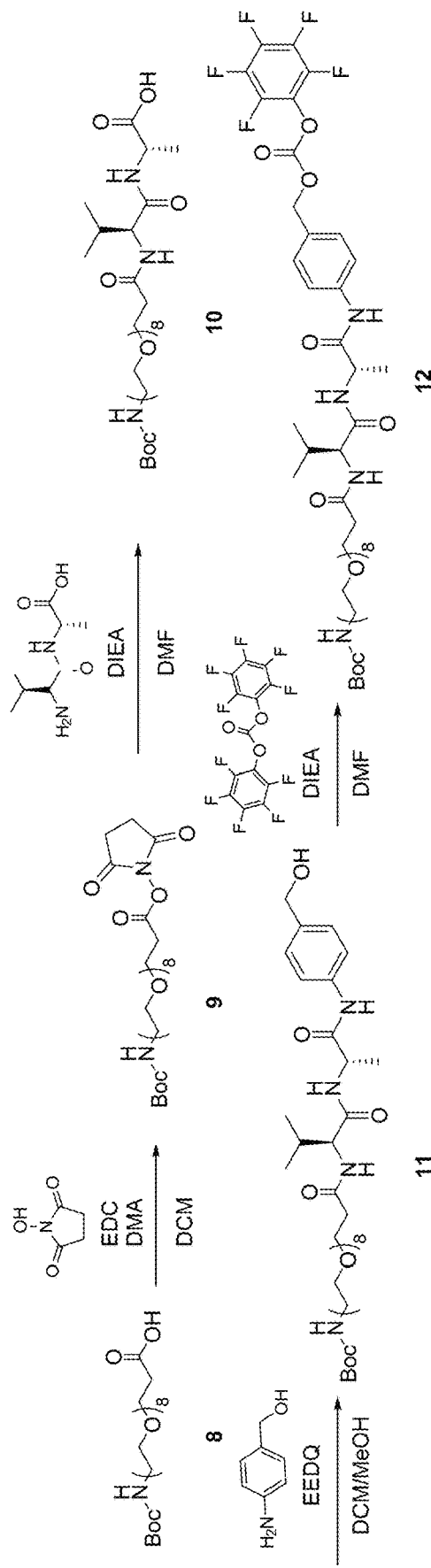
Figure 12C:
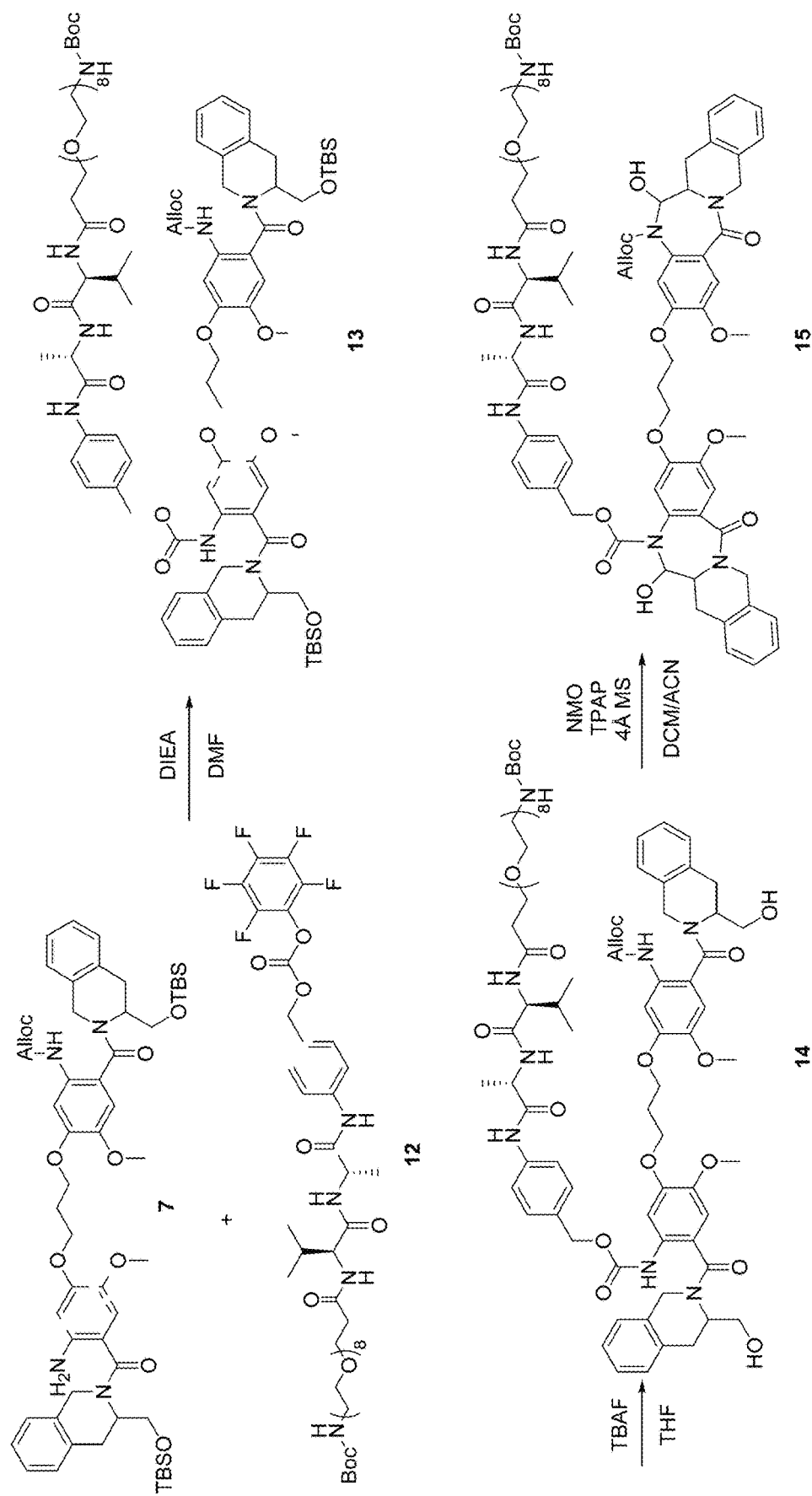
Figure 12D:
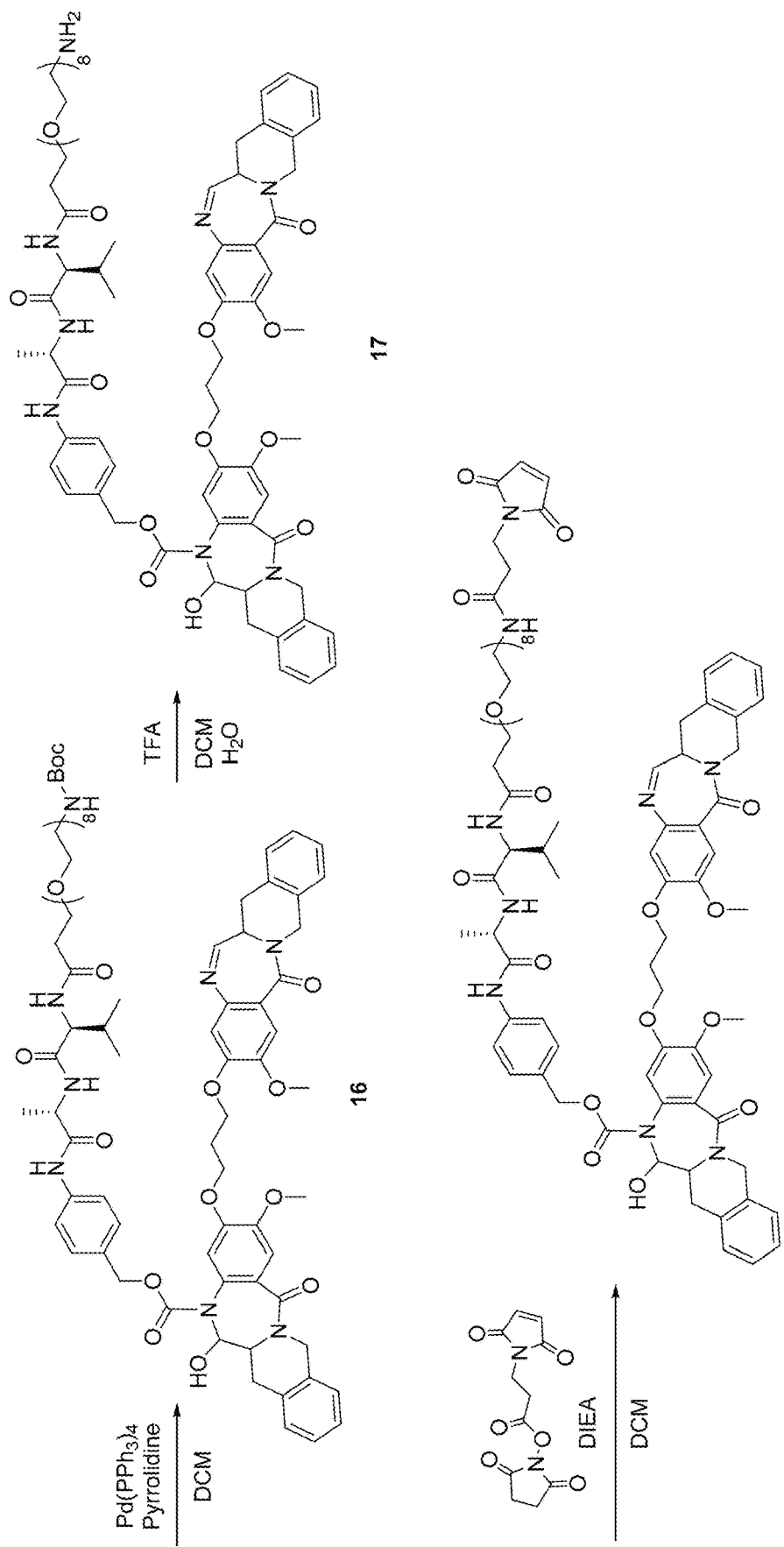

FIG. 11 is a histogram showing binding on various markers on cynomolgus monkey cell markers relative to murine v. humanized anti-M31 antibodies.

FIGS. 12A, 12B, 12C and 12D show a synthesis scheme for CLT-D202.

FIG. 13 shows target dependent cell killing of an anti-CLL1-D202 conjugate.

FIGS. 14A and 14B show a CLL1-ADC displayed target dependent cell killing in MDR+ve cell line.

Figure 15:
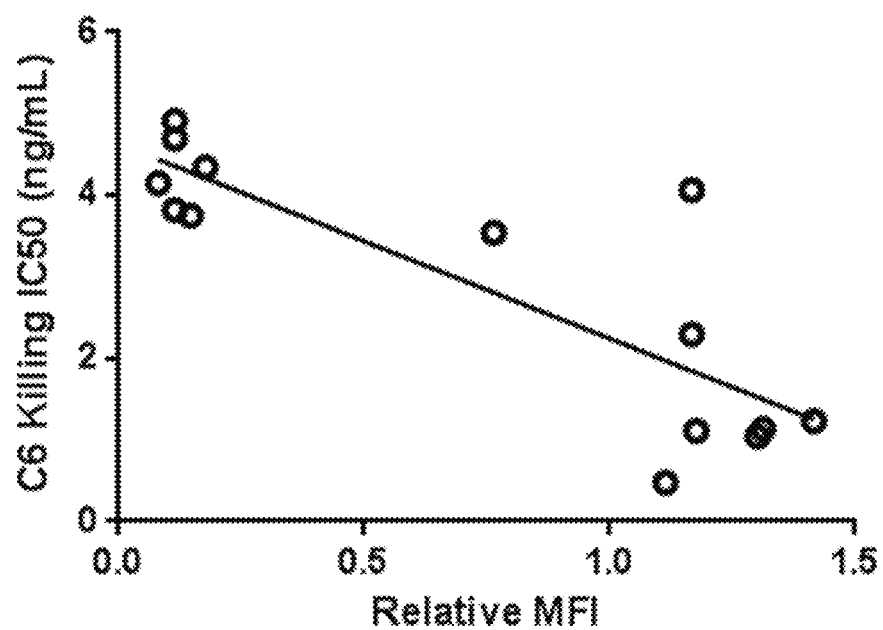

FIG. 15 shows a comparison of killing and binding of a CLL1-ADC.

Figure 16:
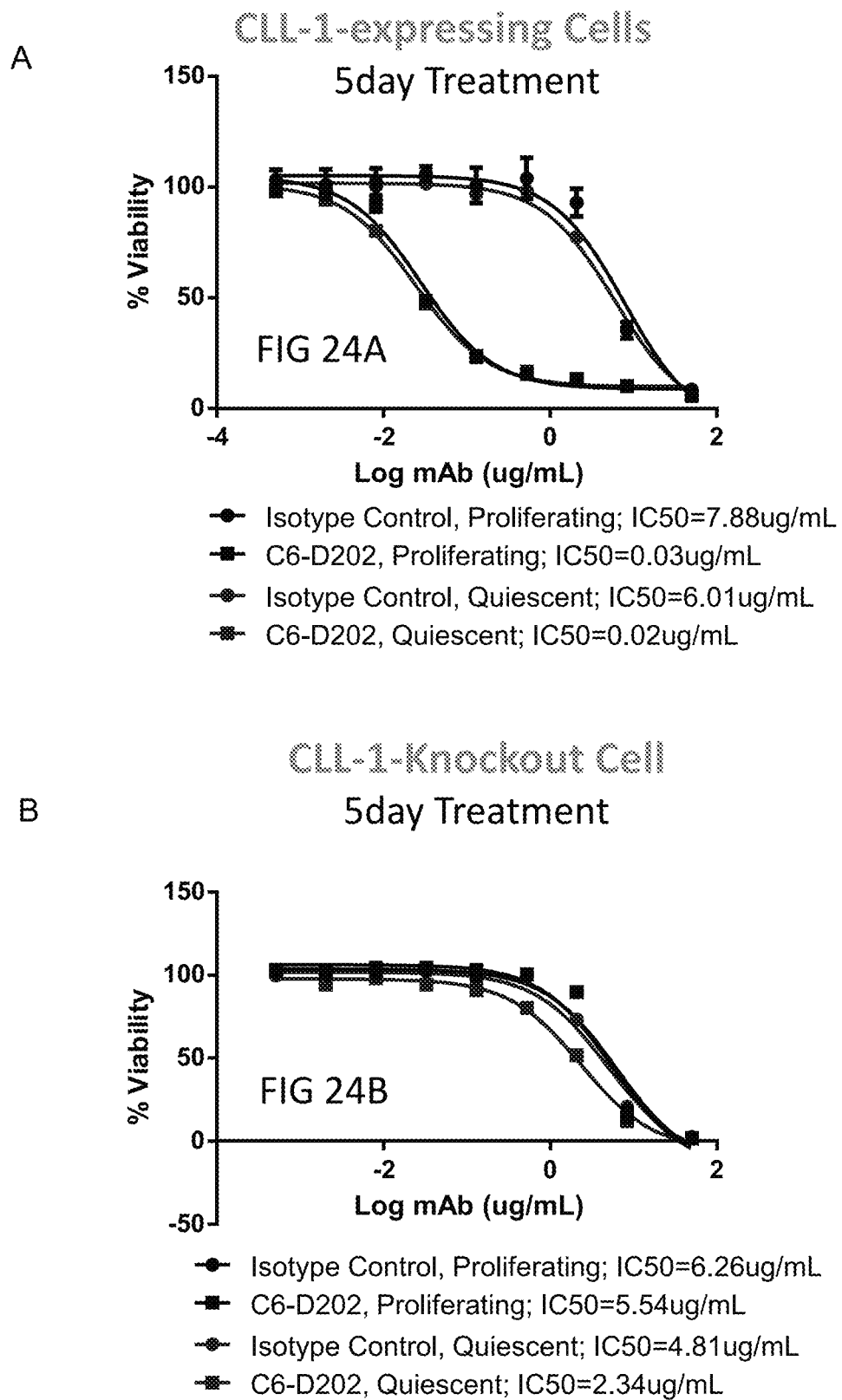

FIGS. 16A and 16B show that a CLL1-ADC kills both quiescent and proliferating cells.

DETAILED DESCRIPTION OF THE INVENTION

I. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989). The term "a" or "an" is intended to mean "one or more." The term "comprise" and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

C-type Lectin-Like molecule 1 (CLL-1), also known as CLEC12A, DCAL-2, and MICL, is a type II membrane protein (ITIM domain—TM domain-stalk domain-lectin-like domain). The extracellular domain of CLL-1 is highly glycosylated, and it is expressed exclusively in cells of myeloid lineage. CLL-1 is also expressed on AML, MDS, and CML cells. CLL-1 expression can be used to distinguish between normal hematopoietic stem cells (HSCs), which do not express CLL-1, and leukemic stem cells (LSCs), where it is expressed. LSCs are CD34+ cells in leukemia patients that lead to production of cancer cells and recurrence of cancer. See Bakker et al. (2004) *Cancer Res.* 64:8443.

The nucleotide and protein sequences of CLL-1 are known for many species. For example, the human sequences can be found at Genbank accession number AF247788.1 (coding sequence shown in SEQ ID NO:1) and Uniprot accession number Q5QGZ9 (SEQ ID NO:2). For the human CLL-1 protein shown as SEQ ID NO:2, the extracellular domain comprises approximately amino acids 65-265, the transmembrane domain comprises approximately amino acids 44-64, and the cytoplasmic domain comprises approximately amino acids 1-43. The stalk domain of human CLL-1 spans amino acids 65-139, and the C lectin domain spans amino acids 140-249, both with reference to the sequence shown in SEQ ID NO:2. One of skill will understand that CLL-1 variants (e.g., species homologs, allelic variants, etc.) can be optimally aligned, e.g., for identification of conserved residues and domains.

The terms "CLL-1 specific antibody," "anti-CLL-1 antibody," "CLL-1 antibody," and "anti-CLL-1" are used synonymously herein to refer to an antibody that specifically binds to CLL-1, including variously glycosylated forms of CLL-1. The CLL-1 antibodies described herein specifically bind the CLL-1 polypeptide expressed, e.g., on the surface of certain cancer cells, but not to HSCs. As discussed in more detail below, the present anti-CLL-1 antibodies can bind CLL-1 expressing cells, bind a larger percentage of AML cells compared to other AML-targeting antibodies, inhibit AML cell proliferation, and mediate their destruction.

A "CLL-1 associated disorder" (or "CLL-1 related disorder", "CLL-1 disorder", "CLL-1 related condition or disease", etc.) refers to conditions and diseases correlated with elevated or reduced cell surface expression of CLL-1 as compared to CLL-1 expression in a standard control (e.g., a normal, non-disease, non-cancer cell). Elevated CLL-1 levels are associated with cancer cells, in particular, leukemias such as AML (acute myelogenous leukemia), MDS (myelodysplastic syndrome), and CML (chronic myelogenous leukemia), and in hematopoietic CSCs (e.g., LSCs).

The term "antibody" refers to a polypeptide structure, e.g., a whole immunoglobulin (two light chains and two heavy chains, e.g., a tetramer), an immunoglobulin polypeptide (a light chain or a heavy chain) a conjugate, or fragment thereof that retains antigen binding activity. The term includes but is not limited to polyclonal or monoclonal antibodies of the isotype classes IgA, IgD, IgE, IgG, and IgM, derived from human or other mammalian cells, including natural or genetically modified forms such as humanized, human, single-chain, chimeric, synthetic, recombinant, hybrid, mutated, grafted, and in vitro generated antibodies. The term encompasses conjugates, including but not limited to fusion proteins containing an immunoglobulin moiety (e.g., chimeric or bispecific antibodies or scFv's), and fragments, such as Fab, F(ab')2, Fv, scFv, Fd, dAb and other compositions.

The term "chimeric antigen receptor" or "CAR" refers to a polypeptide comprising (1) a target binding domain (e.g., a binding portion of an antibody, such as scFV); (2) a hinge region; (3) a transmembrane domain (TM); and (4) an intracellular domain comprising at least one signal transduction domain (e.g., CD4).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these regions of the light and heavy chains respectively. The variable region contains the antigen-binding region of the antibody (or its functional equivalent) and is most critical in specificity and affinity of binding. See Paul, *Fundamental Immunology* (2003).

Antibodies can exist as intact immunoglobulins or as any of a number of well-characterized fragments that include specific antigen-binding activity. For the sake of clarity, a tetrameric antibody with heavy and light chains is referred to herein as an "intact immunoglobulin," and can be naturally occurring, polyclonal, monoclonal, or recombinantly produced. Fragments can be produced by digestion with various peptidases. Pepsin digests an antibody below the disulfide linkages in the hinge region to produce F(ab')2, a dimer of Fab which itself is a light chain joined to $V_H$-$C_H$1 by a disulfide bond. The F(ab')2 may be reduced under mild conditions to break the disulfide linkage in the hinge region, thereby converting the F(ab')$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies or those identified using phage display libraries (see, e.g., McCafferty et al., *Nature* 348: 552-554 (1990)).

As used herein, the term "Fv" refers to a monovalent or bi-valent variable region fragment, and can encompass only the variable regions (e.g., $V_L$ and/or $V_H$), as well as longer fragments, e.g., an Fab, Fab' or F(ab')2, which also includes CL and/or $C_H1$. Unless otherwise specified, the term "Fc" refers to a heavy chain monomer or dimer comprising $C_H1$ and $C_H2$ regions.

A single chain Fv (scFv) refers to a polypeptide comprising a $V_L$ and $V_H$ joined by a linker, e.g., a peptide linker. ScFvs can also be used to form tandem (or di-valent) scFvs or diabodies. Production and properties of tandem scFvs and diabodies are described, e.g., in Asano et al. (2011) *J Biol. Chem.* 286:1812; Kenanova et al. (2010) *Prot Eng Design Sel* 23:789; Asano et al. (2008) *Prot Eng Design Sel* 21:597.

As used herein "monoclonal antibody" refers to a clonal preparation of antibodies with a single binding specificity and affinity for a given epitope on an antigen.

A "polyclonal antibody" refers to a preparation of antibodies that are raised against a single antigen, but with different binding specificities and affinities.

As used herein, "V-region" refers to an antibody variable region domain comprising the segments of Framework 1, CDR1, Framework 2, CDR2, and Framework 3, including CDR3 and Framework 4, which segments are added to the V-segment as a consequence of rearrangement of the heavy chain and light chain V-region genes during B-cell differentiation.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, (1987) *J Mol. Biol.* 196, 901-917; Chothia et al. (1989) Nature 342, 877-883; Chothia et al. (1992) J. Mol. Biol. 227, 799-817; Al-Lazikani et al., *J. Mol. Biol* 1997, 273(4)). A helpful guide for locating CDRs using the Kabat system can be found at the website available at bioinforg.uk/abs. Definitions of antigen combining sites are also described in the following: Ruiz et al. *Nucleic Acids Res.*, 28, 219-221 (2000); and Lefranc *Nucleic Acids Res*. January 1; 29(1):207-9 (2001); MacCallum et al. *J. Mol. Biol.*, 262: 732-745 (1996); and Martin et al, *Proc. Natl Acad. Sci. USA*, 86, 9268-9272 (1989); Martin, et al, *Methods Enzymol.*, 203: 121-153, (1991); Pedersen et al, *Immunomethods*, 1, 126, (1992); and Rees et al, In Sternberg M. J. E. (ed.), Protein Structure Prediction. Oxford University Press, Oxford, 141-172 1996).

A "chimeric antibody" refers to an antibody in which (a) the constant region, or a portion thereof, is altered, replaced or exchanged so that the antigen binding site (variable region, CDR, or portion thereof) is linked to a constant region of a different or altered class, effector function and/or species; or (b) the variable region, or a portion thereof, is altered, replaced or exchanged with a variable region having a different or altered antigen specificity (e.g., CDR and framework regions from different species). Chimeric antibodies can include variable region fragments, e.g., a recombinant antibody comprising two Fab or Fv regions or an scFv. A chimeric can also, as indicated above, include an Fc region from a different source than the attached Fv regions. In some cases, the chimeric antibody includes chimerism within the Fv region. An example of such a chimeric antibody would be a humanized antibody where the framework regions and CDRs are from different sources.

Humanized antibodies are antibodies in which the antigen binding loops, i.e., CDRs, obtained from the $V_H$ and $V_L$ regions of a non-human antibody are grafted to a human framework sequence. Humanization, i.e., substitution of non-human CDR sequences for the corresponding sequences of a human antibody, can be performed following the methods described in, e.g., U.S. Pat. Nos. 5,545,806; 5,569,825; 5,633,425; 5,661,016; Riechmann et al., *Nature* 332:323-327 (1988); Marks et al., *Bio/Technology* 10:779-783 (1992); Morrison, *Nature* 368:812-13 (1994); Fishwild et al., *Nature Biotechnology* 14:845-51 (1996). Transgenic mice, or other organisms such as other mammals, may also be used to express humanized or human antibodies, as disclosed in U.S. Pat. No. 6,673,986.

The terms "antigen," "immunogen," "antibody target," "target analyte," and like terms are used herein to refer to a molecule, compound, or complex that is recognized by an antibody, i.e., can be specifically bound by the antibody. The term can refer to any molecule that can be specifically recognized by an antibody, e.g., a polypeptide, polynucleotide, carbohydrate, lipid, chemical moiety, or combinations thereof (e.g., phosphorylated or glycosylated polypeptides, etc.). One of skill will understand that the term does not indicate that the molecule is immunogenic in every context, but simply indicates that it can be targeted by an antibody.

Antibodies bind to an "epitope" on an antigen. The epitope is the localized site on the antigen that is recognized and bound by the antibody. Epitopes can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope). The same is true for other types of target molecules that form three-dimensional structures.

The terms "specific for," "specifically binds," and like terms refer to a molecule (e.g., antibody or antibody fragment) that binds to a target with at least 2-fold greater affinity than non-target compounds, e.g., at least any of 4-fold, 5-fold, 6-fold, 7-fold, 8-fold, 9-fold, 10-fold, 20-fold, 25-fold, 50-fold, or 100-fold greater affinity. For example, an antibody that specifically binds a primary antibody will typically bind the primary antibody with at least a 2-fold greater affinity than a non-primary antibody target (e.g., an antibody from a different species or of a different isotype, or a non-antibody target).

The term "captures" with respect to an antibody target (e.g., antigen, analyte, immune complex), typically indicates that an antibody binds a majority of the antibody targets in a pure population (assuming appropriate molar ratios). For example, an antibody that binds a given antibody target typically binds to at least ⅔ of the antibody targets in a solution (e.g., at least any of 75, 80, 85, 90, 91, 92, 93, 94, 95, 96, 97, 98, 99, or 100%). One of skill will recognize that some variability will arise depending on the method and/or threshold of determining binding.

The term "cross-linked" with respect to an antibody refers to attachment of the antibody to a solid or semisolid matrix (e.g., sepharose, beads, culture plate), or to another protein or antibody. For example, the antibody can be multimerized to create an antibody complex with multiple (more than 2) antigen-binding sites. The antibody can be multimerized by expressing the antibody as a high-valency isotype (e.g., IgA or IgM, which typically form complexes of 2 or 5 antibodies, respectively). Antibody multimerization can also be carried out by using a cross-linker comprising a reactive group capable of linking proteins (e.g., carbodiimide, NHS esters, etc.). Methods and compositions for cross-linking an antibody to a matrix are described, e.g., in the Abcam and New England Biolab catalogs and websites (available at abcam.com and neb.com). Cross-linker compounds with various reactive groups are described, e.g., in Thermo Fisher Scientific catalog and website (available at piercenet.com).

The term "cysteine substituted antibody," as used herein, refers to an antibody comprising at least one constant region immunoglobulin amino acid residue that has been substituted with a non-naturally occurring cysteine. A non-naturally occurring substitution is one that is not isotypic. In one embodiment, the substituted residues are heavy chain constant regions residues T153C, S156C, V266C, H285C, R301C, V303C, T307C, G316C, Y436C and L441C. In some embodiments, the constant region is of isotype IgG1, IgG2, IgG3 or IgG4.

As used herein, a first antibody, or an antigen-binding portion thereof, "competes" for binding to a target with a second antibody, or an antigen-binding portion thereof, when binding of the second antibody with the target is detectably decreased in the presence of the first antibody compared to the binding of the second antibody in the absence of the first antibody. The alternative, where the binding of the first antibody to the target is also detectably decreased in the presence of the second antibody, can, but need not be the case. That is, a second antibody can inhibit the binding of a first antibody to the target without that first antibody inhibiting the binding of the second antibody to the target. However, where each antibody detectably inhibits the binding of the other antibody to its cognate epitope or ligand, whether to the same, greater, or lesser extent, the antibodies are said to "cross-compete" with each other for binding of their respective epitope(s). Both competing and cross-competing antibodies are encompassed by the present invention. The term "competitor" antibody can be applied to the first or second antibody as can be determined by one of skill in the art. In some cases, the presence of the competitor antibody (e.g., the first antibody) reduces binding of the second antibody to the target by at least 10%, e.g., at least any of 20%, 30%, 40%, 50%, 60%, 70%, 80%, or more, e.g., so that binding of the second antibody to target is undetectable in the presence of the first (competitor) antibody.

The terms "label," "detectable moiety," and like terms refer to a composition detectable by spectroscopic, photochemical, biochemical, immunochemical, chemical, or other physical means. For example, useful labels include fluorescent dyes, luminescent agents, radioisotopes (e.g., $^{32}$P, $^{3}$H), electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target analyte. Any method known in the art for conjugating an antibody to the label may be employed, e.g., using methods described in Hermanson, *Bioconjugate Techniques* 1996, Academic Press, Inc., San Diego. The term "tag" can be used synonymously with the term "label," but generally refers to an affinity-based moiety, e.g., a "His tag" for purification, or a "streptavidin tag" that interacts with biotin.

A "labeled" molecule (e.g., nucleic acid, protein, or antibody) is one that is bound, either covalently, through a linker or a chemical bond, or noncovalently, through ionic, van der Waals, electrostatic, or hydrogen bonds to a label such that the presence of the molecule may be detected by detecting the presence of the label bound to the molecule.

The term "differentially expressed" or "differentially regulated" refers generally to a protein or nucleic acid biomarker that is overexpressed (upregulated) or underexpressed (downregulated) in one sample compared to at least one other sample. In the context of the present disclosure, the term generally refers to overexpression of CLL-1 on a cancer cell (e.g., an AML cell or AML CSC) compared to a normal, non-cancer cell.

For example, the terms "overexpressed" or "upregulated" interchangeably refer to a protein or nucleic acid, generally a biomarker that is transcribed or translated at a detectably greater than control level. The term includes overexpression due to transcription, post transcriptional processing, translation, post-translational processing, cellular localization (e.g., organelle, cytoplasm, nucleus, cell surface), and RNA and protein stability. Overexpression can be detected using conventional techniques for detecting biomarkers, whether mRNA (i.e., RT-PCR, hybridization) or protein (i.e., flow cytometry, imaging, ELISA, immunohistochemical techniques). Overexpression can be at least any of 10%, 20%, 30%, 40%, 50%, 60%, 70%, 80%, 90% or more in comparison to a normal cell.

The terms "agonist," "activator," "inducer" and like terms refer to molecules that increase activity or expression as compared to a control. Agonists are agents that, e.g., bind to, stimulate, increase, activate, enhance activation, sensitize or upregulate the activity of the target. The expression or activity can be increased at least any of 10%, 20%, 30%, 40%, 50%, 60%, 70%, 80%, 90% 100% or more than that in a control. In certain instances, the activation is any of 1.5-fold, 2-fold, 3-fold, 4-fold, 5-fold, 10-fold, or more in comparison to a control.

The terms "inhibitor," "repressor" or "antagonist" or "downregulator" interchangeably refer to a substance that results in a detectably lower expression or activity level as compared to a control. The inhibited expression or activity can be any of 10%, 20%, 30%, 40%, 50%, 60%, 70%, 80%, 90% or less than that in a control. In certain instances, the inhibition is any of 1.5-fold, 2-fold, 3-fold, 4-fold, 5-fold, 10-fold, or more in comparison to a control.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). In the context of the present disclosure, an example of a negative control would be a biological sample from a known healthy (non-cancer) individual, and an example of a positive control would be a biological sample from a known AML patient. A control can also represent an average value or a range gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of benefit and/or side effects). Controls can be designed for in vitro applications. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The term "diagnosis" refers to a relative probability that a subject has a disorder such as cancer. Similarly, the term "prognosis" refers to a relative probability that a certain future outcome may occur in the subject. For example, in the context of the present disclosure, prognosis can refer to the likelihood that an individual will develop cancer, have recurrence, be cured, or the likely severity of the disease (e.g., severity of symptoms, rate of functional decline, survival, etc.). The terms are not intended to be absolute, as will be appreciated by any one of skill in the field of medical diagnostics.

"Biopsy" or "biological sample from a patient" as used herein refers to a sample obtained from a patient having, or suspected of having, a CLL-1 associated disorder. The sample can also be a blood sample or blood fraction, e.g., white blood cell fraction, serum, or plasma. In some embodiments, the sample may be a tissue biopsy, such as needle biopsy, fine needle biopsy, surgical biopsy, etc. The sample can comprise a tissue sample harboring a lesion or suspected lesion, although the biological sample may be also be derived from another site, e.g., a site of suspected metastasis, a lymph node, or from the blood. In some cases, the biological sample may also be from a region adjacent to the lesion or suspected lesion.

A "biological sample" can be obtained from a patient, e.g., a biopsy, from an animal, such as an animal model, or from cultured cells, e.g., a cell line or cells removed from a patient and grown in culture for observation. Biological samples include tissues and bodily fluids, e.g., blood, blood fractions, lymph, saliva, urine, feces, etc.

The terms "therapy," "treatment," and "amelioration" refer to any reduction in the severity of symptoms. In the case of treating cancer (e.g., AML), treatment can refer to, e.g., reducing tumor size, number of cancer cells, growth rate, metastatic activity, reducing cell death of non-cancer cells, reduced nausea and other chemotherapy or radiotherapy side effects, etc. The terms "treat" and "prevent" are not intended to be absolute terms. Treatment and prevention can refer to any delay in onset, amelioration of symptoms, improvement in patient survival, increase in survival time or rate, etc. Treatment and prevention can be complete (undetectable levels of neoplastic cells) or partial, such that fewer neoplastic cells are found in a patient than would have occurred without the present invention. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

The terms "effective amount," "effective dose," "therapeutically effective amount," etc. refer to that amount of the therapeutic agent sufficient to ameliorate a disorder, as described above. For example, for the given parameter, a therapeutically effective amount will show an increase or decrease of therapeutic effect at least any of 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least any of a 1.2-fold, 1.5-fold, 2-fold, 5-fold, or more effect over a control.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. As used herein, the term "pharmaceutically acceptable" is used synonymously with physiologically acceptable and pharmacologically acceptable. A pharmaceutical composition will generally comprise agents for buffering and preservation in storage, and can include buffers and carriers for appropriate delivery, depending on the route of administration.

The terms "dose" and "dosage" are used interchangeably herein. A dose refers to the amount of active ingredient given to an individual at each administration. For the present invention, the dose can refer to the concentration of the antibody or associated components, e.g., the amount of therapeutic agent or dosage of radiolabel. The dose will vary depending on a number of factors, including frequency of administration; size and tolerance of the individual; severity of the condition; risk of side effects; the route of administration; and the imaging modality of the detectable moiety (if present). One of skill in the art will recognize that the dose can be modified depending on the above factors or based on therapeutic progress. The term "dosage form" refers to the particular format of the pharmaceutical, and depends on the route of administration. For example, a dosage form can be in a liquid, e.g., a saline solution for injection.

"Subject," "patient," "individual" and like terms are used interchangeably and refer to, except where indicated, mammals such as humans and non-human primates, as well as rabbits, rats, mice, goats, pigs, and other mammalian species. The term does not necessarily indicate that the subject has been diagnosed with a particular disease, but typically refers to an individual under medical supervision. A patient can be an individual that is seeking treatment, monitoring, adjustment or modification of an existing therapeutic regimen, etc. A "cancer patient" or "AML patient" can refer to an individual that has been diagnosed with cancer, is currently following a therapeutic regimen, or is at risk of recurrence, e.g., after surgery to remove a tumor. In some embodiments, the cancer patient has been diagnosed with cancer and is a candidate for therapy. Cancer patients can include individuals that have not received treatment, are currently receiving treatment, have had surgery, and those that have discontinued treatment.

In the context of treating cancer, a subject in need of treatment can refer to an individual that has cancer or a pre-cancerous condition, has had cancer and is at risk of recurrence, is suspected of having cancer, is undergoing standard treatment for cancer, such as radiotherapy or chemotherapy, etc.

"Cancer", "tumor," "transformed" and like terms include precancerous, neoplastic, transformed, and cancerous cells, and can refer to a solid tumor, or a non-solid cancer (see, e.g., Edge et al. *AJCC Cancer Staging Manual* ($7^{th}$ ed. 2009); Cibas and Ducatman *Cytology: Diagnostic principles*

*and clinical correlates* (3$^{rd}$ ed. 2009)). Cancer includes both benign and malignant neoplasms (abnormal growth). "Transformation" refers to spontaneous or induced phenotypic changes, e.g., immortalization of cells, morphological changes, aberrant cell growth, reduced contact inhibition and anchorage, and/or malignancy (see, Freshney, *Culture of Animal Cells a Manual of Basic Technique* (3$^{rd}$ ed. 1994)). Although transformation can arise from infection with a transforming virus and incorporation of new genomic DNA, or uptake of exogenous DNA, it can also arise spontaneously or following exposure to a carcinogen.

The term "cancer" can refer to leukemias, carcinomas, sarcomas, adenocarcinomas, lymphomas, solid and lymphoid cancers, etc. Examples of different types of cancer include, but are not limited to, acute myelogenous leukemia (AML), chronic myelogenous leukemia (CML), B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, multiple myelomas, lung cancer (e.g., non-small cell lung cancer or NSCLC), ovarian cancer, prostate cancer, colorectal cancer, liver cancer (i.e., hepatocarcinoma), renal cancer (i.e., renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma; head and neck cancer, osteogenic sarcoma, fibrosarcoma, neuroblastoma, glioma, and melanoma.

A "cancer target" or "cancer marker" is a molecule that is differentially expressed or processed in cancer, e.g., on a cancer cell or in the cancer milieu. Exemplary cancer targets are cell surface proteins such as CLL-1 (also, e.g., cell adhesion molecules and receptors), intracellular receptors, hormones, and molecules such as proteases that are secreted by cells into the cancer milieu. Markers for specific cancers are known in the art, e.g., CD45 for AML, CD34+CD38− for AML CSCs, MUC1 expression on colon and colorectal cancers, bombesin receptors in lung cancer, and prostate specific membrane antigen (PSMA) on prostate cancer.

In some embodiments, the cancer target can be associated with a certain type of cancer cell, e.g., AML, leukemia, myeloma, lymphoma, non-small cell lung cancer cells, prostate cancer, colorectal cancer, breast cancer or ovarian cancer. A cell type specific target is typically expressed at levels at least 2 fold greater in that cell type than in a reference population of cells. In some embodiments, the cell type specific marker is present at levels at least any of 3, 4, 5, 6, 7, 8, 9, 10, 20, 50, 100, or 1000 fold higher than its average expression in a reference population. Thus, the target can be detected or measured to distinguish the cell type or types of interest from other cells. For example, AML cancer targets include Cll-1, IL1Rap, GPR114, Ly86, LILRA1, and CD180.

A cancer stem cell (CSC) is a cell found in a tumor or blood cancer that can give rise to the cells that make up the bulk of the cancer. The CSC can also be self-renewing, similar to a normal (non-cancer) stem cell. CSCs can thus mediate metastasis by migrating to a non-tumor tissue in an individual and starting a "new" tumor. CSCs make up a very small percentage of any given cancer, depending on the stage that the cancer is detected. For example, the average frequency of CSCs in a sample of AML cells is believed to be about 1:10,000. Hematopoietic CSCs can be identified as CD34+, similar to normal hematopoietic stem cells (HSCs).

The terms "internalize," "internalization," "endocytose," "endocytosis," "engulf," and like terms refer to uptake of a substance by a cell, e.g., by antibody (or receptor)-mediated endocytosis or phagocytosis. The results of the ADC assays in Example 5 indicate that the presently disclosed CLL-1 antibodies can be internalized.

The terms "engraft" or "engraftment" refers to the ability of a cell to survive, proliferate, and/or properly localize upon introduction into an individual or tissue. In the case of a cancer stem cell (CSC), the term can refer to the ability of the CSC to generate a tumor de novo or to spread to a different site. The term is commonly used to describe the ability of a population of cells to survive and function in a xenograft model (e.g., engraftment of human cells in a mouse). Engraftment of hematopoietic cells can be determined as described, e.g., in WO2006/047569. Engraftment of tumor cells can be determined as described, e.g., in Beckhove et al. (2003) *Int. J. Cancer* 105:444.

The term "nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be naturally occurring ribonucleotides or deoxyribonucleotides, or synthetic or modified versions thereof. Examples of polynucleotides contemplated herein include single and double stranded DNA, single and double stranded RNA (including siRNA), and hybrid molecules having mixtures of single and double stranded DNA and RNA.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

A variety of methods of specific DNA and RNA measurements that use nucleic acid hybridization techniques are known to those of skill in the art (see, Sambrook, Id.). Some methods involve electrophoretic separation (e.g., Southern blot for detecting DNA, and Northern blot for detecting RNA), but measurement of DNA and RNA can also be carried out in the absence of electrophoretic separation (e.g., quantitative PCR, dot blot, or array).

The words "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring amino acids, modified or synthetic amino acids, as well as amino acid analogs and amino acid mimetics that function similarly to naturally occurring amino acids. Naturally occurring amino acids are those encoded by the genetic code. Modified amino acids include, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide are implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following amino acids are typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The terms "identical" or "percent identity," in the context of two or more nucleic acids, or two or more polypeptides, refer to two or more sequences or subsequences that are the same or have a specified percentage of nucleotides, or amino acids, that are the same (i.e., about 60% identity, e.g., at least any of 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nih.gov/BLAST. Such sequences are then said to be "substantially identical." Percent identity is typically determined over optimally aligned sequences, so that the definition applies to sequences that have deletions and/or additions, as well as those that have substitutions. The algorithms commonly used in the art account for gaps and the like. Typically, identity exists over a region comprising an antibody epitope, or a sequence that is at least about 25 amino acids or nucleotides in length, or over a region that is 50-100 amino acids or nucleotides in length, or over the entire length of the reference sequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous," with reference to a polynucleotide or polypeptide, indicates that the polynucleotide or polypeptide comprises two or more subsequences that are not found in the same relationship to each other in nature. For instance, a heterologous polynucleotide or polypeptide is typically recombinantly produced, having two or more sequences from unrelated genes arranged to make a new functional unit, e.g., a promoter from one source and a coding region from another source. Similarly, a heterologous protein indicates that the protein comprises two or more subsequences that are not found in the same relationship to each other in nature (e.g., a fusion protein).

II. CLL-1 Associated Disorders

The presently described antibodies can be used to detect and treat CLL-1 associated disorders, i.e., diseases correlated with elevated or reduced cell surface expression of CLL-1 as compared to CLL-1 expression in a standard control (e.g., a normal, non-disease, non-cancer cell). CLL-1 expression is normally limited to myeloid lineage cells, e.g., dendritic cells, granulocytes, and monocytes in the peripheral blood and spleen. Elevated CLL-1 levels are associated with cancer, in particular, in hematopoietic CSCs (e.g., LSCs), and in myeloproliferative disorders, including leukemias such as AML (acute myelogenous or myeloproliferative leukemia), MDS (myelodysplastic syndrome), myelofibrosis, CMML (chronic myelomonocytic leukemia), multiple myeloma, plasmacytoma, and CML (chronic myelogenous or myeloproliferative leukemia). See Bakker et al. (2004) *Cancer Res.* 64:8443; Van Rhenen et al. (2007) *Blood* 110:2659-66; Zhao et al. (2010) *Haematologica* (2010) 95:71; Van Rhenen et al. (2007) *Leukemia* 21:1700; and Herrmann et al. (2012) *Haematologica* 97:219.

AML cells can be characterized and distinguished from other cells by detecting cell surface marker expression. Aside from being CLL-1+, AML cells can be CD33+ (though some are CD33−), CD45+, and CDw52+. AML blasts (including LSCs) are typically CD34+CD38−. HSCs and LSCs can be characterized by expression of CD34, but the former do not express CLL-1. MDS cells can be characterized by expression of CD5, CD7, CD13, and CD34. CML cells can be characterized by expression of 7-ADD, CD33, CD34, and CD38.

Myelodysplastic Syndromes (MDS) include a group of closely-related blood formation disorders, in which the bone marrow shows qualitative and quantitative changes suggestive of a preleukemic process, but having a chronic course that does not necessarily terminate as acute leukemia. A variety of terms, including preleukemia, refractory anemia, refractory dysmyelopoietic anemia, smoldering or subacute leukemia, dysmyelopoietic syndrome (DMPS), and myelodysplasia, have all been used to describe MDS. These conditions are all characterized by a cellular marrow with impaired maturation (dysmyelopoiesis) and a reduction in the number of blood cells. DMPS is characterized by presence of megablastoids, megakaryocyte dysplasia, and an increase in number of abnormal blast cells, reflective of enhanced granulocyte maturation process. Patients with DMPS show chromosomal abnormalities similar to those found in acute myeloid leukemia and progress to acute myeloid leukemia in a certain fraction of afflicted patients.

Chronic myeloproliferative disorders are a collection of conditions characterized by increased number of mature and immature granulocytes, erythrocytes, and platelets. Chronic myeloproliferative disorders can transition to other forms within this group, with a tendency to terminate in acute myeloid leukemia. Specific diseases within this group include polycythemia vera, chronic myeloid leukemia, agnogenic myeloid leukemia, essential thrombocythemia, and chronic neutrophilic leukemia.

Myelofibrosis is characterized by scarring of the bone marrow that results in reduced number of red and white blood cells, and platelets. Myelofibrotic scarring can result from leukemia, but can have other causes, such as thrombocytosis or adverse drug effects.

III. Humanized Anti-CLL-1 Antibodies

Provided herein are humanized anti-CLL-1 antibodies (i.e., CLL-1 specific antibodies, anti-CLL-1) that specifically bind to human CLL-1, e.g., to the extracellular domain of a CLL-1 expressing cell.

In one embodiment, provided herein is a humanized antibody that binds CLL-1 and comprises a variable light chain and a variable heavy chain, wherein the variable light chain further comprises a CDRL1, CDRL2 and CDRL3 of murine M26, and the human framework sequences of IgKv1-16 and the variable heavy chain comprises CDRH1, CDRH2 and CDRH3 of murine M26, and the human framework sequences of IGHV1-46, except in each case with substitutions as provided in this disclosure. In some embodiments, the antibody light chain Kabat residues 65-67 are NRA or NGA. This deletes a glycosylation site (NRS). Replacement of NRS with NGS eliminated antibody binding activity. Replacement with NGA maintained antibody binding but introduced a potential deamination signal sequence. Replacement with NRA maintained antibody binding activity without introducing a potential deamination signal sequence.

In another embodiment, provided herein is a humanized antibody that binds CLL-1 comprising a variable light chain and a variable heavy chain, wherein the variable light chain comprises a CDRL1, CDRL2 and CDRL3 of murine M31, and the human framework sequences of X02990 and the variable heavy chain comprises a CDRH1, CDRH2 and CDRH3 of murine M31, and the human framework sequences of AF174092 or M17751, except in each case with substitutions as provided in this disclosure.

In some embodiments, the CLL-1 antibodies bind an epitope that includes a component that is outside the C lectin domain such that the antibodies bind a polypeptide consisting of the C lectin domain with lower affinity that a polypeptide consisting of the C lectin and stalk domains of CLL-1, or the extracellular domain of CLL-1. In some embodiments, the CLL-1 antibody binds a polypeptide consisting of the C-lectin domain of CLL-1 with a Kd at least 5-fold higher than a polypeptide consisting of the C-lectin and stalk domains of CLL-1 (e.g., any of 10, 20, 50, 100 or higher fold). For example, the CLL-1 antibodies designated as M26 and M31 bind amino acids 101-265 of human CLL-1 with higher affinity than amino acids 141-265 of human CLL-1 (with reference to SEQ ID NO:2). In some embodiments, the CLL-1 antibody binds the C lectin domain with a Kd that is at least 5, 10, 20, 50, or 100-fold higher than full length CLL-1 (or the full length extracellular domain of CLL-1).

In some embodiments, the CLL-1 antibodies have an affinity for human CLL-1 with a Kd of 1000 pM or lower, e.g., any of 800 pM, 700 pM, 600 pM, 500 pM, 400 pM, 300 pM, 200 pM, 100 pM, or lower. In some embodiments, the CLL-1 antibodies have an affinity for human CLL-1 with a Kd of 10 nM or lower, e.g., 1 nM or lower, 1-10 nM, 100-1000 pM, 10-1000 pM, about 1 nM or lower, 1-500 pM. In some embodiments, the CLL-1 antibodies also bind to primate CLL-1, e.g., cynomolgus CLL-1, with Kd that is 10 nM, 1 nM, 500 pM or less. In some embodiments, the CLL-1 antibodies bind cynomolgus CLL-1 with a Kd that is within an order of magnitude of the Kd for human CLL-1. One of skill will understand that lower Kd values indicate higher affinity.

In some embodiments, the CCL-1 antibodies bind a broad range of CLL-1 glycosylation variants. In some embodiments, the CLL-1 antibodies bind a form (e.g., a glycosylation variant) of CLL-1 that is expressed on AML cells. For example, the presently described CLL-1 antibodies can capture at least any of 65, 70, 75, 80, 85, 90, 95 or higher percent of the cells in an AML cell culture (e.g., HL60, THP1, and U937 cell lines). In some embodiments, the CLL-1 antibodies can bind at least any of 50, 60, 65, 70, 75, 80, 85, 90, 95 or higher percent of the cells in an AML patent sample (e.g., a PBMC sample or biopsy from an AML patient). One of skill will understand that, in such a cell binding assay, that an appropriate concentration of antibody is added, e.g., so that there are sufficient antibody molecules present to bind the number of cells in the culture or sample.

Surprisingly, CLL-1 antibodies described herein can inhibit growth of CLL-1-expressing cells in vitro and in vivo even in the absence of a conjugated cytotoxic agent. Given the high percentage of binding to AML cells from patient samples, the presently described antibodies provide a useful therapeutic option for AML patients, as well as those suffering from CLL-1+ MDS or CML.

The CLL-1 antibodies described herein also show complement dependent cytotoxicity (CDC) activity and antibody drug conjugate (ADC) activity. These CLL-1 antibodies can also thus be used to target CLL-1 expressing cells for destruction, e.g. in the absence of a conjugated cytotoxic agent.

In other embodiments, the CLL-1 antibody is a bi-specific antibody having a first arm having an antigen binding region that binds CLL-1, and a second arm having an antigen binding region that binds a second target antigen. The second target antigen can be any antigen of interest. For example, the second target antigen can be a cancer marker, i.e., a protein that is expressed at higher levels (e.g., more than 2x) on cancer cells (e.g., a cell surface protein) than on non-cancer cells. For example, the second target antigen can be selected from CD33, CD123/IL3Ra, IL1RAP, GPR-114, TIM-3, CD19, CD20, CD22, ROR1, mesothelin, c-Met, PSMA, Prostatic acid phosphatase (PAP), CEA, CA-125, Muc-1, AFP, Glycolipid F77, EGFRvIII, GD-2, NY-ESO-1 TCR, Tyrosinase, TRP1/gp75, gp100/pmel-17, Melan-A/ MART-1, Her2/neu, WT1, EphA3, telomerase, HPV E6, HPV E7, EBNA1, BAGE, GAGE, and MAGE A3 TCR, TCRSLITRK6, ENPP3, Nectin-4, CD27, SLC44A4, CAIX, Cripto, CD30, MUC16, GPNMB, BCMA, Trop-2, Tissue Factor (TF), CanAg, EGFR, αv-integrin, CD37, Folate Receptor, CD138, CEACAMS, CD56, CD70, CD74, GCC, 5T4, CD79b, Steapl, Napi2b, Lewis Y Antigen, LIV1 (ZIP6), Lymphocyte Antigen 6 Complex, Locus E (LY6E) and B7-H4. In some embodiments, the second target antigen is selected from IL1RAP, TIM-3, CD19, CD20, CD22, ROR1, mesothelin, CD33, CD123/IL3Ra, GPR114, c-Met, PSMA, prostatic acid phosphatase (PAP), CEA, CA-125, Muc-1, AFP, Glycolipid F77, EGFRvIII, GD-2, NY-ESO-1 TCR, tyrosinase, TRP1/gp75, gp100/pmel-17, Melan-A/ MART-1, Her2/neu, WT1, EphA3, telomerase, HPV E6, HPV E7, EBNA1, BAGE, GAGE and MAGE A3 TCRSLITRK6, ENPP3, Nectin-4, CD27, SLC44A4, CAIX, Cripto, CD30, MUC16, GPNMB, BCMA, Trop-2, Tissue Factor (TF), CanAg, EGFR, αv-integrin, CD37, Folate Receptor-α, CD138, CEACAMS, CD56, CD70, CD74, GCC, 5T4, CD79b, Steapl, Napi2b, Lewis Y Antigen, LIV, c-RET, DLL3, EFNA4, or Endosialin/CD248.

CLL-1 antibodies described herein have unique cell binding activities compared to previously characterized antibodies. For example, the presently described antibodies bind an epitope that is present on a higher percentage of primary cells from AML patients. These antibodies can be used for detecting cancer cells that display an epitope that is targeted with high affinity by at least one of the CLL-1 antibodies disclosed herein. In some embodiments, those cancer cells can then be targeted for destruction with the same CLL-1 antibody. Such methods can include treating an individual having CLL-1 expressing cancer cells comprising administering the CLL-1 antibody to the individual.

Numerous types of competitive binding assays are known, including solid phase direct or indirect radioimmunoassay (RIA); solid phase direct or indirect enzyme immunoassay (EIA), sandwich competition assay (see Stahli et al., *Methods in Enzymology* 9:242-253 (1983)); solid phase direct biotin-avidin EIA (see Kirkland et al., *J. Immunol.* 137:3614-3619 (1986)); solid phase direct labeled assay; solid phase direct labeled sandwich assay (see Harlow and Lane, *Antibodies, A Laboratory Manual*, Cold Spring Harbor Press (1988)); solid phase direct label RIA using 1-125 label (see Morel et al., *Molec. Immunol.* 25(1):7-15 (1988)); solid phase direct biotin-avidin EIA (Cheung et al., *Virology* 176:546-552 (1990)); and direct labeled RIA (Moldenhauer et al., *Scand. J. Immunol.* 32:77-82 (1990)). Typically, such an assay involves the use of purified antigen bound to a solid surface or cells bearing either of these, an unlabelled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

In some embodiments, the CLL-1 antibody has light chain CDR sequences and heavy chain CDR sequences having up to 1, 2, or 3 amino acid substitutions, additions, or deletions/ CDR relative to the CDR sequences of an antibody selected from the group consisting of M26 and M31. In some embodiments, the light chain CDR sequences include up to 1, 2, or 3 amino acid substitutions, additions or deletions/ CDR relative to the light chain CDR sequences of the aforementioned CLL-1 antibodies. In some embodiments, the heavy chain CDR sequences include up to 1, 2, or 3 amino acid substitutions, additions, or deletions/CDR relative to the heavy chain CDR sequences of the aforementioned CLL-1 antibodies. In some embodiments, substitution, addition or deletion occurs in only 1, 2, 3, 4, or 5 CDRs of the 6 total CDRs.

In some embodiments, the antibody also has at least one activity selected from:

Binding to human CLL-1 with a Kd of 10 nM or lower, e.g., 1 nM or lower, 1-10 nM, 100-1000 pM, 10-1000 pM, about 1 nM or lower, 1-500 pM, etc.;

An EC50 of 200 ng/ml or less in a CDC assay with HL60 cells or CLL-1 expressing AML cells from an AML patient;

An EC50 of 100 pM of less in a ADC assay with HL60 cells or CLL-1 expressing AML cells from an AML patient; and Reducing cell growth of CLL-1-expressing cells (e.g., HL60, AML cells), compared to cell growth in the absence of the antibody.

Any of the antibodies described herein can be a chimeric antibody or a humanized antibody. In some embodiments, the antibody is a CLL-1-binding antibody fragment, e.g., an Fab. In some embodiments, the CLL-1 antibody is labeled with a detectable agent, e.g., as described below. In some embodiments, the CLL-1 antibody is attached, e.g., covalently, to a therapeutic agent, e.g., a chemotherapeutic or cytotoxic agent as described below.

A. Methods of Making Antibodies

For preparation of the presently described antibodies, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3$^{rd}$ ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, can be used to express humanized or human antibodies (see, e.g., U.S. Pat. Nos. 5,545,807; 5,545,806; 5,569,825; 5,625, 126; 5,633,425; 5,661,016, Marks et al., *Bio/Technology*

10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Antibodies can be produced using any number of expression systems, including prokaryotic and eukaryotic expression systems. In some embodiments, the expression system is a mammalian cell expression, such as a hybridoma, or a CHO cell expression system. Many such systems are widely available from commercial suppliers. In embodiments in which an antibody comprises both a $V_H$ and $V_L$ region, the $V_H$ and $V_L$ regions may be expressed using a single vector, e.g., in a di-cistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

An antibody of the invention can also be produced in various formats, including as a Fab, a Fab', a F(ab')$_2$, a scFv, or a dAB. The antibody fragments can be obtained by a variety of methods, including, digestion of an intact antibody with an enzyme, such as pepsin (to generate (Fab')$_2$ fragments) or papain (to generate Fab fragments); or de novo synthesis. Antibody fragments can also be synthesized using recombinant DNA methodology. In some embodiments, the CLL-1 antibody comprises F(ab')$_2$ fragments that specifically bind CLL-1. An antibody of the invention can also include a human constant region. See, e.g., Fundamental Immunology (Paul ed., 4d ed. 1999); Bird, et al., *Science* 242:423 (1988); and Huston, et al., *Proc. Natl. Acad. Sci. USA* 85:5879 (1988).

Methods for humanizing non-human antibodies (i.e., using CDRs from non-human antibodies) are also known in the art. Generally, a humanized antibody has one or more amino acid residues from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In some cases, the antibody or antibody fragment can be conjugated to another molecule, e.g., polyethylene glycol (PEGylation) or serum albumin, to provide an extended half-life in vivo. Examples of PEGylation of antibody fragments are provided in Knight et al. *Platelets* 15:409, 2004 (for abciximab); Pedley et al., *Br. J. Cancer* 70:1126, 1994 (for an anti-CEA antibody); Chapman et al., *Nature Biotech.* 17:780, 1999; and Humphreys, et al., *Protein Eng. Des.* 20:227, 2007). The antibody or antibody fragment can also be labeled, or conjugated to a therapeutic agent as described below.

B. Binding Affinity

The specificity of the binding can be defined in terms of the comparative dissociation constants (Kd) of the antibody (or other targeting moiety) for target, as compared to the dissociation constant with respect to the antibody and other materials in the environment or unrelated molecules in general. Typically, the Kd for the antibody with respect to the unrelated material will be at least 2-fold, 3-fold, 4-fold, 5-fold, 10-fold, 20-fold, 50-fold, 100-fold, 200-fold or higher than Kd with respect to the target.

The desired affinity (Kd) for an antibody, e.g., high (pM to low nM), medium (low nM to 100 nM), or low (about 100 nM or higher), may differ depending upon whether it is being used as a diagnostic or therapeutic. Without being limited to theory, in one example, an antibody with medium affinity may be more successful in localizing to a tumor as compared to one with a high affinity. Thus, antibodies having different affinities can be used for diagnostic and therapeutic applications.

A targeting moiety will typically bind with a Kd of less than about 1000 nM, e.g., less than 250, 100, 50, 20 or lower nM. In some embodiments, the Kd of the affinity agent is less than 15, 10, 5, or 1 nM. In some embodiments, the Kd is 1-100 nM, 0.1-50 nM, 0.1-10 nM, or 1-20 nM. The value of the dissociation constant (Kd) can be determined by well-known methods, and can be computed even for complex mixtures by methods as disclosed, e.g., in Caceci et al., Byte (1984) 9:340-362.

Affinity of an antibody, or any targeting agent, for a target can be determined according to methods known in the art, e.g., as reviewed in Ernst et al. Determination of Equilibrium Dissociation Constants, *Therapeutic Monoclonal Antibodies* (Wiley & Sons ed. 2009).

Quantitative ELISA, and similar array-based affinity methods can be used. ELISA (Enzyme linked immunosorbent signaling assay) is an antibody-based method. In some cases, an antibody specific for target of interest is affixed to a substrate, and contacted with a sample suspected of containing the target. The surface is then washed to remove unbound substances. Target binding can be detected in a variety of ways, e.g., using a second step with a labeled antibody, direct labeling of the target, or labeling of the primary antibody with a label that is detectable upon antigen binding. In some cases, the antigen is affixed to the substrate (e.g., using a substrate with high affinity for proteins, or a Streptavidin-biotin interaction) and detected using a labeled antibody (or other targeting moiety). Several permutations of the original ELISA methods have been developed and are known in the art (see Lequin (2005) *Clin. Chem.* 51:2415-18 for a review).

The Kd, Kon, and Koff can also be determined using surface plasmon resonance (SPR), e.g., as measured by using a Biacore T100 system. SPR techniques are reviewed, e.g., in Hahnfeld et al. Determination of Kinetic Data Using SPR Biosensors, *Molecular Diagnosis of Infectious Diseases* (2004). In a typical SPR experiment, one interactant (target or targeting agent) is immobilized on an SPR-active, gold-coated glass slide in a flow cell, and a sample containing the other interactant is introduced to flow across the surface. When light of a given frequency is shined on the surface, the changes to the optical reflectivity of the gold indicate binding, and the kinetics of binding.

Binding affinity can also be determined by anchoring a biotinylated interactant to a streptavidin (SA) sensor chip. The other interactant is then contacted with the chip and detected, e.g., as described in Abdessamad et al. (2002) *Nuc. Acids Res.* 30:e45.

C. Determining CLL-1 Epitope

The site of antibody binding to CLL-1 can be mapped using known techniques for epitope mapping. One of skill will appreciate that the approach used for epitope mapping can vary depending on the antigen, e.g., where it is expressed in the cell, post-translational modifications of the primary polypeptide sequence, and differences between antigen structure on different cells or in different environments.

CLL-1 is a transmembrane protein with approximately 200 extracellular amino acids. The extracellular domain is glycosylated, and includes a C lectin domain. The epitope for a CLL-1 antibody can be determined or partially determined by varying the primary sequence or glycosylation state of CLL-1, and comparing the affinity of the CLL-1 antibody to the different variants of CLL-1.

Such epitope mapping can be carried out in vitro, e.g., by screening phage display libraries or synthetic peptide libraries, e.g., using beads or other solid matrices. Linear epitopes are typically about six amino acids, though this can vary somewhat. In order to mimic linear epitopes present in a protein, synthetic peptides can be made corresponding to the sequence. In some embodiments, this sequence is extended on the N and/or C terminals to provide additional amino acid residues that are present in the flanking sequences in the protein. This can more closely mimic the primary, and to a certain extent, the secondary structure environment of the epitope. Additionally, residues including but not limited to one or more glycines or gamma amino butyric acid, can be appended to either terminus to provide a spacer to minimize steric interactions with, for example, a solid phase used in an immunoassay. Spacer length is often varied to determine empirically the best structure.

Because of the variable nature of the epitope and the potential effects due to the flanking sequences, in some embodiments, one can use peptides that vary in length by extending the N or C terminals by a certain number of residues. Another approach utilizes repeating peptide epitopes, or alternating epitopes with intervening spacer residues. The length of these peptides is often varied according to the number of repeating units desired.

One approach for epitope mapping is to synthesize overlapping peptides, for example 20 residues in length, with a six residue overlap, which cover the primary sequence of the CLL-1 extracellular region. If such peptide screening is used to map the epitope, peptides can be modified to overcome the undesirable interactions with solid phase supports used in immunoassays. One way is to substitute hydrophobic residues in the peptide with hydrophilic ones, in order to reduce or minimize the hydrophobic interactions, and increased peptide accessibility. Similarly, charged peptide residues can be substituted with noncharged residues to eliminate ionic interactions with the solid phase. Peptides can also be modified by adding spacer groups of a variety of structures to position the peptide epitope further from the solid phase and minimize steric hindrance.

Peptides can be synthesized to reflect post-translational modifications that are present on the native protein, or the native protein on targeted cells. Modifications include but are not limited to glycosylation and phosphorylation at specific sites in the protein.

Another approach for determining the epitope is to express CLL-1 variants in cells, and compare CLL-1 antibody affinities between the different variants. The CLL-1 variants can be designed as described for the peptide studies. In addition, glycosylated residues (e.g., asparagine, arginine, serine, threonine, tyrosine) can be substituted to determine whether the epitope includes a glycosylation site. Similarly, phosphorylated residues (serine, threonine, tyrosine) can be substituted.

The epitope can also be determined or partially determined by comparing antibody affinity for different types of CLL-1 expressing cells. For example, antibody affinity can be determined and compared for primary AML cells, e.g., AML blasts and engrafted AML tumor cells; for AML cell lines, for other non-cancerous myeloid cells, etc.

D. CDC, ADCC, and ADC Assays

The presently described antibodies are effective for cell dependent cytotoxicity ("CDC"), antibody dependent cell-mediated cytotoxicity ("ADCC"), and antibody drug conjugate cytotoxicity ("ADC") of cells that express CLL-1. Exemplary cells that express CLL-1 include cell lines that express heterologous, recombinant CLL-1 (e.g., human CLL-1); human AML cell lines such as HL60, THP1, TF1-alpha, U937, and OCI AML-5 (the first four of which are available from ATCC); primary cells from one or more AML patients (e.g., PBMC or engrafted tumor cells); human CML cell lines such as K562 and KU812 (available from ATCC); and primary cells from one or more CML or MDS patients.

An antibody is described as having CDC activity and mediating CDC if it results in complement dependent killing of cells that express the antibody target. CDC assays are known in the art, and are described, e.g., in Gazzano-Santoro et al. (1997) *J. Immunol.* Methods 202:163; Idusogie et al. (2000) *J Immunol.* 164:4178. CDC kits and services are commercially available, e.g. from GeneScript® and Cell Technology Inc.

In brief, the assay is typically carried out in vitro, and includes antibody binding to a cell expressing the antibody target on its surface. Complement components, including C1q which binds to the Ch region of the antibody, are added. The complement components then interact to kill the targeted cell. CDC is measured after a period of incubation of generally between 4 and 24 hours, for example, by determining the release of intracellular enzyme or granules known to be present in the targeted cell, by comparing the starting and ending target cell population, etc.

An antibody is described as having ADCC activity and mediating ADCC if it results in killing of antibody-bound cells (e.g., CLL-1 expressing cells) by effector cells. Effector cells are typically natural killer cells, but can also be macrophages, neutrophils, or eosinophils. Genetically engineered effector cell lines have also been developed for use in ADCC assays (see, e.g., Schnueriger et al. (2011)*Mol. Immunol.* 48:1512). ADCC assays are known in the art, and are described, e.g., in Perussia and Loza (2000) *Methods in Mol. Biol.* 121:179; Bretaudeau and Bonnaudet (2011) *BMC Proceedings* 5(Suppl 8):P63. ADCC kits and services are commercially available, e.g. from GeneScript® and Promega®.

In brief, the assay is typically carried out in vitro, and includes antibody binding to a cell expressing the antibody target on its surface. Effector cells are added that recognize antibody-bound cells, typically through an Fc receptor such as CD16. The effector cells kill the antibody-bound cell, e.g., by releasing cytotoxins that cause apoptosis. Cell death is detected by release of a detectable element within the target cells (e.g., Cr51) or by detection of an element involved in the cell mediated toxicity (e.g., activation of NFAT signaling in effector cells).

An antibody is described as having antibody-drug conjugate (ADC) activity (or mediating ADC) if the antibody, when conjugated with a cytotoxic agent (drug), results in killing (inhibiting survival) a cell that expresses the target of the antibody, in this case, CLL-1. Appropriate cytotoxic agents are known in the art, e.g., saporin, doxorubicin, daunomycin, vinca-alkaloids, taxoids, tubulin agents (e.g., Maytansin, auristatin), and DNA agents (e.g., calicheamicin, duocarmycin, pyrrolobenzodiazepine dimers), etc. ADC assays are known in the art, e.g., as described in Gerber et al. (2009) 3:247, and in the Examples below.

E. Internalization

The CLL-1 antibodies described herein can be internalized into CLL-1-expressing cells, including CLL-1 AML cells. That is, a CLL-1 expressing cell can internalize the antibodies described herein. The CLL-1 antibodies described herein provide an effective means for targeting such cells, e.g., with detectable or cytotoxic conjugates.

The percent internalization and internalization rate of an antibody can be evaluated by using methods known in the art, including, e.g., flow cytometry (FACS) and confocal fluorescent microscopy. Such methods are described, e.g., in Lue et al. (2007) *Nature Protocols* (*Nature Med.* 13:587-96); Cho et al. (2010) *Biomacromolecules* and Corbani et al. (2004) *Endocrinology* 145:2876-85, and as described herein.

For FACS and confocal microscopy, cells are incubated with a fluorescently-labeled targeting agent, e.g., antibody. The cells are typically selected to express the target of the labeled antibody, e.g., CLL-1. Control cells can then be used that do not express the target. Internalization typically occurs at 37° C., but not at 4° C., which provides another control for the reaction. The cells can thus be contacted with the labeled agent and incubated at 37° C. or 4° C. (e.g., to detect binding without internalization).

Unbound, and surface-bound agent is removed by washing the cells, e.g., in an acid wash, followed by wash with a buffer at normal pH.

If adherent cells are used, the cells are removed from substrate prior to flow cytometry. The percentage of fluorescent cells indicates the percent internalization of the fluorescently-labeled agent. Percent internalization can also be expressed, e.g., as a percent of initial labeled agent added to the cells.

Internalization of an agent can also be evaluated by determining the localization of the fluorescently labeled agent by confocal microscopy. Methods of using confocal microscopy to determine internalization are described in, e.g., Xiao et al. (2008) *Chem. Eur. J.,* 14:1769-1775. Briefly, the cells are contacted with labeled agent and incubated as described above. Following incubation, the cells can be incubated on ice, washed in PBS buffer at 4° C., treated with 0.25% trypsin (to remove from substrate, if applicable). The cell suspension can then be applied to slides for confocal fluorescent microscopy. Suitable confocal microscopes include the FV500-IX81 confocal microscope (Olympus America Inc.; Center Valley, Pa.) and Eclipse Ti-E (Nikon Instruments Inc.; Melville, N.Y.).

IV. Chimeric Antigen Receptors

Also provided herein are chimeric antigen receptors comprising an antigen binding domain that binds to CLL-1 and that comprises humanized portions of light and heavy chains as described. In some embodiments, the hinge region of the disclosed CARs can be selected from the CD8, CD4, or CD28 extracellular domain or the Fc region of an IgG1 antibody. The transmembrane domain can comprise a transmembrane domain of an immunoglobulin family receptor, such as CD8. The intracellular domain can be selected from any membrane-spanning molecule on a T cell. For example, the transmembrane (TM) domain of the disclosed CAR can comprise the TM domain of CD2, CD3, CD16, CD32, CD64, CD28, CD247, 4-1BBL, CD4, or CD8. One or more intracellular signaling domains can comprise a CD3 signaling domain, a signal transduction domain of any one of the Fc-alpha, Fc-gamma, Fc-epsilon, Fc-mu, and Fc-delta receptors, a co-stimulatory domain derived from for example, CD28, 4-1BB, CD2, CD27, CD30, OX40, CD40, PD-1, PD-L1, PD-L2, ICOS, LFA-1, CD7, LIGHT, NKG2C, CD83L, B7-1 (CD80), B7-2 (CD86), B7-H3, B7-H4 and others In one embodiment, one signal transduction domain comprises a signal transduction domain from CTLA4.

Polynucleotides encoding chimeric antigen receptors can be used to transduce a variety of immune cells, including cells of the lymphoid or myeloid lineage, such as hematopoietic stem cells, T cells (CD4 T-cells, CD8 alpha T-cells, CD8 beta T cells, T helper cells, T memory stem cell), B cells, myeloid progenitor cells (MPCs), lymphoid progenitor cells, macrophages, granulocytes (neutrophils, basophils, eosinophils), megakaryocytes, monocytes and dendritic cells.

Such cells can be used, for example, in therapeutic methods. Cells administered to a subject can target and, in conjunction with the host immune system, mount an attack on cells bearing targets to which the antigen binding moiety binds. For example, such cells can be used to treat a cancer such as the myeloproliferative disorder, e.g., selected from the group consisting of: AML, CML, CMML, multiple myeloma, pasmocytoma and myelofibrosis.

V. Diagnostic Applications

The CLL-1 antibodies described herein specifically bind CLL-1-expressing cells. CLL-1 antibodies can thus be used for in vitro and in vivo diagnostic assays to detect CLL-1-expressing cells (e.g., AML cells and AML CSCs). For example, a sample (e.g., blood sample or tissue biopsy) can be obtained from a patient and contacted with a CLL-1 antibody, and the presence of a CLL-1-expressing cell in the patient sample can be determined by detecting antibody binding. Antibody binding can be detected directly (e.g., where the antibody itself is labeled) or by using a second detection agent, such as a secondary antibody. The detectable label can be associated with an antibody of the invention, either directly, or indirectly, e.g., via a chelator or linker.

In some embodiments, the CLL-1 antibody is contacted with a biological sample from an individual having or suspected of having a CLL-1 associated disorder, and antibody binding to a cell in the sample is determined, wherein higher or lower than normal antibody binding indicates that the individual has a CLL-1 associated disorder. In some embodiments, the biological sample is a blood sample or blood fraction (e.g., serum, plasma, platelets, red blood cells, white blood cells, PBMCs). In some embodiments, the biological sample is a tissue sample (biopsy), e.g., from a suspected tumor site, or from a tissue that is known to be affected, e.g., to determine the boundaries of a known tumor.

Biopsies are typically performed to obtain samples from tissues, i.e., non-fluid cell types. The biopsy technique applied will depend on the tissue type to be evaluated (e.g., breast, skin, colon, prostate, kidney, lung, bladder, lymph node, liver, bone marrow, airway or lung). In the case of a cancer the technique will also depend on the size and type of the tumor (e.g., solid, suspended, or blood), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally obtains a suspension of cells from within the tumor mass. Biopsy techniques are discussed, for example, in Harrison's Principles of Internal Medicine, Kasper, et al., eds., 16th ed., 2005, Chapter 70, and throughout Part V.

Any method of detecting antibody binding to a cell in a sample can be used for the present diagnostic assays. Methods of detecting antibody binding are well known in the art, e.g., flow cytometry, fluorescent microscopy, ELISAs, etc. In some embodiments, the method comprises preparing the biological sample for detection prior to the determining step. For example, a subpopulation of cells (e.g., white blood cells, CD34+ cells, CD45+ cells, etc.) can be separated from the rest of the sample from the individual (e.g., other blood components) or cells in a tissue can be suspended for easier detection.

In some embodiments, the percentage of CLL-1-expressing cells in the sample is determined and compared to a control, e.g., a sample from an individual or group of individuals that are known to have a CLL-1 associated disorder (positive control) or from an individual or group of individuals that are known not to have a CLL-1 associated disorder (normal, healthy, non-disease, or negative control). In some embodiments, the control is a standard range of CLL-1 expression established for a given tissue. A higher or lower than normal percentage of CLL-1 expressing cells, or higher or lower expression level, indicates that the individual has a CLL-1 associated disorder.

In some embodiments, a labeled CLL-1 antibody can be provided (administered) to an individual to determine the applicability of an intended therapy. For example, a labeled antibody may be used to detect CLL-1 density within a diseased area, where the density is typically high relative to non-diseased tissue. A labeled antibody can also indicate that the diseased area is accessible for therapy. Patients can thus be selected for therapy based on imaging results. Anatomical characterization, such as determining the precise boundaries of a cancer, can be accomplished using standard imaging techniques (e.g., CT scanning, MRI, PET scanning, etc.).

In some embodiments, labeled CLL-1 antibodies as described herein can be further associated with a therapeutic compound, e.g., to form a "theranostic" composition. For example, an CLL-1 antibody can be linked (directly or indirectly) to both a detectable label and a therapeutic agent, e.g., a cytotoxic agent to kill CLL-1-expressing cancer cells. In some embodiments, a labeled CLL-1 antibody is used for diagnosis and/or localization of a CLL-1 expressing cancer cell, and the CLL-1 expressing cancer cell is then targeted with a separate therapeutic CLL-1 specific antibody. In some embodiments, the diagnostic CLL-1 specific antibody is one that is not internalized into CLL-1-expressing cells at a high rate or percentage. In some embodiments, the therapeutic CLL-1 antibody is internalized into CLL-1-expressing cells at a high rate or percentage.

A. Labels

A diagnostic agent comprising a CLL-1 antibody can include any diagnostic agent known in the art, as provided, for example, in the following references: Armstrong et al., *Diagnostic Imaging*, 5$^{th}$ Ed., Blackwell Publishing (2004); Torchilin, V. P., Ed., *Targeted Delivery of Imaging Agents*, CRC Press (1995); Vallabhajosula, S., *Molecular Imaging: Radiopharmaceuticals for PET and SPECT*, Springer (2009). A diagnostic agent can be detected by a variety of ways, including as an agent providing and/or enhancing a detectable signal. Detectable signals include, but are not limited to, gamma-emitting, radioactive, echogenic, optical, fluorescent, absorptive, magnetic, or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like. The terms "detectable agent," "detectable moiety," "label," "imaging agent," and like terms are used synonymously herein.

In some embodiments, the label can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives. Fluorescent dyes are discussed, for example, in U.S. Pat. Nos. 4,452,720, 5,227,487, and 5,543,295.

The label can also be a radioisotope, e.g., radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In some embodiments, radioactive agents can include $^{111}$In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In some embodiments, the agents can include DOTA and its various analogs with $^{111}$In, $^{177}$Lu, $^{153}$Sm, $^{88/90}$Y, $^{62/64/67}$Cu, or $^{67/68}$Ga. In some embodiments, a nanoparticle can be labeled by incorporation of lipids attached to chelates, such as DTPA-lipid, as provided in the following references: Phillips et al., *Wiley Interdisciplinary Reviews: Nanomedicine and Nanobiotechnology*, 1(1): 69-83 (2008); Torchilin, V. P. & Weissig, V., Eds. *Liposomes 2nd Ed*.: Oxford Univ. Press (2003); Elbayoumi, T. A. &

Torchilin, V. P., *Eur. J. Nucl. Med. Mol. Imaging* 33:1196-1205 (2006); Mougin-Degraef, M. et al., *Intl J. Pharmaceutics* 344:110-117 (2007).

In some embodiments, the diagnostic agent can be associated with a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Secondary binding ligands include, e.g., biotin and avidin or streptavidin compounds as known in the art.

In some embodiments, the labeled antibody can be further associated to a composition that improves stability in vivo, e.g. PEG or a nanoparticle such as a liposome, as described in more detail below.

B. Methods of Labeling

Techniques for conjugating detectable and therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)).

Typically, the antibody is attached to detectable moiety in an area that does not interfere with binding to the epitope. Thus in some cases, the detectable moiety is attached to the constant region, or outside the CDRs in the variable region. One of skill in the art will recognize that the detectable moiety can be located elsewhere on the antibody, and the position of the detectable moiety can be adjusted accordingly. In some embodiments, the ability of the antibody to associate with the epitope is compared before and after attachment to the detectable moiety to ensure that the attachment does not unduly disrupt binding.

In some embodiments, the antibody can be associated with an additional targeting moiety. For example, an antibody fragment, peptide, or aptamer that binds a different site on the target molecule or target cell can be conjugated to the antibody to optimize target binding, e.g., to a cancer cell.

VI. Therapeutic Applications

CLL-1-expressing cells such as AML cells can be targeted using the CLL-1 antibodies described herein. CLL-1 expression is elevated on AML cells and CSCs (e.g., AML CSCs). CLL-1 is not significantly expressed on normal CD34+ hematopoietic stem cells (HSCs), thus CSCs can be distinguished from HSCs using the present CLL-1 antibodies. High affinity CLL-1 antibodies that recognize a CLL-1 epitope common to AML cells, and thus able to universally bind to AML cells, is particularly valuable, as AML has a very high rate of recurrence. As noted above, a therapeutic composition comprising CLL-1 antibody can further include a detectable label to form a theranostic composition, e.g., for detection and localization of CLL-1 expressing cells, and monitoring of therapeutic effect.

As demonstrated herein, the present CLL-1 antibodies can inhibit cancer cell growth (proliferation and/or engraftment) and thus can be considered chemotherapeutic agents alone. The following disclosure provides examples of chemotherapeutic and cytotoxic agents that can be linked (conjugate) to CLL-1 antibody for additional effect on CLL-1-expressing cells.

A chemotherapeutic (anti-cancer) agent can be any agent capable of reducing cancer growth, interfering with cancer cell replication, directly or indirectly killing cancer cells, reducing metastasis, reducing tumor blood supply, etc. Chemotherapeutic agents thus include cytotoxic agents. Cytotoxic agents include but are not limited to saporin, taxanes, vinca alkaloids, anthracycline, and platinum-based agents. Classes of chemotherapeutic agents include but are not limited to alkylating agents, antimetabolites, e.g., methotrexate, plant alkaloids, e.g., vincristine, and antibiotics, e.g., doxorubicin as well as miscellaneous drugs that do not fall in to a particular class such as hydroxyurea. Platinum-based drugs, exemplified by cisplatin and oxaliplatin, represent a major class of chemotherapeutics. These drugs bind to DNA and interfere with replication. Taxanes, exemplified by taxol, represent another major class of chemotherapeutics. These compounds act by interfering with cytoskeletal and spindle formation to inhibit cell division, and thereby prevent growth of rapidly dividing cancer cells. Other chemotherapeutic drugs include hormonal therapy. Further chemotherapeutic drugs include but are not limited to, pyrrolo benzodiazepines, indolino benzodiazepines and isoquinolidinobenzodiazepines, include for example those described in WO 2016/149546, which is incorporated by reference. The benzodiazepines can be for example homodimers or hetero-dimers.

More than one therapeutic agent can be combined, either in the same composition, or in separate compositions. The therapeutic agent(s) can also be combined with additional therapeutic agents as appropriate for the particular individual. Common therapeutic agents provided to cancer patients include medications to address pain, nausea, anemia, infection, inflammation, and other symptoms commonly experienced by cancer patients.

Antibodies can be attached to a therapeutic agent, detectable agent, or nanocarrier using a variety of known cross-linking agents. Methods for covalent or non-covalent attachment of polypeptides are well known in the art. Such methods may include, but are not limited to, use of chemical cross-linkers, photoactivated cross-linkers and/or bifunctional cross-linking reagents. Exemplary methods for cross-linking molecules are disclosed in U.S. Pat. No. 5,603,872 and U.S. Pat. No. 5,401,511. Non-limiting examples of cross-linking reagents include glutaraldehyde, bifunctional oxirane, ethylene glycol diglycidyl ether, carbodiimides such as 1-ethyl-3-(3-dimethylaminopropyl) carbodiimide or dicyclohexylcarbodiimide, bisimidates, dinitrobenzene, N-hydroxysuccinimide ester of suberic acid, disuccinimidyl tartarate, dimethyl-3,3'-dithio-bispropionimidate, azidoglyoxal, N-succinimidyl-3-(2-pyridyldithio)propionate and 4-(bromoadminoethyl)-2-nitrophenylazide.

In some embodiments, the antibody or antibody fragment described herein ("Ab") is conjugated to the drug unit via a linker to provide a drug-linker-Ab conjugate. A "linker" refers to a moiety that connects a first molecule to a second molecule through chemical bonds. A linker can be used to link a drug unit and an antibody or antibody fragment to form a drug-linker-antibody (or antibody fragment) conjugate. Various non-limiting examples of linker units are set forth in U.S. Pat. Nos. 5,635,483; 5,780,588; 5,663,149; 7,964,566; and U.S. Patent Application Pub. No. 2011/0020343 (U.S. Ser. No. 12/933,364), each of which is herein specifically incorporated by reference in its entirety). The antibody or antibody fragment may include a functional group which can form a bond with a functional group of the linker. Non-limiting examples of useful functional groups include sulfhydryl (—SH), amino, hydroxyl, carboxy, the anomeric hydroxyl group of a carbohydrate, and carboxyl. The linker may optionally include a "stretcher" unit as defined in U.S. Pat. No. 7,964,566, herein specifically incorporated by reference.

In some embodiments, the linker includes one or more amino acid moieties. For example, the linker may include a dipeptide, a tripeptide, a tetrapeptide, a pentapeptide, a hexapeptide, a heptapeptide, an octapeptide, a nonapeptide, a decapeptide, an undecapeptide, or a dodecapeptide unit. The linker may optionally comprise valine-citrulline, phenylalanine-lysine, N-methylvaline-citrulline, 5-aminovaleric acid, homo phenylalanine lysine, tetraisoquinolinecarboxylate lysine, cyclohexylalanine lysine, isonepecotic acid lysine, beta-alanine-lysine, glycine serine valine glutamine and isonepecotic acid. The amino acids may be natural amino acids or non-natural amino acids.

In some embodiments, the linker can include ethylene glycol repeating units, and one or more amino acid. In some embodiments, the linker includes the formula:

—(CH$_2$CH$_2$O)$_{1-50}$—X$_{AA}$— wherein X$_{AA}$ is an amino acid sequence.

Any suitable number of ethylene glycol units can be used in the linker. For example, the linker can include 1, 2, 3, 4, 5, 6, 7, 8, 9, 10, 11, 12, 15, 16, 19, 20, 23, 24, 35, 36, 37, 48, 49, or more ethylene glycol units. In some embodiments, the linker L includes the formula:

—HN-PEG-C(O)—X$_{AA}$— wherein PEG has 1-50 ethylene glycol units, and X$_{AA}$ is an amino acid sequence.

The amino acid portion of the linker can include any suitable number of amino acid moieties, as described above. For example, the amino acid sequence XAA can include from 1 to 100 amino acid moieties, or from 1 to 10 amino acid moieties, or from 1 to 5 amino acid moieties. In some embodiments, the linker can include 1, 2, 3, 4, 5, 6, 7, 8, 9, 10, or more amino acid moieties.

In some embodiments, the CLL-1 antibody is associated with a nanocarrier. For antibodies conjugated to nanocarriers (e.g., liposomes), a certain number of antibodies will be present on the surface, i.e., at a given surface density. In some embodiments, the nanocarrier will have at least 5 antibodies per nanocarrier, e.g., at least 10, 30, 40, 50, 75, 100 or higher antibodies per nanocarrier. One of skill in the art will understand that surface density represents an average range, as the number of antibodies per nanocarrier will not be absolutely uniform for all members of the population.

Nanocarriers include vesicles such as liposomes and micelles, as well as polymeric nanoparticles, etc. Nanocarriers are useful for delivery of therapeutic and diagnostic agents, but can be particularly useful for shielding cytotoxic agents used to treat cancer. The nanocarrier can comprise lipids (e.g., phospholipids), hydrophilic polymers, hydrophobic polymers, amphipathic compounds, cross-linked polymers, and a polymeric matrix (see, e.g., WO2009/110939). Depending on the application, the nanocarrier can be designed to have a particular size, half-life, shelf life, and leakage rate.

Preparation of nanocarriers, such as an antibody targeted liposome, polymeric nanoparticle, or extended shelf-life liposome, is described, e.g., in U.S. Pat. Nos. 6,465,188, 7,122,202, 7,462,603 and 7,550,441.

In some embodiments, the antibody is linked to a stabilizing moiety such as PEG, or a liposome or other nanocarrier. U.S. Pat. Nos. 4,732,863 and 7,892,554 and Chattopadhyay et al. (2010)*Mol Pharm* 7:2194 describe methods for attaching the selected antibody to PEG, PEG derivatives, and nanoparticles (e.g., liposomes). Liposomes containing phosphatidyl-ethanolamine (PE) can be prepared by established procedures as described herein. The inclusion of PE provides an active functional site on the liposomal surface for attachment.

The antibody conjugate can also be formulated to provide more than one active compound, e.g., additional chemotherapeutic or cytotoxic agents, cytokines, or growth inhibitory agents. The active ingredients may also prepared as sustained-release preparations (e.g., semi-permeable matrices of solid hydrophobic polymers (e.g., polyesters, hydrogels (for example, poly (2-hydroxyethyl-methacrylate), or poly (vinylalcohol)), polylactides. The antibodies and immunoconjugates can be entrapped in a nanoparticle prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions.

The CLL-1 antibodies described herein can kill CLL-1-expressing cells alone, or in combination with a cytotoxic agent. In some embodiments, the method of treatment comprises administering to an individual an effective amount of a therapeutic CLL-1 antibody or CLL-1 antibody conjugate, e.g., a CLL-1 antibody attached to a therapeutic agent. In some embodiments, the individual has been diagnosed with cancer, e.g., AML. In some embodiments, the individual is receiving or has received cancer therapy, e.g., surgery, radiotherapy, or chemotherapy. In some embodiments, the individual has been diagnosed, but the cancer is in remission.

In some embodiments, the method further comprises monitoring the individual for progression of the cancer. In some embodiments, the dose of the CLL-1 antibody or CLL-1 antibody conjugate for each administration is determined based on the therapeutic progress of the individual, e.g., where a higher dose of chemotherapeutic is administered if the individual is not responding sufficiently to therapy.

In some embodiments, the invention can include an antibody or antibody-targeted composition and a physiologically (i.e., pharmaceutically) acceptable carrier. The term "carrier" refers to a typically inert substance used as a diluent or vehicle for a diagnostic or therapeutic agent. The term also encompasses a typically inert substance that imparts cohesive qualities to the composition. Physiologically acceptable carriers can be liquid, e.g., physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Since physiologically acceptable carriers are determined in part by the particular composition being administered as well as by the particular method used to administer the composition, there are a wide variety of suitable formulations of pharmaceutical compositions of the present invention (See, e.g., Remington's Pharmaceutical Sciences, 17th ed., 1989).

The compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate. Sugars can also be included for stabilizing the compositions, such as a stabilizer for lyophilized antibody compositions.

Dosage forms can be prepared for mucosal (e.g., nasal, sublingual, vaginal, buccal, or rectal), parenteral (e.g., sub-cutaneous, intravenous, intramuscular, or intraarterial injection, either bolus or infusion), oral, or transdermal administration to a patient. Examples of dosage forms include, but are not limited to: dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Injectable (e.g., intravenous) compositions can comprise a solution of the antibody or antibody-targeted composition suspended in an acceptable carrier, such as an aqueous carrier. Any of a variety of aqueous carriers can be used, e.g., water, buffered water, 0.4% saline, 0.9% isotonic saline, 0.3% glycine, 5% dextrose, and the like, and may include glycoproteins for enhanced stability, such as albumin, lipoprotein, globulin, etc. Often, normal buffered saline (135-150 mM NaCl) will be used. The compositions can contain pharmaceutically acceptable auxiliary substances to approximate physiological conditions, such as pH adjusting and buffering agents, tonicity adjusting agents, wetting agents, e.g., sodium acetate, sodium lactate, sodium chloride, potassium chloride, calcium chloride, sorbitan monolaurate, triethanolamine oleate, etc. In some embodiments, the antibody-targeted composition can be formulated in a kit for intravenous administration.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The pharmaceutical preparation can be packaged or prepared in unit dosage form. In such form, the preparation is subdivided into unit doses containing appropriate quantities of the active component, e.g., according to the dose of the therapeutic agent or concentration of antibody. The unit dosage form can be a packaged preparation, the package containing discrete quantities of preparation, in unit-dose or multi-dose sealed containers, such as ampoules and vials. The composition can, if desired, also contain other compatible therapeutic agents.

The antibody (or antibody-targeted composition) can be administered by injection or infusion through any suitable route including but not limited to intravenous, subcutaneous, intramuscular or intraperitoneal routes. An example of administration of a pharmaceutical composition includes storing the antibody at 10 mg/ml in sterile isotonic aqueous saline solution for injection at 4° C., and diluting it in either 100 ml or 200 ml 0.9% sodium chloride for injection prior to administration to the patient. The antibody is administered by intravenous infusion over the course of 1 hour at a dose of between 0.2 and 10 mg/kg. In other embodiments, the antibody is administered by intravenous infusion over a period of between 15 minutes and 2 hours. In still other embodiments, the administration procedure is via sub-cutaneous bolus injection.

The dose of antibody is chosen in order to provide effective therapy for the patient and is in the range of less than 0.1 mg/kg body weight to about 25 mg/kg body weight or in the range 1 mg-2 g per patient. In some cases, the dose is in the range 1-100 mg/kg, or approximately 50 mg-8000 mg/patient. The dose may be repeated at an appropriate frequency which may be in the range once per day to once every three months, depending on the pharmacokinetics of the antibody (e.g., half-life of the antibody in the circulation) and the pharmacodynamic response (e.g., the duration of the therapeutic effect of the antibody). In some embodiments, the in vivo half-life of between about 7 and about 25 days and antibody dosing is repeated between once per week and once every 3 months.

Administration can be periodic. Depending on the route of administration, the dose can be administered, e.g., once every 1, 3, 5, 7, 10, 14, 21, or 28 days or longer (e.g., once every 2, 3, 4, or 6 months). In some cases, administration is more frequent, e.g., 2 or 3 times per day. The patient can be monitored to adjust the dosage and frequency of administration depending on therapeutic progress and any adverse side effects, as will be recognized by one of skill in the art.

Thus in some embodiments, additional administration is dependent on patient progress, e.g., the patient is monitored between administrations. For example, after the first administration or round of administrations, the patient can be monitored for rate of tumor growth, recurrence (e.g., in the case of a post-surgical patient), or general disease-related symptoms such as weakness, pain, nausea, etc.

For the treatment of cancer, an antibody or antibody-targeted composition (e.g., including a therapeutic and/or diagnostic agent) can be administered at the initial dosage of about 0.001 mg/kg to about 1000 mg/kg daily and adjusted over time. A daily dose range of about 0.01 mg/kg to about 500 mg/kg, or about 0.1 mg/kg to about 200 mg/kg, or about 1 mg/kg to about 100 mg/kg, about 5 to about 10 mg/kg, or about 10 mg/kg to about 50 mg/kg, can be used. The in vivo xenograft results described herein indicate that a dose between 5-20 mg antibody/kg body weight is effective for dramatic reduction of tumor growth.

The dosage is varied depending upon the requirements of the patient, the severity of the condition being treated, and the targeted composition being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a particular targeted composition in a particular patient, as will be recognized by the skilled practitioner.

VII. Examples

A. Example 1: Characterization of HuM26 Variants on 293-CLL1 Cells

Referring to FIG. 3: Binding of various M26 antibodies, ChiM26; VH4a+L4; VH4A+L4D and VH4A+L4DR to 293-CLL1 cells were analyzed at different antibody concentrations. 293-CLL1 cells were incubated with anti-CLL1 antibodies for 1 h at 4° C. After incubation, cells were washed/centrifuged and resuspended in PBS, then were incubated with goat-anti-human antibody-FITC conjugate. Cells were analyzed by flow cytometer and data process by Flowjo program. Isotype HuIgG1 as a non-binding control was also processed in parallel.

B. Example 2: Characterization of HuM26 Variants on Various AML Cell Lines ((i.e., HL-60, OCI-AML-5 and OCI-AMLS KO(CLL1-Knockout)

Referring to FIG. 4: AML5 cells with CLL1 knockout were generated by CRISPR/CAS technology. OCI-AMLS KO cells were enriched by FACS and grew in the same condition as parental OCI-AML-5 cells. HL-60, OCI-AMLS and OCI-AMLS KO cell lines were stained with various M26 antibodies, ChiM26; VH4a+L4; VH4A+L4D and VH4A+L4DR at different concentrations. After incubation, cells were washed/centrifuged and resuspended in PBS, then were incubated with goat-anti-human antibody-FITC conjugate. Cells were analyzed by flow cytometer and data processed by the Flowjo program. MFI plotted on y-axis is calculated from total MFI-minus MFI from non-binding Isotype HuIgG1 control.

C. Example 3: Characterization of HuM26 Binding to Rhesus MPC

Referring to FIG. 5: isolated Rhesus MPCs were stained with Alexa488-ChiM26, Alexa488-HuM26 and a non-binding Alexa488-HuIgG1 control. After incubation, cells were washed/centrifuged and resuspended in PBS. Cells were analyzed by flow cytometer and data processed by the Flowjo program.

D. Example 4: ELISA Analysis of the Binding of Transiently Expressed ChM31, M31-ChVH/HuVL1 and M31-ChVH/HuVL2 Antibodies to CLL1 His Tag Antigen Referring to FIG. 6: Binding of chimeric M26 and two versions of humanized M26 were compared. Each antibody was tested at various concentrations, starting at 250 ng/mL and serial 2-fold dilutions. Absorbance values (Y-axis) are plotted at each antibody concentration tested (X-axis) in the figure.

E. Example 5: ELISA Analysis of the Binding of Transiently Expressed ChM31, HuM31-VH1/VL2, HuM31-VH2/VL2, HuM31-VH3/VL2 and HuM31-VH4/VL2 Antibodies to CLL1 His Tag Antigen Referring to FIG. 7, Binding of chimeric M31 and three versions of humanized M31 were compared. Each antibody was tested at various concentrations, starting at 500 ng/mL and serial 2-fold dilutions. Absorbance values (Y-axis) are plotted at each antibody concentration tested (X-axis) in the figure.

F. Example 6: ELISA Analysis of the Binding of Purified ChM31, HuM31-VH2/VL2, HuM31-VH3/VL2 and HuM31-VH4/VL2 Antibodies to His Tag Antigen Referring to FIG. 8, each antibody was tested at various concentrations, starting at 1 μg/mL and serial 2-fold dilutions. Absorbance values (Y-axis) are plotted at each antibody concentration tested (X-axis) in the figure.

G. Example 7: Competitive Binding ELISA to Analyze the Affinity of ChM31, HuM31-VH2/VL2, HuM31-VH3/VL2 and HuM31-VH4/VL2 Antibodies to His Tag Antigen Referring to FIG. 9, binding of mouse M31 antibody in the presence of ChM31, HuM31-VH2/VL2, HuM31-VH3/VL2 or HuM31-VH4/VL2 antibody, starting at 25 μg/mL and serial 3-fold dilutions, was analyzed. Absorbance values (Y-axis) are plotted at each antibody concentration tested (X-axis) in the figure. IC50 values were calculated using GraphPad Prism.

H. Example 8: Competition Assay with HuM31 and ChiM31

Referring to FIG. 10, ChiM31 was labeled with Alexa488. 293-CLL1 cells were pre-incubated with 1 μg of labeled ChiM31, and then completed with various amount of ChiM31 and HuM31. FACS were performed and data were analyzed and EC50 were calculated.

I. Example 9: HuM31 and ChiM31 Binding Profile to Cyno PBMC

Referring to FIG. 11, PBMCs isolated from three Cynomolgus monkey peripheral blood samples by ficoll gradient and pooled. PBMCs (0.2×10^6 pooled) were blocked with 3% normal human serum and then stained with antibodies specific for Cynomolgus lineage markers. Live cells were gated for lineage markers. The lineage populations were gated for HuM31 and ChiM31.

J. Example 10—Preparation of C6-CLT-D202 (Antibody-Drug Conjugate)

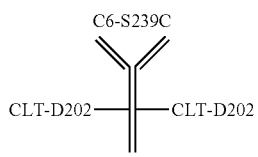

Details of Examples 10-15 can also be found in WO 2016/149646, which is incorporated by reference. A humanized, cys-substituted at position 239 anti-CLL1 antibody ("C6-S239C-CYSM26") (5.0 mg, 1.68 mg/mL, PBS) was exchanged into borate buffer (50 mM, pH 8.5, 1 mM diethylene triamine pentaacetic acid (DTPA)) via 2 cycles of molecular weight cut-off filtration (MWCO) using a Millipore, 15 mL, 30 kDa device. To the new solution of the C6-S239C-CYSMAB antibody (5.0 mg/mL, borate buffer (50 mM, pH 8.5, 1 mM DTPA)) was added a solution of Dithiothreitol (DTT) (33 µL, 50.0 equiv., 50 mM) and the resultant solution was shaken gently overnight.

```
Antibody C6 has the light chain variable
region sequence:
                                    (SEQ ID NO: 1)
DIQMTQSPSSLSASVGDRVTLTCRATQELSGYLSWLQQKPGKAIKRLIYA

ASTLDSGVPSRFSGNRAGTDYTLTISSLQPEDFATYYCLQYAIYPYTFGQ

GTKLEIK.

Antibody C6 has the heavy chain variable
region sequence:
                                    (SEQ ID NO: 7)
EVQLVQSGAEVKKPGASVKMSCKASGYTFTSYFIHWVRQAPGQGLEWIGF

INPYNDGSKYAQKFQGRATLTSDKSTSTVYMELSSLRSEDTAVYYCTRDD

GYYGYAMDYWGQGTLVTVSS.
```

Complete reduction of the interchain disulfide bridges and removal of the S239C cysteine/glutathione adducts were was confirmed by rp-LCMS as described earlier (Junutula et al., 2008, Nature Biotech, 26, 925-932). DTT was then removed from the solution via 3 cycles of molecular weight cut-off filtration (MWCO) using a Millipore, 15 mL, 30 kDa device, using PBS as the exchange buffer. To a 5 mg/ml solution of the fully reduced C6-S239C-CYSMAB antibody was added a solution of dehydro ascorbic acid (dhAA) (33 µL, 50.0 equiv., 50 mM). The resultant solution was shaken gently for 3 hrs. The re-oxidation was monitored via rp-LCMS. Once the re-oxidation was deemed complete, the reaction mixture was diluted up to 50% v/v with propylene glycol and CLT-D202 (18, FIG. 12D) was added as a solution in DMSO (10.0 equiv., 10 mM in DMSO). The reaction was allowed to stir at ambient temperature for 1 hr. The mixture was then treated with activated charcoal for 1 hr at ambient temperature. The activated charcoal was then removed via filtration. The conjugate was then exchanged into PBS via multiple cycles of molecular weight cut-off filtration (MWCO) using Millipore, 15 mL, 30 kDa devices. The solution was then subjected to a sterile filtration to yield the desired conjugate (0.974 mL, 2.16 mg/mL). Volume: 0.974 mL. Concentration: 2.16 mg/mL (A280=0.145, 20-fold dilution). Drug to Antibody Ratio (DAR): 1.7 (determined by rp-LCMS). The monomeric form of ADC is confirmed by size exclusion chromatography (SEC): 96%.

K. Example 11—Preparation of C0-CLT-D202 Antibody-Drug Conjugate (ADC)

Palivizumab was used a control antibody, C0. C0 antibody is a non-binding control IgG1. An ADC with C0 and CLT-D202 was The C0 antibody (12.0 mg, 100 mg/mL, PBS) was diluted to 5 mg/mL using borate buffer (50 mM, pH 8.5, 1 mM DTPA). In order to conjugate CLT-D202, the hinge disulfides were reduced, as follows. To the new solution of the C0 antibody (@ 5.0 mg/mL, borate buffer (50 mM, pH 8.5, 1 mM DTPA)) was added a solution of tris(2-carboxyethyl)phosphine (TCEP) (136 µL, 1.7 equiv., 1 mM) and the resultant solution was shaken gently at 37° C. for 1 hr. The reaction was then cooled to ambient temperature and was diluted up to 50% v/v with propylene glycol at which point CLT-D202 (18, FIG. 12D) was added as a solution in DMSO (12.0 equiv., 10 mM in DMSO). The reaction was allowed to stir at ambient temperature for 1 hr. The mixture was then treated with activated charcoal for 1 hr at ambient temperature. The activated charcoal was then removed via filtration. The conjugate was then exchanged into PBS via PD-10 gel filtration (GE Healthcare). The combined fractions were concentrated using molecular weight cut-off filtration (MWCO) with Millipore, 15 mL, 30 kDa devices. The solution was then subjected to a sterile filtration to yield the desired conjugate (3.144 mL, 3.2 mg/mL). Volume: 3.144 mL. Concentration: 3.2 mg/mL (A280=0.237, 20-fold dilution). Drug to Antibody Ratio (DAR): 2.6 (determined by rp-LCMS). The monomeric form of ADC is confirmed by SEC: 87%.

L. Example 12—C6-CLT-D202 ADC Selective Cytotoxicity

The selectivity of the C6-CLT-D202 ADC is shown in FIGS. 13A-13B. HL-60 cells (human promyelocytic leukemia cells) which express CLL-1 in the range of about 30,000-50,000 copy number per cell, were treated with the CLL-1 selective cytotoxic antibody-drug conjugate, C6-CLT-D202 ADC and the control antibody-drug conjugate, C0-CLT-D202 ADC, at varying concentrations at 37° C. for five days. FIG. 13A shows target dependent cell killing by C6-CLT-D202 ADC relative to that of the control C0-CLT-D202 ADC by over 500 fold. FIG. 13B shows that for non-CLL-1 expressing cell lines such as TF1 (human erythroleukemic cell line), both C6-CLT-D202 ADC and C-CLT-D202 ADC had similar, non-cytotoxic effect, thus demonstrating the selectivity of the CLL-1 targeted C6-CLT-D202 ADC in vitro.

M. Example 13—C6-CLT-D202 ADC Target Dependent Cytotoxicity

TF1 is a multi-drug resistant (MDR) positive acute myeloid leukemia (AML) cell line. CLL-1 was overexpressed in TF1 to demonstrate the potency of an antibody-drug conjugate comprising an anti-CLL1 antibody ("CLL1-ADC" or, more specifically, "C6-CLT-D202 ADC"). As shown in FIGS. 14A and 14B, the over-expressing TFI cell line (TF1-CLL1) and the standard TF1 cell line were treated at 37C at various concentrations with C6-CLT-D202 ADC and C0-CLT-D202 ADC, respectively. In FIG. 14A, the CLL-1 targeted C6-CLT-D202 ADC was shown to be potently cytotoxic to the TF1 CLL-1 MDR (+) line, while the control C0-CLT-D202 ADC had a much less potent effect. The activity against the standard TF1 cell line for each ADC are shown in FIG. 14B, where it is seen that both the C6-CLT-D202 ADC and C0-CLT-D202 ADC had more similar effect. The $IC_{50}$ results shown in Table 3 demonstrate the significant difference in cell killing effect when CLL-1 is expressed in a tumor cell target, providing a decrease in IC50 by a factor of about $10^3$.

TABLE 2

| IC50 for selected ADCs against TF1 CLL-1 and TF1 cell lines. | | |
|---|---|---|
| $IC_{50}$ ug/mL | C0-D202 | C6-D202 |
| TF1-CLL1 | 23.27 | 0.008 |
| TF1 | 12.93 | 9.47 |

N. Example 14—Correlation Between Binding and Cytotoxicity for C6-CLT-D202 ADC The correlation between binding to cells and ability to kill targeted cells was examined. In Table 4, the first column of numbers is the ratio of the mean fluorescent intensity of binding of C6-CLT-D202 ADC to each specific cell line, relative to the mean fluorescent intensity of binding of C0-CLT-D202 ADC, which is the control ADC. A larger ratio of MFI reflects increased binding of the targeted ADC over that of the control ADC. The second column shows the IC50 (ng/mL) for C6-CLT-D202 ADC for the specified cell line. In FIG. 15, the two numbers are mapped, the log of the relative mean fluorescent index (MFI) along the X axis and the log of the IC50 value along the Y axis, for each cell line. FIG. 15 shows good correlation of relative binding vs cell killing, where $R^2$ of the fit of line shown is 0.701. This demonstrates that C6-CLT-D202 has good target-dependent cytotoxic activity across many cell lines associated with AML disease.

TABLE 3

Cell lines, Relative Binding Intensity, and $IC_{50}$s.

| Cell line | C6 relative MFI C6/C0 | C6-D202 IC50 ng/mL |
| --- | --- | --- |
| AML2 | 13 | 3 |
| HL-60 | 20 | 11 |
| AML5 | 15 | 13 |
| AML5KO | 1.3 | 6621 |
| 293 | 1.2 | 14270 |
| U937 | 14.7 | 11690 |
| SHI-1 | 1.4 | 5670 |
| KG-1a | 1.3 | 82760 |
| HEL92.1.7 | 1.3 | 50000 |
| HEL92.1.7-CLL1 | 26.1 | 17 |
| HNT-34 | 5.8 | 3500 |
| TF1 | 1.5 | 22230 |
| EOL-1 | 20.5 | 13.7 |
| PL21 | 14.7 | 199 |

O. Example 15—C6-CLT-D202 ADC Targets Both Proliferating and Quiescent Cells

AML-5 cells, which express CLL-1, are cultured under either proliferative or quiescent conditions for a period of five (5) days. During this period, one set of proliferative CLL-1-expressing cells was treated with varying concentrations of C6-CLT-202 ADC. A second set of proliferative CLL-1-expressing cells was treated with isotype control. A respective set of quiescent CLL-1-expressing cells were treated accordingly with either C6-CLT-D202 or isotype control. FIG. 16A shows that C6-CLT-D202 was effective at killing CLL-1-expressing cells at an IC50 of 0.03 ug/mL (proliferating) and 0.02 ug/mL (quiescent) cells, while the isotype control had an IC50 of at least 100-fold higher concentration. Quiescent cell killing increases with increasing incubation times.

In contrast, as shown in FIG. 16B, when CLL-1-knockout cells were subjected to the same conditions, the target dependent cytotoxic effect of C6-CLT-D202 ADC is eliminated. The IC50s for both proliferating and quiescent AML-5 cells are similar to that of the isotype control, in the range of 2.34 ug/mL (quiescent) and 5.54 ug/mL (proliferating).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entireties for all purposes.

What is claimed is:

1. An antibody that binds CLL-1, the antibody comprising a variable light chain comprising SEQ ID NO: 21 followed by further framework sequence SEQ ID NO: 22; and a variable heavy chain comprising SEQ ID NO: 23 followed by further framework sequence SEQ ID NO: 24.

2. The antibody of claim 1, wherein the variable light chain comprises SEQ ID NO: 2, and the variable heavy chain comprises SEQ ID NO:8.

3. The antibody of claim 1, wherein the variable light chain comprises SEQ ID NO: 3, and the variable heavy chain comprises SEQ ID NO:8.

4. The antibody of claim 1, wherein the variable light chain comprises SEQ ID NO:4, and the variable heavy chain comprises SEQ ID NO:8.

5. The antibody of claim 1, wherein the variable light chain comprises SEQ ID NO:5, and the variable heavy chain comprises SEQ ID NO:8.

6. The antibody of claim 1, wherein the antibody comprises an scFv.

7. The antibody of claim 1, wherein the antibody is a bi-specific antibody comprising a first arm that binds CLL-1 and a second arm that binds a second target antigen selected from the group consisting of CD33, CD123, IL1Rap, GPR114, and CD3 antigen on T cells.

8. The antibody of claim 1, linked to a cytotoxic agent.

9. The antibody of claim 8, wherein the cytotoxic agent is a benzodiazepine.

10. The antibody of claim 9, wherein the benzodiazepine is selected from a pyrrolo benzodiazepine, an indolino benzodiazepine and an isoquinolidinobenzodiazepine, or a hetero dimer or homo dimer thereof.

11. The antibody of claim 1, further comprising a human constant region selected from IgG1, IgG2, IgG3 and IgG4.

12. The antibody of claim 1, which is a constant region cysteine-substituted antibody.

* * * * *

SEQUENCE LISTING

<160> NUMBER OF SEQ ID NOS: 27

<210> SEQ ID NO 1
<211> LENGTH: 107
<212> TYPE: PRT
<213> ORGANISM: Artificial Sequence
<220> FEATURE:
<223> OTHER INFORMATION: Synthetic polypeptide construct

<400> SEQUENCE: 1

Asp Ile Gln Met Thr Gln Ser Pro Ser Ser Leu Ser Ala Ser Leu Gly
1               5                   10                  15

Glu Arg Val Ser Leu Thr Cys Arg Ala Thr Gln Glu Leu Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Asn Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ile Tyr Pro Tyr
                85                  90                  95

Thr Phe Gly Gly Gly Thr Lys Leu Glu Ile Lys
            100                 105

<210> SEQ ID NO 2

```
<211> LENGTH: 107
<212> TYPE: PRT
<213> ORGANISM: Artificial Sequence
<220> FEATURE:
<223> OTHER INFORMATION: Synthetic polypeptide construct

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Glu Leu Ser Gly Tyr
            20                  25                  30

Leu Ser Trp Phe Gln Gln Lys Pro Gly Lys Ala Pro Lys Ser Leu Ile
        35                  40                  45

Tyr Ala Ala Ser Thr Leu Asp Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ala Ile Tyr Pro Tyr
                85                  90                  95

Thr Phe Gly Gln Gly Thr Lys Leu Glu Ile Lys
            100                 105

<210> SEQ ID NO 3
<211> LENGTH: 107
<212> TYPE: PRT
<213> ORGANISM: Artificial Sequence
<220> FEATURE:
<223> OTHER INFORMATION: Synthetic polypeptide construct

<400> SEQUENCE: 3

Asp Ile Gln Met Thr Gln Ser Pro Ser Ser Leu Ser Ala Ser Val Gly
1               5                   10                  15

Asp Arg Val Thr Leu Thr Cys Arg Ala Thr Gln Glu Leu Ser Gly Tyr
            20                  25                  30

Leu Ser Trp Leu Gln Gln Lys Pro Gly Lys Ala Ile Lys Arg Leu Ile
        35                  40                  45

Tyr Ala Ala Ser Thr Leu Asp Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Ala Ile Tyr Pro Tyr
                85                  90                  95

Thr Phe Gly Gln Gly Thr Lys Leu Glu Ile Lys
            100                 105

<210> SEQ ID NO 4
<211> LENGTH: 107
<212> TYPE: PRT
<213> ORGANISM: Artificial Sequence
<220> FEATURE:
<223> OTHER INFORMATION: Synthetic polypeptide construct

<400> SEQUENCE: 4

Asp Ile Gln Met Thr Gln Ser Pro Ser Ser Leu Ser Ala Ser Val Gly
1               5                   10                  15

Asp Arg Val Thr Leu Thr Cys Arg Ala Thr Gln Glu Leu Ser Gly Tyr
            20                  25                  30

Leu Ser Trp Leu Gln Gln Lys Pro Gly Lys Ala Ile Lys Arg Leu Ile
        35                  40                  45
```

```
Tyr Ala Ala Ser Thr Leu Asp Ser Gly Val Pro Ser Arg Phe Ser Gly
        50                  55                  60

Asn Gly Ala Gly Thr Asp Tyr Thr Leu Thr Ile Ser Ser Leu Gln Pro
65                  70                  75                  80

Glu Asp Phe Ala Thr Tyr Tyr Cys Leu Gln Tyr Ala Ile Tyr Pro Tyr
                85                  90                  95

Thr Phe Gly Gln Gly Thr Lys Leu Glu Ile Lys
                100                 105

<210> SEQ ID NO 5
<211> LENGTH: 107
<212> TYPE: PRT
<213> ORGANISM: Artificial Sequence
<220> FEATURE:
<223> OTHER INFORMATION: Synthetic polypeptide construct

<400> SEQUENCE: 5

Asp Ile Gln Met Thr Gln Ser Pro Ser Ser Leu Ser Ala Ser Val Gly
1               5                   10                  15

Asp Arg Val Thr Leu Thr Cys Arg Ala Thr Gln Glu Leu Ser Gly Tyr
            20                  25                  30

Leu Ser Trp Leu Gln Gln Lys Pro Gly Lys Ala Ile Lys Arg Leu Ile
        35                  40                  45

Tyr Ala Ala Ser Thr Leu Asp Ser Gly Val Pro Ser Arg Phe Ser Gly
    50                  55                  60

Asn Arg Ala Gly Thr Asp Tyr Thr Leu Thr Ile Ser Ser Leu Gln Pro
65                  70                  75                  80

Glu Asp Phe Ala Thr Tyr Tyr Cys Leu Gln Tyr Ala Ile Tyr Pro Tyr
                85                  90                  95

Thr Phe Gly Gln Gly Thr Lys Leu Glu Ile Lys
                100                 105

<210> SEQ ID NO 6
<211> LENGTH: 70
<212> TYPE: PRT
<213> ORGANISM: Artificial Sequence
<220> FEATURE:
<223> OTHER INFORMATION: Synthetic polypeptide construct

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Trp Phe Gln Gln Lys Pro Gly Lys Ala
            20                  25                  30

Pro Lys Ser Leu Ile Tyr Gly Val Pro Ser Arg Phe Ser Gly Ser Gly
        35                  40                  45

Ser Gly Thr Asp Phe Thr Leu Thr Ile Ser Ser Leu Gln Pro Glu Asp
    50                  55                  60

Phe Ala Thr Tyr Tyr Cys
65                  70

<210> SEQ ID NO 7
<211> LENGTH: 120
<212> TYPE: PRT
<213> ORGANISM: Artificial Sequence
<220> FEATURE:
<223> OTHER INFORMATION: Synthetic polypeptide construct

<400> SEQUENCE: 7

Glu Val Gln Leu Gln Gln Ser Gly Pro Glu Leu Val Lys Pro Gly Ala
```

```
                1               5                   10                  15
Ser Val Lys Met Ser Cys Lys Ala Ser Gly Tyr Thr Phe Thr Ser Tyr
                20                  25                  30

Phe Ile His Trp Val Lys Gln Lys Pro Gly Gln Gly Leu Glu Trp Ile
            35                  40                  45

Gly Phe Ile Asn Pro Tyr Asn Asp Gly Ser Lys Tyr Asn Glu Lys Phe
        50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Arg Asp Asp Gly Tyr Tyr Gly Tyr Ala Met Asp Tyr Trp Gly Gln
                100                 105                 110

Gly Thr Leu Val Thr Val Ser Ser
            115                 120
```

<210> SEQ ID NO 8
<211> LENGTH: 120
<212> TYPE: PRT
<213> ORGANISM: Artificial Sequence
<220> FEATURE:
<223> OTHER INFORMATION: Synthetic polypeptide construct

<400> SEQUENCE: 8

```
Glu Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
                20                  25                  30

Phe Ile His Trp Val Arg Gln Ala Pro Gly Gln Gly Leu Glu Trp Ile
            35                  40                  45

Gly Phe Ile Asn Pro Tyr Asn Asp Gly Ser Lys Tyr Ala Gln Lys Phe
        50                  55                  60

Gln Gly Arg Ala Thr Leu Thr Ser Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Asp Asp Gly Tyr Tyr Gly Tyr Ala Met Asp Tyr Trp Gly Gln
                100                 105                 110

Gly Thr Leu Val Thr Val Ser Ser
            115                 120
```

<210> SEQ ID NO 9
<211> LENGTH: 78
<212> TYPE: PRT
<213> ORGANISM: Artificial Sequence
<220> FEATURE:
<223> OTHER INFORMATION: Synthetic polypeptide construct

<400> SEQUENCE: 9

```
Gln Val Gln Leu Val Gln Ser Gly Ala Glu Val Lys Lys Pro Gly Ala
1               5                   10                  15

Ser Val Lys Val Ser Cys Lys Ala Ser Trp Val Arg Gln Ala Pro Gly
                20                  25                  30

Gln Gly Leu Glu Trp Met Gly Tyr Ala Gln Lys Phe Gln Gly Arg Val
            35                  40                  45

Thr Met Thr Arg Asp Thr Ser Thr Ser Thr Val Tyr Met Glu Leu Ser
        50                  55                  60
```

Ser Leu Arg Ser Glu Asp Thr Ala Val Tyr Tyr Cys Ala Arg
65                  70                  75

<210> SEQ ID NO 10
<211> LENGTH: 111
<212> TYPE: PRT
<213> ORGANISM: Artificial Sequence
<220> FEATURE:
<223> OTHER INFORMATION: Synthetic polypeptide construct

<400> SEQUENCE: 10

Thr Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Tyr Asp Pro Trp Thr Phe Gly Gly Gly Thr Lys Leu Glu Ile Lys
            100                 105                 110

<210> SEQ ID NO 11
<211> LENGTH: 111
<212> TYPE: PRT
<213> ORGANISM: Artificial Sequence
<220> FEATURE:
<223> OTHER INFORMATION: Synthetic polypeptide construct

<400> SEQUENCE: 11

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Tyr Asp Pro Trp Thr Phe Gly Gly Gly Thr Lys Leu Glu Ile Lys
            100                 105                 110

<210> SEQ ID NO 12
<211> LENGTH: 111
<212> TYPE: PRT
<213> ORGANISM: Artificial Sequence
<220> FEATURE:
<223> OTHER INFORMATION: Synthetic polypeptide construct

<400> SEQUENCE: 12

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Ser Tyr

```
                    20                  25                  30

Gly Asn Ser Phe Met His Trp Tyr Gln Gln Lys Pro Gly Gln Pro
            35                  40                  45

Lys Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Thr Ile Asp
 65                  70                  75                  80

Pro Val Glu Ala Asp Asp Ala Ala Thr Tyr Tyr Cys Gln Gln Asn Asn
                85                  90                  95

Tyr Asp Pro Trp Thr Phe Gly Gly Gly Thr Lys Leu Glu Ile Lys
            100                 105                 110

<210> SEQ ID NO 13
<211> LENGTH: 79
<212> TYPE: PRT
<213> ORGANISM: Artificial Sequence
<220> FEATURE:
<223> OTHER INFORMATION: Synthetic polypeptide construct

<400> SEQUENCE: 13

Asp Ile Val Met Thr Gln Ser Pro Asp Ser Leu Ala Val Ser Leu Gly
 1               5                  10                  15

Glu Arg Ala Thr Ile Asn Cys Trp Tyr Gln Gln Lys Pro Gly Gln Pro
                20                  25                  30

Pro Lys Leu Leu Ile Tyr Gly Val Pro Ala Arg Phe Ser Gly Ser Gly
            35                  40                  45

Ser Gly Thr Asp Phe Thr Leu Thr Ile Asp Pro Val Glu Ala Asp Asp
        50                  55                  60

Ala Ala Thr Tyr Tyr Cys Gly Gly Gly Thr Lys Leu Glu Ile Lys
 65                  70                  75

<210> SEQ ID NO 14
<211> LENGTH: 120
<212> TYPE: PRT
<213> ORGANISM: Artificial Sequence
<220> FEATURE:
<223> OTHER INFORMATION: Synthetic polypeptide construct

<400> SEQUENCE: 14

Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
        50                  55                  60

Lys Gly Lys Ala Thr Leu Thr Ser Asp Thr Ser Ser Thr Ala Tyr
 65                  70                  75                  80

Met Glu Leu Asn Ser Leu Thr Ser Glu Asp Ser Ala Val Tyr Phe Cys
                85                  90                  95

Ala Arg Pro Ile Tyr Phe Asp Asn Asp Tyr Phe Asp Tyr Trp Gly Gln
            100                 105                 110

Gly Thr Thr Leu Lys Val Ser Ser
            115                 120

<210> SEQ ID NO 15
<211> LENGTH: 120
```

```
<212> TYPE: PRT
<213> ORGANISM: Artificial Sequence
<220> FEATURE:
<223> OTHER INFORMATION: Synthetic polypeptide construct

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Val Met His Trp Val Arg Gln Ala Pro Gly Gln Arg Leu Glu Trp Ile
            35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Pro Ile Tyr Phe Asp Asn Asp Tyr Phe Asp Tyr Trp Gly Gln
                100                 105                 110

Gly Thr Thr Val Thr Val Ser Ser
            115                 120

<210> SEQ ID NO 16
<211> LENGTH: 120
<212> TYPE: PRT
<213> ORGANISM: Artificial Sequence
<220> FEATURE:
<223> OTHER INFORMATION: Synthetic polypeptide construct

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Val Met His Trp Val Arg Gln Ala Pro Gly Gln Arg Leu Glu Trp Ile
            35                  40                  45

Gly Tyr Ile Asn Pro Tyr Asn Asp Gly Thr Lys Tyr Asn Glu Lys Phe
    50                  55                  60

Lys Gly Arg Ala Thr Leu Thr Ser Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Pro Ile Tyr Phe Asp Asn Asp Tyr Phe Asp Tyr Trp Gly Gln
                100                 105                 110

Gly Thr Thr Val Thr Val Ser Ser
            115                 120

<210> SEQ ID NO 17
<211> LENGTH: 120
<212> TYPE: PRT
<213> ORGANISM: Artificial Sequence
<220> FEATURE:
<223> OTHER INFORMATION: Synthetic polypeptide construct

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
            20                  25                  30
Val Met His Trp Val Arg Gln Ala Pro Gly Arg Arg Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Ile Tyr Phe Asp Asn Asp Tyr Phe Asp Tyr Trp Gly Gln
            100                 105                 110

Gly Thr Leu Val Thr Val Ser Ser
            115                 120

<210> SEQ ID NO 18
<211> LENGTH: 120
<212> TYPE: PRT
<213> ORGANISM: Artificial Sequence
<220> FEATURE:
<223> OTHER INFORMATION: Synthetic polypeptide construct

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Arg Arg Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Arg Val Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Ile Tyr Phe Asp Asn Asp Tyr Phe Asp Tyr Trp Gly Gln
            100                 105                 110

Gly Thr Leu Val Thr Val Ser Ser
            115                 120

<210> SEQ ID NO 19
<211> LENGTH: 82
<212> TYPE: PRT
<213> ORGANISM: Artificial Sequence
<220> FEATURE:
<223> OTHER INFORMATION: Synthetic polypeptide construct

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Trp Val Arg Gln Ala Pro Gly
            20                  25                  30

Gln Arg Leu Glu Trp Met Gly Arg Val Thr Met Thr Arg Asp Thr Ser
        35                  40                  45

Ala Ser Thr Ala Tyr Met Glu Leu Ser Ser Leu Arg Ser Asp Asp Thr
    50                  55                  60

Ala Val Tyr Tyr Cys Ala Arg Trp Gly Gln Gly Thr Leu Val Thr Val
65                  70                  75                  80
```

Ser Ser

<210> SEQ ID NO 20
<211> LENGTH: 82
<212> TYPE: PRT
<213> ORGANISM: Artificial Sequence
<220> FEATURE:
<223> OTHER INFORMATION: Synthetic polypeptide construct

<400> SEQUENCE: 20

```
Gln Val Gln Leu Val Gln Ser Gly Ala Glu Val Lys Lys Pro Gly Ala
1               5                   10                  15

Ser Val Lys Val Ser Cys Lys Ala Ser Trp Val Arg Gln Ala Pro Gly
            20                  25                  30

Gln Arg Leu Glu Trp Met Gly Arg Val Thr Ile Thr Arg Asp Thr Ser
        35                  40                  45

Ala Ser Thr Ala Tyr Met Glu Leu Ser Ser Leu Arg Ser Glu Asp Thr
    50                  55                  60

Ala Val Tyr Tyr Cys Ala Arg Trp Gly Gln Gly Thr Leu Val Thr Val
65                  70                  75                  80

Ser Ser
```

<210> SEQ ID NO 21
<211> LENGTH: 97
<212> TYPE: PRT
<213> ORGANISM: Artificial Sequence
<220> FEATURE:
<223> OTHER INFORMATION: Synthetic polypeptide construct
<220> FEATURE:
<221> NAME/KEY: MISC_FEATURE
<222> LOCATION: (21)..(21)
<223> OTHER INFORMATION: Xaa is Ile or Leu
<220> FEATURE:
<221> NAME/KEY: MISC_FEATURE
<222> LOCATION: (36)..(36)
<223> OTHER INFORMATION: Xaa is Phe or Leu
<220> FEATURE:
<221> NAME/KEY: MISC_FEATURE
<222> LOCATION: (44)..(44)
<223> OTHER INFORMATION: Xaa is Pro or Ile
<220> FEATURE:
<221> NAME/KEY: MISC_FEATURE
<222> LOCATION: (46)..(46)
<223> OTHER INFORMATION: Xaa is Ser or Arg
<220> FEATURE:
<221> NAME/KEY: MISC_FEATURE
<222> LOCATION: (65)..(65)
<223> OTHER INFORMATION: Xaa is Ser or Asn
<220> FEATURE:
<221> NAME/KEY: MISC_FEATURE
<222> LOCATION: (66)..(66)
<223> OTHER INFORMATION: Xaa is Gly or Arg
<220> FEATURE:
<221> NAME/KEY: MISC_FEATURE
<222> LOCATION: (67)..(67)
<223> OTHER INFORMATION: Xaa is Ser or Ala
<220> FEATURE:
<221> NAME/KEY: MISC_FEATURE
<222> LOCATION: (71)..(71)
<223> OTHER INFORMATION: Xaa is Phe or Tyr

<400> SEQUENCE: 21

```
Asp Ile Gln Met Thr Gln Ser Pro Ser Ser Leu Ser Ala Ser Val Gly
1               5                   10                  15

Asp Arg Val Thr Xaa Thr Cys Arg Ala Thr Gln Glu Leu Ser Gly Tyr
            20                  25                  30

Leu Ser Trp Xaa Gln Gln Lys Pro Gly Lys Ala Xaa Lys Xaa Leu Ile
        35                  40                  45
```

```
Tyr Ala Ala Ser Thr Leu Asp Ser Gly Val Pro Ser Arg Phe Ser Gly
         50                  55                  60

Xaa Xaa Xaa Gly Thr Asp Xaa Thr Leu Thr Ile Ser Ser Leu Gln Pro
 65                  70                  75                  80

Glu Asp Phe Ala Thr Tyr Tyr Cys Leu Gln Tyr Ala Ile Tyr Pro Tyr
                 85                  90                  95

Thr

<210> SEQ ID NO 22
<211> LENGTH: 10
<212> TYPE: PRT
<213> ORGANISM: Artificial Sequence
<220> FEATURE:
<223> OTHER INFORMATION: Synthetic polypeptide construct

<400> SEQUENCE: 22

Phe Gly Gln Gly Thr Lys Leu Glu Ile Lys
1               5                   10

<210> SEQ ID NO 23
<211> LENGTH: 109
<212> TYPE: PRT
<213> ORGANISM: Artificial Sequence
<220> FEATURE:
<223> OTHER INFORMATION: Synthetic polypeptide construct
<220> FEATURE:
<221> NAME/KEY: MISC_FEATURE
<222> LOCATION: (1)..(1)
<223> OTHER INFORMATION: Xaa is Gln or Glu
<220> FEATURE:
<221> NAME/KEY: MISC_FEATURE
<222> LOCATION: (20)..(20)
<223> OTHER INFORMATION: Xaa is Val or Met
<220> FEATURE:
<221> NAME/KEY: MISC_FEATURE
<222> LOCATION: (48)..(48)
<223> OTHER INFORMATION: Xaa is Met or Ile
<220> FEATURE:
<221> NAME/KEY: MISC_FEATURE
<222> LOCATION: (68)..(68)
<223> OTHER INFORMATION: Xaa is Val or Ala
<220> FEATURE:
<221> NAME/KEY: MISC_FEATURE
<222> LOCATION: (70)..(70)
<223> OTHER INFORMATION: Xaa is Met or Leu
<220> FEATURE:
<221> NAME/KEY: MISC_FEATURE
<222> LOCATION: (72)..(72)
<223> OTHER INFORMATION: Xaa is Arg or Ser
<220> FEATURE:
<221> NAME/KEY: MISC_FEATURE
<222> LOCATION: (74)..(74)
<223> OTHER INFORMATION: Xaa is Thr or Lys
<220> FEATURE:
<221> NAME/KEY: MISC_FEATURE
<222> LOCATION: (97)..(97)
<223> OTHER INFORMATION: Xaa is Ala or Thr

<400> SEQUENCE: 23

Xaa Val Gln Leu Val Gln Ser Gly Ala Glu Val Lys Lys Pro Gly Ala
1               5                   10                  15

Ser Val Lys Xaa Ser Cys Lys Ala Ser Gly Tyr Thr Phe Thr Ser Tyr
                20                  25                  30

Phe Ile His Trp Val Arg Gln Ala Pro Gly Gln Gly Leu Glu Trp Xaa
             35                  40                  45

Gly Phe Ile Asn Pro Tyr Asn Asp Gly Ser Lys Tyr Ala Gln Lys Phe
         50                  55                  60
```

Gln Gly Arg Xaa Thr Xaa Thr Xaa Asp Xaa Ser Thr Ser Thr Val Tyr
65                  70                  75                  80

Met Glu Leu Ser Ser Leu Arg Ser Glu Asp Thr Ala Val Tyr Tyr Cys
                85                  90                  95

Xaa Arg Asp Asp Gly Tyr Tyr Gly Tyr Ala Met Asp Tyr
                100                 105

<210> SEQ ID NO 24
<211> LENGTH: 11
<212> TYPE: PRT
<213> ORGANISM: Artificial Sequence
<220> FEATURE:
<223> OTHER INFORMATION: Synthetic polypeptide construct

<400> SEQUENCE: 24

Trp Gly Gln Gly Thr Leu Val Thr Val Ser Ser
1               5                   10

<210> SEQ ID NO 25
<211> LENGTH: 111
<212> TYPE: PRT
<213> ORGANISM: Artificial Sequence
<220> FEATURE:
<223> OTHER INFORMATION: Synthetic polypeptide construct
<220> FEATURE:
<221> NAME/KEY: MISC_FEATURE
<222> LOCATION: (64)..(64)
<223> OTHER INFORMATION: Xaa is Ala or Asp
<220> FEATURE:
<221> NAME/KEY: MISC_FEATURE
<222> LOCATION: (72)..(72)
<223> OTHER INFORMATION: Xaa is Gly or Arg

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Ser Tyr
                20                  25                  30

Gly Asn Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Xaa
    50                  55                  60

Arg Phe Ser Gly Ser Gly Ser Xaa Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Tyr Asp Pro Trp Thr Phe Gly Gly Gly Thr Lys Leu Glu Ile Lys
                100                 105                 110

<210> SEQ ID NO 26
<211> LENGTH: 120
<212> TYPE: PRT
<213> ORGANISM: Artificial Sequence
<220> FEATURE:
<223> OTHER INFORMATION: Synthetic polypeptide construct
<220> FEATURE:
<221> NAME/KEY: MISC_FEATURE
<222> LOCATION: (43)..(43)
<223> OTHER INFORMATION: Xaa is Gln or Arg
<220> FEATURE:
<221> NAME/KEY: MISC_FEATURE
<222> LOCATION: (67)..(67)
<223> OTHER INFORMATION: Xaa is Arg or Lys
<220> FEATURE:
<221> NAME/KEY: MISC_FEATURE
<222> LOCATION: (68)..(68)

```
<223> OTHER INFORMATION: Xaa is Val or Ala
<220> FEATURE:
<221> NAME/KEY: MISC_FEATURE
<222> LOCATION: (70)..(70)
<223> OTHER INFORMATION: Xaa is Leu or Ile
<220> FEATURE:
<221> NAME/KEY: MISC_FEATURE
<222> LOCATION: (76)..(76)
<223> OTHER INFORMATION: Xaa is Ala or Thr
<220> FEATURE:
<221> NAME/KEY: MISC_FEATURE
<222> LOCATION: (84)..(84)
<223> OTHER INFORMATION: Xaa is Ser or Arg
<220> FEATURE:
<221> NAME/KEY: MISC_FEATURE
<222> LOCATION: (89)..(89)
<223> OTHER INFORMATION: Xaa is Asp or Glu
<220> FEATURE:
<221> NAME/KEY: MISC_FEATURE
<222> LOCATION: (115)..(115)
<223> OTHER INFORMATION: Xaa is Leu or Thr

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Xaa Arg Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Xaa Xaa Thr Xaa Thr Ser Asp Thr Ser Xaa Ser Thr Ala Tyr
65                  70                  75                  80

Met Glu Leu Xaa Ser Leu Arg Ser Xaa Asp Thr Ala Val Tyr Tyr Cys
            85                  90                  95

Ala Arg Pro Ile Tyr Phe Asp Asn Asp Tyr Phe Asp Tyr Trp Gly Gln
            100                 105                 110

Gly Thr Xaa Val Thr Val Ser Ser
        115                 120

<210> SEQ ID NO 27
<211> LENGTH: 120
<212> TYPE: PRT
<213> ORGANISM: Artificial Sequence
<220> FEATURE:
<223> OTHER INFORMATION: Synthetic polypeptide construct
<220> FEATURE:
<221> NAME/KEY: MISC_FEATURE
<222> LOCATION: (43)..(43)
<223> OTHER INFORMATION: Xaa is Gln or Arg
<220> FEATURE:
<221> NAME/KEY: MISC_FEATURE
<222> LOCATION: (48)..(48)
<223> OTHER INFORMATION: Xaa is Met or Ile
<220> FEATURE:
<221> NAME/KEY: MISC_FEATURE
<222> LOCATION: (67)..(67)
<223> OTHER INFORMATION: Xaa is Arg or Lys
<220> FEATURE:
<221> NAME/KEY: MISC_FEATURE
<222> LOCATION: (68)..(68)
<223> OTHER INFORMATION: Xaa is Val or Ala
<220> FEATURE:
<221> NAME/KEY: MISC_FEATURE
<222> LOCATION: (70)..(70)
<223> OTHER INFORMATION: Xaa is Ile or Leu
<220> FEATURE:
<221> NAME/KEY: MISC_FEATURE
<222> LOCATION: (76)..(76)
<223> OTHER INFORMATION: Xaa is Ala or Thr
```

```
-continued

<220> FEATURE:
<221> NAME/KEY: MISC_FEATURE
<222> LOCATION: (84)..(84)
<223> OTHER INFORMATION: Xaa is Ser or Arg
<220> FEATURE:
<221> NAME/KEY: MISC_FEATURE
<222> LOCATION: (89)..(89)
<223> OTHER INFORMATION: Xaa is Glu or Asp
<220> FEATURE:
<221> NAME/KEY: MISC_FEATURE
<222> LOCATION: (115)..(115)
<223> OTHER INFORMATION: Xaa is Leu or Thr

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Val Met His Trp Val Arg Gln Ala Pro Gly Xaa Arg Leu Glu Trp Xaa
            35                  40                  45

Gly Tyr Ile Asn Pro Tyr Asn Asp Gly Thr Lys Tyr Asn Glu Lys Phe
        50                  55                  60

Lys Gly Xaa Xaa Thr Xaa Thr Ser Asp Thr Ser Xaa Ser Thr Ala Tyr
65                  70                  75                  80

Met Glu Leu Xaa Ser Leu Arg Ser Xaa Asp Thr Ala Val Tyr Tyr Cys
                85                  90                  95

Ala Arg Pro Ile Tyr Phe Asp Asn Asp Tyr Phe Asp Tyr Trp Gly Gln
            100                 105                 110

Gly Thr Xaa Val Thr Val Ser Ser
            115                 120
```